United States Patent [19]

Chapman et al.

[11] Patent Number: 5,672,583
[45] Date of Patent: Sep. 30, 1997

[54] CARBOXY-PEPTIDYL DERIVATIVES AS ANTIDEGENERATIVE ACTIVE AGENTS

[75] Inventors: Kevin Chapman, Scotch Plains; William Hagmann, Westfield; Philippe Durette, New Providence; Craig Esser, Belford; Ihor Kopka, Millburn; Charles Caldwell, Scotch Plains, all of N.J.

[73] Assignee: Merck & Co., Inc., Rahway, N.J.

[21] Appl. No.: 436,347

[22] PCT Filed: Nov. 18, 1993

[86] PCT No.: PCT/US93/11207

§ 371 Date: May 17, 1995

§ 102(e) Date: May 17, 1995

[87] PCT Pub. No.: WO94/12169

PCT Pub. Date: Jun. 9, 1994

Related U.S. Application Data

[63] Continuation-in-part of Ser. No. 981,970, Nov. 25, 1992, abandoned.

[51] Int. Cl.⁶ ............... A61K 37/02; C07C 259/06; C07C 237/52; C07D 277/62
[52] U.S. Cl. ............... 514/19; 514/20; 514/330; 514/375; 514/367; 514/394; 514/416; 562/450; 562/574; 548/152; 548/217; 548/304.4; 548/486; 548/400; 548/146; 548/206; 548/252; 548/254; 548/336; 548/357; 548/215; 548/240; 546/245; 546/152; 549/491; 549/498; 549/29; 549/65; 549/69; 549/462; 549/49; 544/295; 544/296; 544/264; 544/336; 544/357
[58] Field of Search ............... 514/19, 20, 416, 514/394, 367, 375, 330; 562/567, 574, 450; 548/486, 304.4, 152, 217, 400, 146, 206, 252, 254, 336, 357, 215, 240; 546/245

[56] References Cited

U.S. PATENT DOCUMENTS

| | | | |
|---|---|---|---|
| 4,511,504 | 4/1985 | McCullagh et al. | 260/112.5 |
| 4,568,666 | 2/1986 | McCullagh et al. | 514/20 |
| 4,771,037 | 9/1988 | Roberts et al. | 514/18 |
| 4,935,404 | 6/1990 | Hunger et al. | 514/19 |
| 4,937,243 | 6/1990 | Markwell et al. | 514/237.8 |
| 5,047,400 | 9/1991 | Vincent et al. | 514/18 |
| 5,095,119 | 3/1992 | Ocain et al. | 548/302 |

FOREIGN PATENT DOCUMENTS

| | | |
|---|---|---|
| 0 225 292 | 6/1987 | European Pat. Off. |
| 0 232 027 | 8/1987 | European Pat. Off. |
| 0 274 234 | 7/1988 | European Pat. Off. |
| 0 489 579 | 6/1992 | European Pat. Off. |
| 0 489 577 | 6/1992 | European Pat. Off. |
| WO86/00066 | 1/1986 | WIPO |

OTHER PUBLICATIONS

Kitazawa, et al., Chem. Abstracts, vol. 115, No. 21, Ab.No.231890z (1991).

Kitazawa, et al., Chem. Abstracts, vol. 117, No. 13, p. 716, Ab. No. 130935d (1992).

Baker et al., Nonpeptide Renin Inhibitors Employing a Novel 3-Aza(or oxo)-2,4-dialkyl Glutonic Acid Moiety as a P2/P3 Amide Bond Replacement. J. Med. Chem. (1992) 35, 1722-1734.

*Primary Examiner*—John M. Ford
*Assistant Examiner*—Pavanaram K. Sripada
*Attorney, Agent, or Firm*—Curtis C. Panzer; David L. Rose

[57] ABSTRACT

Novel Carboxy-peptidyl compounds of Formula I are found to be useful inhibitors of matrix metalloendoproteinase-mediated diseases including osteoarthritis, rheumatoid arthritis, septic arthritis, tumor invasion in certain cancers, periodontal disease, corneal ulceration, proteinuria, dystrophic epidermolysis bullosa, coronary thrombosis associated with atherosclerotic plaque rupture, and aneurysmal aortic disease. The matrix metalloendoproteinases are a family of zinc-containing proteinases including but not limited to stromelysin, collagenase, and gelatinase, that are capable of degrading the major components of articular cartilage and basement membranes. The inhibitors claimed herein may also be useful in preventing the pathological sequelae following a traumatic injury that could lead to a permanent disability. These compounds may also have utility as a means for birth control by preventing ovulation or implantation.

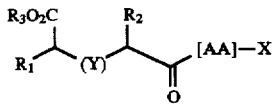

I

19 Claims, No Drawings

CARBOXY-PEPTIDYL DERIVATIVES AS ANTIDEGENERATIVE ACTIVE AGENTS

RELATED U.S. APPLICATION DATA

This application is a continuation-in-part of U.S. Ser. No. 07/981,970, filed Nov. 25, 1992, abandoned.

BACKGROUND OF THE INVENTION

Novel Carboxy-peptidyl compounds of formula I are found to be useful inhibitors of matrix metalloendoproteinase-mediated diseases.

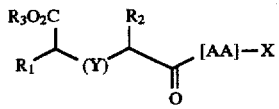

The disability observed in osteoarthritis (OA) and rheumatoid arthritis (RA) is largely due to the loss of articular cartilage. No therapeutic agent in the prior art is known to prevent the attrition of articular cartilage in these diseases.

"Disease modifying antirheumatic drugs" (DMARD), i.e., agents capable of preventing or slowing the ultimate loss of joint function in OA and RA are widely sought. Generic nonsteroidal antiinflammatory drugs (NSAIDs) may be combined with such agents to provide some relief from pain and swelling.

Stromelysin (aka. proteoglycanase, matrix metalloproteinase-3, MMP-3, procollagenase activator, "transin"), collagenase (aka. interstitial collagenase, matrix metalloproteinase-1 (MMP-1)), and gelatinase (aka. type IV collagenase, matrix metalloproteinase-2, MMP-2, 72kDa-gelatinase or type V collagenase, matrix metalloproteinase-9, MMP-9, 95kDa-gelatinase) are metalloendoproteinases secreted by fibroblasts and chondrocytes, and are capable of degrading the major connective tissue components of articular cartilage or basement membranes. Elevated levels of both enzymes have been detected in joints of arthritic humans and animals: K. A. Hasty, R. A. Reife, A. H. Kang, J. M. Stuart, "The role of stromelysin in the cartilage destruction that accompanies inflammatory arthritis", Arthr. Rheum., 33, 388–97 (1990); S. M. Krane, E. P. Amento, M. B. Goldring, S. R. Goldring, and M. L. Stephenson, "Modulation of matrix synthesis and degradation in joint intimation", The Control of Tissue Damage", A. B. Glauert (ed.), Elsevier Sci. Publ., Amsterdam, 1988, Ch. 14, pp 179–95; A. Blanckaert, B. Mazieres, Y. Eeckhout, G. Vaes, "Direct extraction and assay of collagenase from human osteoarthrtic cartilage", Clin. Chim. Acta, 185 73–80 (1989). Each enzyme is secreted from these cells as an inactive proenzyme which is subsequently activated. There is evidence that stromelysin may be the in vivo activator for collagenase, implying a cascade for degradative enzyme activity: A. Ho, H. Nagase, "Evidence that human rheumatoid synovial matrix metalloproteinase 3 is an endogenous activator of procollagenase", Arch Biochem Biophys., 267, 211–16 (1988); G. Murphy, M. I. Crockett, P. E. Stephens, B. J. Smith, A. J. P. Docherty, "Stromelysin is an activator of procollagenase", Biochem. J., 248, 265–8 (1987); Y. Ogata, J. J. Engh. ld, H. Nagase, "Matrix metalprotease-3 (stromelysin) activates the precusor for human matrix metaloproteinase-9, "J. Biol. Chem. 267, 3581–84 (1992). Inhibiting stromelysin could limit the activation of collagenase and gelatinase as well as prevent the degradation of proteoglycan.

That stromelysin inhibition may be effective in preventing articular cartilage degradation has been demonstrated in vitro by measuring the effect of matrix metalloendoproteinase inhibitors on proteoglycan release from rabbit cartilage explants: C. B. Caputo, L. A. Sygowski, S. P. Patton, D. J. Wolanin, A. Shaw, R. A. Roberts, G. DiPasquale, J. Orthopaedic Res., 6, 103–8 (1988).

There is an extensive literature on the involvement of these metalloproteinases in arthritis, but there is very little to guide one in developing a specific inhibitor for each enzyme.

In preliminary studies of rabbit proteoglycanase with substrates and inhibitors, little was found to indicate the enzyme's requirements for hydrolysis or inhibition beyond a preference for hydrophobic residues at the $P_1'$ position: A. Shaw, R. A. Roberts, D. J. Wolanin, "Small substrates and inhibitors of the metalloproteoglycanase of rabbit articular chondrocytes", Adv. Inflam. Res., 12, 67–79 (1988). More extensive studies with a series of substrates revealed that stromelysin will tolerate nearly every amino acid residue around the scissile bond: S. J. Netzel-Arnett, G. B. Fields, H. Nagase, K. Suzuki, W. G. I. Moore, H. Brikedal-Hansen, H. E. Van Wart, Comparative sequence Specificities of human fibroblast and Neutrophil matrix metalloproeinases and inhibitors—Matrix supplement No. 1; H. Brikedal-Hansen, Z. Werk, H. E. Van Wart, Eds.; Gustov Fisher Verlag:New York 1992.

Human rheumatoid synovial collagenase has been shown to share ~50% homology with human stromelysin: S. E. Whitham, G. Murphy, P. Angel, H. J. Rahmsdorf, B. J. Smith, A. Lyons, T. J. R. Harris, J. J. Reynolds, P. Herrlich, A. J. P. Docherty, "Comparison of human stromelysin and collagenase by cloning and sequence analysis", Biochem. J., 240, 913–6 (1986). Many collagenase inhibitors have been designed around the cleavage site of the α-chain sequence of Type II collagen: W. H. Johnson, N. A. Roberts, N. Brokakoti, "Collagenase inhibitors: their design and potential therapeutic use", J. Enzyme Inhib., 2,1–22 (1987); M. A. Schwartz and H. E. Van Wart, Synthetic Inhibitors of Bacterial and Mammalian Interstitial Collagenases, In Prog. Med. Chem. vol. 29; G. P. Ellis and D. K. Luscombe, Eds.; Elsevier Sc. Publ.; 1992; Ch 8, pp 271–334. One such inhibitor, N-[3-(benzyloxycarbonyl)amino-1-carboxy-n-propyl]-L-leucyl-O-methyl-L-tyrosine, N-methylamide, prepared at G. D. Searle, Inc., and shown to be a potent inhibitor of human rheumatoid synovial collagenase ($IC_{50}$= 0.8 μM), was also found to inhibit rabbit bone proteoglycanase ($IC_{50}$=0.5 μM): J. -M. Delaisse, Y. Eeckhout, C. Sear, A. Galloway, K. McCullagh, G. Vaes, "A new synthetic inhibitor of mammalian tissue collagenase inhibits bone resorption in culture", Biochem. Biophys. Res. Commun., 133, 483–90 (1985).

Gelatinase (MR ~72,000) has been isolated from rheumatoid fibroblasts: Y. Okada, T. Morodomi, J. J. Enghild, K. Suzuki, A. Yasui, I. Nakanishi, G. Salvesen, H. Nagase, "Matrix metalloproteinase 2 from human rheumatoid synovial fibroblasts", Eur. J., Biochem., 194, 721–30 (1990). The synthesis of the proenzyme is not coordinately regulated with the other two metalloproteinases and its activation may also be different. The role of gelatinase in the tissue destruction of articular cartilage appears different from the other two enzymes and, therefore, its inhibition may provide additional protection from degradation. A higher molecular weight gelatinase (MR ~95,000; aka. type-V collagenase, matrix metalloproteinase-9, MMP-9) is also secreted by fibroblasts and monocytes and may be involved in cartilage degradation.

The significant proportion of homology between human fibroblast collagenase, stromelysin, and gelatinase leads to the possibility that a compound that inhibits one enzyme may to some degree inhibit all of them.

Compounds that inhibit collagenase, which possess structural portions akin to those of the instant invention include those encompassed by U.S. Pat. No. 4,511,504 U.S. Pat. No. 4,568,666, and EPO 126974 A1.

Compounds of related structure that are claimed to inhibit stromelysin (proteoglycanase) are encompassed by U.S. Pat. No. 4,771,037, and EPO 232027; as well as EPO 489 579 A1, EPO 489 577 A1 and EPO 274 234 A2.

Stromelysin and collagenase inhibitors are believed to have utility in preventing articular cartilage damage associated with septic arthritis. Bacterial infections of the joints can elicit an inflammatory response that may then be perpetuated beyond what is needed for removal of the infective agent resulting in permanent damage to structural components. Bacterial agents have been used in animal models to elicit an arthritic response with the appearance of proteolytic activities. See J. P. Case, J. Sano, R. Lafyatis, E. F. Remmers, G. K. Kumkumian, R. L. Wilder, "Transin/stromelysin expression in the synovium of rats with experimental erosive arhtritis", J. Clin Invest., 84, 1731–40 (1989); R. J. Williams, R. L. Smith, D. J. Schurman, "Septic Arthritis: Staphylococcal induction of chondrocyte proteolytic activity", Arthr. Rheum., 33, 533–41 (1990).

Inhibitors of stromelysin, collagenase, and gelatinase are believed to be useful to control tumor metastasis, optionally in combination with current chemotherapy and/or radiation. See L. M. Matrisian, G. T. Bowden, P. Krieg, G. Furstenberger, J. P. Briand, P. Leroy, R. Breathnach, "The mRNA coding for the secreted protease transin is expressed more abundantly in malignant than in benign tumors", Proc. Natl. Acad. Sci., USA, 83, 9413–7 (1986); S. M. Wilhelm, I. E. Collier, A. Kronberger, A. Z. Eisen, B. L. Marmer, G. A. Grant, E. A. Bauer, G. I. Goldberg, "Human skin fibroblast stromelysin: structure, glycosylation, substrate specificity, and differential expression in normal and tumorigenic cells", Ibid., 84, 6725–29 (1987); Z. Werb et al., Signal transduction through the fibronectin receptor induces collagenase and stromelysin gene expression, J. Cell Biol., 109, 872–889 (1989); L. A. Liotta, C. N. Rao, S. H. Barsky, "Tumor invasion and the extracellular matrix", Lab. Invest., 49, 636–649 (1983); R. Reich, B. Stratford, K. Klein, G. R. Martin, R. A. Mueller, G. C. Fuller, "Inhibitors of collagenase IV and cell adhesion reduce the invasive activity of malignant tumor cells", in Metastasis: Ciba Foundation Symposium; Wiley, Chichester, 1988, pp. 193–210.

Secreted proteinases such as stromelysin, collagenase, and gelatinase play an important role in processes involved in the movement of cells during metastasic tumor invasion. Indeed, there is also evidence that the matrix metalloproteinases are overexpressed in certain metastatic tumor cell lines. In this context, the enzyme functions to penetrate underlying basement membranes and allow the tumor cell to escape from the site of primary tumor formation and enter circulation. After adhering to blood vessel walls, the tumor cells use these same metalloendoproteinases to pierce underlying basement membranes and penetrate other tissues, thereby leading to tumor metastasis. Inhibition of this process would prevent metastasis and improve the efficacy of current treatments with chemotherapeutics and/or radiation.

These inhibitors should also be useful for controlling periodontal diseases, such as gingivitis. Both collagenase and stromelysin activities have been isolated from fibroblasts isolated from inflammed gingiva: V. J. Uitto, R. Applegren, P. J. Robinson, "Collagenase and neutral metalloproteinase activity in extracts of inflamed human gingiva", J. Periodontal Res., 16, 417–424(1981). Enzyme levels have been correlated to the severity of gum disease: C. M. Overall, O. W. Wiebkin, J. C. Thonard, "Demonstration of tissue collagenase activity in vivo and its relationship to intimation severity in human gingiva", J. Periodontal Res., 22, 81–88 (1987).

Proteolytic processes have also been observed in the ulceration of the cornea following alkali burns: S. I. Brown, C. A. Weller, H. E. Wasserman, "Collagenolytic activity of alkali-burned corneas", Arch. Opthalmol., 81, 370–373 (1969). Mercapto-containing peptides do inhibit the collagenase isolated from alkali-burned rabbit cornea: F. R. Burns, M. S. Stack, R. D. Gray, C. A. Paterson, Invest. Opthalmol., 30, 1569–1575 (1989). Treatment of alkali-burned eyes or eyes exhibiting corneal ulceration as a result of infection with inhibitors of these metalloendoproteinases in combination with sodium citrate or sodium ascorbate and/or antimicrobials may be effective in preventing developing corneal degradation.

Stromelysin has been implicated in the degradation of structural components of the glomerular basement membrane (GBM) of the kidney, the major function of which is to restrict passage of plasma proteins into the urine; W. H. Baricos, G. Murphy, Y. Zhou, H. H. Nguyen, S. V. Shah, "Degradation of glomerular basement membrane by purified mammalian metalloproteinases", Biochem. J., 254, 609–612 (1988). Proteinuria, a result of glomerular disease, is excess protein in the urine caused by increased permeability of the GBM to plasma proteins. The underlying causes of this increased GBM permeability are unknown, but proteinases including stromelysin may play an important role in glomerular diseases. Inhibition of this enzyme may alleviate the proteinura associated with kidney malfunction.

Inhibition of stromelysin activity may prevent the rupturing of atherosclerotic plaques leading to coronary thrombosis. The tearing or rupture of atherosclerotic plaques is the most common event initiating coronary thrombosis. Destabilization and degradation of the connective tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin RNA message have been found to be localized to individual cells in atherosclerotic plaques removed from heart transplant patients at the time of surgery: A. M. Henney, P. R. Wakeley, M. J. Davies, K. Foster, R. Hembry, G. Murphy, S. Humphries, "Localization of stromelysin gene expression in atherosclerotic plaques by in situ hybridization", Proc. Nat'l. Acad. Sci. USA, 88, 8154–8158 (1991). Inhibition of stromelysin by these compounds may aid in preventing or delaying the degradation of the connective tissue matrix that stabilizes the atherosclerotic plaques, thereby preventing events leading to acute coronary thrombosis.

It is also believed that inhibitors of matrix metalloproteinases would have utility in treating degenerative aortic disease associated with thinning of the medial aortic wall. Aneurysms are often associated with atherosclerosis in this tissue. Increased levels of the degradative activities of the matrix metalloproteinases have been identified in patients with aortic aneurysms and aortic stenosis: N. Vine, J. T. Powell, "Metalloproteinases in degenerative aortic diseases", Clin, Sci., 81, 233–9 (1991). Inhibition of these enzymes may aid in preventing or delaying the degradation of aortic tissue, thus preventing events leading to acute and often times fatal aortic aneurysms.

It is also believed that specific inhibitors of stromelysin and collagenase should be useful as birth control agents. There is evidence that expression of metalloendoproteinases, including stromelysin and collagenase, is observed in unfertilized eggs and zygotes and at further cleavage stages and increased at the blastocyst stage of fetal development and with endoderm differentiation: C. A. Brenner, R. R. Adler, D. A. Rappolee, R. A. Pedersen, Z. Werb, "Genes for extracellular matrix-degrading metalloproteinases and their inhibitor, TIMP, are expressed during early mammalian development", Genes & Develop., 3, 848–59 (1989). By analogy to tumor invasion, a blastocyst may express metalloproteinases in order to penetrate the extracellular matrix of the uterine wall during implantation. Inhibition of stromelysin and collagenase during these early developmental processes should presumably prevent normal embryonic development and/or implantation in the uterus. Such intervention would constitute a novel method of birth control. In addition there is evidence that collagenase is important in ovulation processes. In this example, a coveting of collagen over the apical region of the follicle must be penetrated in order for the ovum to escape. Collagenase has been detected during this process and an inhibitor has been shown to be effective in preventing ovulation: J. F. Woessner, N. Morioka, C. Zhu, T. Mukaida, T. Butler, W. J. LeMaire "Connective tissue breakdown in ovulation", Steroids, 54, 491–499 (1989). There may also be a role for stromelysin activity during ovulation: C. K. L. Too, G. D. Bryant-Greenwood, F. C. Greenwood, "Relaxin increases the release of plasminogen activator, collagenase, and proteo-glycanase from rat granulosa cells in vitro", Endocrin., 115, 1043–1050 (1984).

Collagenolytic and stromelysin activity have also been observed in dystrophobic epidermolysis bullosa: A. Kronberger, K. J. Valle, A. Z. Eisen, E. A. Bauer, J. Invest. Dermatol., 79 208–211 (1982); D. Sawamura, T. Sugawara, I. Hashimoto, L. Bruckmer-Tuderman, D. Fujimoto, Y. Okada, N. Utsumi, H. Shikata, Biochem. Biophys. Res. Commun., 174, 1003–8 (1991). Inhibition of metalloendoproteinases should limit the rapid destruction of connective components of the skin.

In addition to extracellular matrix comprising structural components, stromelysin can degrade other in vivo substrates including the inhibitors $\alpha_1$-proteinase inhibitor and may therefore influence the activities of other proteinases such as elastase: P. G. Winyard, Z. Zhang, K. Chidwick, D. R. Blake, R. W. Carrell, G. Murphy, "Proteolytic inactivation of human $\alpha_1$-antitrypsin by human stromelysin", FEBS Letts., 279, 1, 91–94 (1991). Inhibition of the matrix metalloendoproteinases may potentiate the antiproteinase activity of these endogenous inhibitors.

SUMMARY OF THE INVENTION

The invention encompasses novel carboxy-peptidyl compounds of Formula I which are useful inhibitors of matrix metalloendoproteinase-mediated diseases including degenerative diseases (such as defined above) and certain cancers.

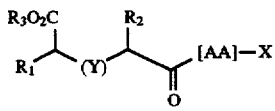

I

DETAILED DESCRIPTION OF THE INVENTION

In one embodiment, the invention encompasses a compound of Formula I

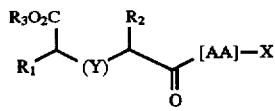

I or a pharmaceutically acceptable salt thereof wherein:

Y is —$CH_2$—, O, S, —$CH(C_{1-3}Alkyl)$—,

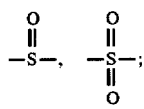

$R_1$ is hydrogen, substituted $C_{1-8}$alkyl, or substituted $C_{2-8}$ alkenyl wherein the substituent is selected from the group consisting of:

(a) hydrogen, (b) carboxy, (c) Aryl wherein the Aryl group is selected from the group consisting of
 (1) phenyl,
 (2) naphthyl,
 (3) pyridyl,
 (4) furyl,
 (5) pyrryl,
 (6) thienyl,
 (7) isothiazolyl,
 (8) imidazolyl,
 (9) benzimidazolyl,
 (10) tetrazolyl,
 (11) pyrazinyl,
 (12) pyrimidyl,
 (13) quinolyl,
 (14) isoquinolyl,
 (15) benzofuryl,
 (16) isobenzofuryl,
 (17) benzothienyl,
 (18) pyrazolyl,
 (19) indolyl,
 (20) isoindolyl,
 (21) purinyl,
 (22) carbazolyl,
 (23) isoxazolyl,
 (24) thiazolyl,
 (25) oxazolyl,
 (26) benzthiazolyl, and
 (27) benzoxazolyl, and mono and di-substituted Aryl as defined above in items (1) to (27) wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

(d)

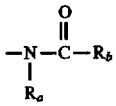

wherein $R_a$ and $R_b$ are each independently hydrogen; Aryl and mono and di-substituted Aryl as defined above (c); or substituted $C_{1-6}$alkyl wherein the substitutent is selected from hydroxy, halo, and phenyl, or wherein $R_a$ and $R_b$ are joined such that together with the nitrogen and carbon atoms to which they are attached, there is formed a saturated or unsaturated lactam such as

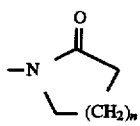

wherein n is 1, 2 or 3 or benzo fused lactam ring such as

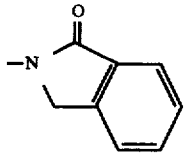

wherein the lactam portion thereof is a ring of 5, 6, 7 or 8 atoms, said lactam or benzolactam to have a single hetero atom;

(e)

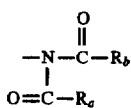

wherein $R_a$ and $R_b$ are each independently hydrogen; Aryl and mono and di-substituted Aryl as defined above (c); or substituted $C_{1-6}$alkyl wherein the substitutent is selected from hydroxy, halo, and phenyl, or wherein $R_a$ and $R_b$ are joined such that together with the nitrogen and carbon atoms to which they are attached, there is formed a saturated or unsaturated lactim (or imide) such as

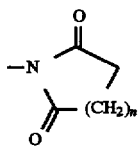

or benzolactim (or imide) ring such as

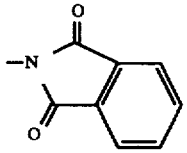

wherein the lactim portion thereof is a ring of 5, 6, 7 or 8 atoms, said lactim or benzolactim to have a single hetero atom;

(f) amino and mono or disubstituted amino wherein the substituent is selected from $C_{1-6}$ alkyl and Aryl where aryl is defined in (c);

(g)

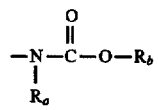

wherein $R_a$ and $R_b$ are each independently hydrogen; or $C_{1-6}$ Alkyl; or Aryl$C_{0-6}$Alkyl or mono or di substituted Aryl$C_{0-6}$Alkyl wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl and Aryl is defined as in (c); or wherein $R_a$ and $R_b$ are joined such that together with the nitrogen and oxygen atoms to which they are attached, there is formed a saturated or unsaturated monocyclic urethane or benzofused cyclic urethane such as

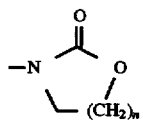

or

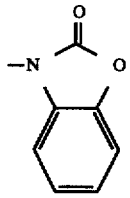

wherein the urethane ring contains 5, 6, 7 or 8 atoms, said ring to contain 2 heteroatoms;

(h)

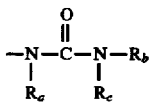

wherein $R_a$, $R_b$, and $R_c$ are each independently hydrogen; or $C_{1-6}$ Alkyl; or Aryl$C_{0-6}$Alkyl or mono or di substituted Aryl$C_{0-6}$Alkyl wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl and Aryl is defined as in (c); or wherein $R_a$ and $R_b$ are joined such that together with the nitrogen atoms to which they are attached, there is formed a saturated or unsaturated monocyclic urea or benzofused cyclic urea such as

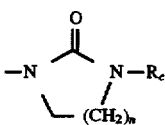

-continued

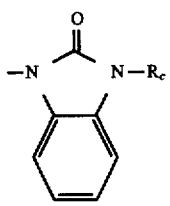

wherein the urea ring contains up to 8 atoms, said ring to contain 2 heteroatoms; or $R_b$ and $R_c$ are joined such that together with the nitrogen atom to which they are attached, there is formed a saturated or unsaturated monocyclic ring or benzofused ring containing 5, 6, 7 or 8 atoms, said ring to contain 1 heteroatom;

(i)

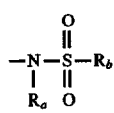

wherein $R_a$ and $R_b$ are each independently hydrogen; or $C_{1-6}$ Alkyl; or $ArylC_{0-6}Alkyl$ or mono or di substituted $ArylC_{0-6}Alkyl$ wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl and Aryl is defined as in (c); or wherein $R_a$ and $R_b$ are joined such that together with the nitrogen and sulfer atoms to which they are attached, there is formed a saturated or unsaturated monocyclic sulfonaminde or benzofused cyclic sulfonamide such as

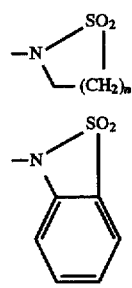

wherein the sulfonamide ring contains 5, 6, 7 or 8 atoms, said ring to contain 2 heteroatoms;

(j)

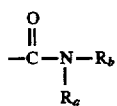

wherein $R_a$ and $R_b$ are each independently hydrogen; or $C_{1-6}$ Alkyl; or $ArylC_{0-6}Alkyl$ or mono or di substituted $ArylC_{0-6}Alkyl$ wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl and Aryl is defined as in (c); or $R_a$ and $R_b$ are joined such that together with the nitrogen atom to which they are attached, there is formed a saturated or unsaturated monocyclic ring or benzofused ring containing 5, 6, 7 or 8 atoms, said ring to contain 1 heteroatom;

(k)

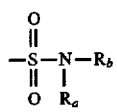

wherein $R_a$ and $R_b$ are each independently hydrogen; or $C_{1-6}$ Alkyl; or $ArylC_{0-6}Alkyl$ or mono or di substituted $ArylC_{0-6}Alkyl$ wherein the substituents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl and Aryl is defined as in (c); or $R_a$ and $R_b$ are joined such that together with the nitrogen atom to which they are attached, there is formed a saturated or unsaturated monocyclic ring or benzofused ring containing up to 8 atoms, said ring to contain 1 heteroatom;

$R_2$ is aryl$C_{1-4}$alkyl, aryl substituted $C_{1-4}$alkyl, (aryl$C_{1-4}$alkyl)-aryl$C_{1-4}$alkyl, or biaryl$C_{1-4}$alkyl wherein the substituent is $C_{1-3}$alkyl or hydroxy, and wherein the aryl group is selected from the group consisting of:

(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl, and mono and di-substituted Aryl as defined above in items (1) to (27) wherein the substitutents are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

$R_3$ is (a) H,
(b) Z, where Z is a pharmaceutically counterion, such as sodium, potassium, calcium or magnesium,
(c) $C_{1-10}$alkyl,
(d) Aryl or Aryl $C_{1-3}$alkyl, wherein the aryl group is selected from the group consisting of (1) phenyl, and
(2) substituted phenyl, wherein the substitutent is carboxy, carboxyC$_{1-3}$alkyl, aminocarbonyl, C$_{1-6}$alkylaminocarbonyl;

AA is a single bond or an amino acid of formula II

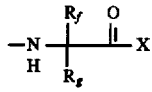

wherein R$_f$ and R$_g$ are individually selected from:
(a) hydrogen,
(b) C$_{1-6}$alkyl,
(c) mercapto C$_{1-6}$alkyl,
(d) hydroxy C$_{1-6}$alkyl,
(e) carboxy C$_{1-6}$alkyl,
(f) amino substituted C$_{2-6}$alkyl
(g) aminocarbonyl C$_{1-6}$alkyl,
(h) mono- or di-C$_{1-6}$alkyl amino C$_{2-6}$alkyl,
(i) guanidino C$_{2-6}$alkyl,
(j) substituted phenyl C$_{1-6}$alkyl, wherein the substitutent is hydrogen, hydroxy, carboxy, C$_{1-4}$ alkyl, or C$_{1-4}$alkyloxy,
(k) substituted indolyl C$_{1-6}$alkyl, wherein the substitutent is hydrogen, hydroxy, carboxy, C$_{1-4}$ alkyl, or C$_{1-4}$alkyloxy,
(l) substituted imidazolyl C$_{2-6}$alkyl wherein the substitutent is hydrogen, hydroxy, carboxy, C$_{1-4}$ alkyl, or C$_{1-4}$alkyloxy,
(m) substituted pyridyl C$_{1-6}$alkyl wherein the substitutent is hydrogen, hydroxy, carboxy, C$_{1-4}$ alkyl, or C$_{1-4}$alkyloxy,
(n) substituted pyridylamino C$_{1-6}$alkyl wherein the substitutent is hydrogen, hydroxy, carboxy, C$_{1-4}$ alkyl, or C$_{1-4}$alkyloxy,
(o) substituted pyimidinyl C$_{1-6}$alkyl wherein the substitutent is hydrogen, hydroxy, carboxy, C$_{1-4}$ alkyl, or C$_{1-4}$alkyloxy, X is

wherein R$_5$ and R$_6$ are each individually selected from the group consisting of:
(a) H,
(b) C$_{1-10}$alkyl,
(c) Aryl or ArylC$_{1-6}$alkyl, wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl,
(25) benzoxazolyl,
(26) thiazolyl, and
(27) oxazolyl.

and mono and di-substituted Aryl as defined above in items (1) to (27) wherein the substitutents are independently selected from C$_{1-6}$alkyl, C$_{1-6}$alkyloxy, halo, hydroxy, amino, C$_{1-6}$alkylamino, aminoC$_{1-6}$alkyl, carboxyl, carboxylC$_{1-6}$alkyl, and C$_{1-6}$alkylcarbonyl.

For purposes of this specification, and as appreciated by those of skill in the art, the unsaturated rings such as those described in definitions R$_1$ (d), (e), (g), (h), (i), (j) and (k) are intended to include rings wherein a double bond is present at one, two or more of the available positions. Similarly, the term aryl C$_{0-6}$ alkyl, as found in definitions such as R$_1$ (g), (h), (i), (j) and (k) are intended to describe aryl and aryl C$_{1-6}$ alkyl. Similarly the term (aryl C$_{1-4}$ alkyl-) aryl C$_{1-4}$ arkyl, is intended to describe as aryl C$_{1-4}$ alkyl group wherein the aryl is substituted as aryl C$_{1-4}$ alkyl- such as —CH$_2$ phenyl.

In an alternative embodiment the invention encompasses compound of formula I

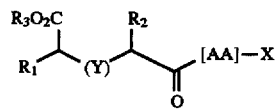

or a pharmaceutically acceptable salt thereof wherein:
Y is —CH$_2$—, O, S, —CH(C$_{1-3}$Alkyl)—,

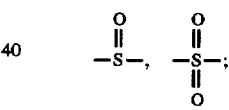

R$_1$ is hydrogen or a mono- or di-substituted C$_{1-6}$alkyl, C$_{1-6}$alkoxy, or C$_{2-6}$alkenyl wherein the substituents are independently selected from the group consisting of:
(a) hydrogen,
(b) carboxy,
(c) aminocarbonyl,
(d) C$_{1-6}$alkoxy,
(e) C$_{1-6}$alkylcarbonyl,
(f) aryl group selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,

(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl, which can be mono- or di-substituted with substitutents independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, or $C_{1-6}$alkylcarbonyl;

(g) aryloxy wherein the aryl groups are defined above;

(h) aroyl wherein the aryl groups are defined above;

(i)

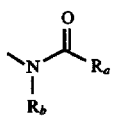

wherein $R_a$ and $R_b$ are each independently hydrogen; aryl or heteroaryl and mono and di-substituted aryl or heteroaryl as defined above; or substituted $C_{1-6}$alkyl wherein the substitutent is selected from hydroxy, halo, and aryl or heteroaryl, or wherein $R_a$ and $R_b$ are joined together with the nitrogen and carbon atoms to which they are attached, to form a lactam or benzolactam ring wherein the lactam portion thereof is a ring of 5, 6, 7, or 8 atoms, said lactam or benzolactam containing a single hetero atom;

(j)

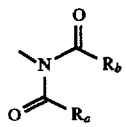

wherein $R_a$ and $R_b$ are each independently hydrogen; aryl or heteroaryl and mono and di-substituted aryl or heteroaryl as defined above; or substituted $C_{1-6}$alkyl wherein the substitutent is selected from hydroxy, halo, and aryl, or wherein $R_a$ and $R_b$ are joined together with the nitrogen and carbon atoms to which they are attached to form a cyclic imide, or is benzofused onto a cyclic imide, wherein the cyclic imide portion thereof is a ring of 5, 6, 7, or 8 atoms, said cyclic imide containing a single hereto atom;

(k) amino or mono- or di-substituted amino wherein the substituents are independently selected from $C_{1-6}$ alkyl and aryl or heteroaryl as defined above;

(l)

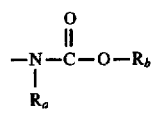

wherein $R_a$ and $R_b$ are each independently hydrogen; $C_{1-6}$ alkyl; aryl as defined above; or wherein $R_a$ and $R_b$ are joined together with the nitrogen and oxygen atoms to which they are attached, to form a cyclic-urethane or a benzofused cyclic-urethane wherein the urethane ring contains 5, 6, 7, or 8 atoms, said ring containing the two heteroatoms;

(m)

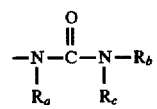

wherein $R_a$, $R_b$, and $R_c$ are each independently hydrogen; $C_{1-6}$ alkyl; aryl as defined above; or wherein $R_a$ and $R_b$ are joined together with the nitrogen atoms to which they are attached to form a cyclic-urea or benzofused cyclic-urea, said urea ring containing 5, 6, 7, or 8 atoms and said two nitrogens;

(n)

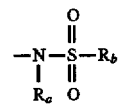

wherein $R_a$ and $R_b$ are each independently hydrogen; $C_{1-6}$ alkyl; aryl as defined above; or wherein $R_a$ and $R_b$ are joined together with the nitrogen and sulfur atoms to which they are attached, to form a cyclic-sulfonamide or benzofused cyclic-sulfonamide ring, said sulfonamide ring containing 5, 6, 7, or 8 atoms and said heteroatoms;

(o)

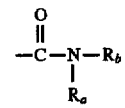

wherein $R_a$ and $R_b$ are each independently hydrogen; $C_{1-6}$ alkyl; aryl as defined above; or wherein $R_a$ and $R_b$ are joined together with the nitrogen atom to which they are attached, to form a heterocycle or benzofused heterocycle ring, said ring containing 5, 6, 7, or 8 atoms and said nitrogen atom;

(p)

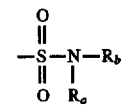

wherein $R_a$ and $R_b$ are each independently hydrogen; $C_{1-6}$ alkyl; aryl as defined above; or wherein $R_a$ and $R_b$ are joined together with the nitrogen atom to which they are attached, to form a heterocycle or benzofused heterocycle ring, said ring containing 5, 6, 7, or 8 atoms and said nitrogen atom;

$R_2$ is aryl$C_{1-4}$alkyl, aryl substituted $C_{1-4}$alkyl, (aryl$C_{1-4}$alkyl)aryl$C_{1-4}$alkyl, or biaryl$C_{1-4}$alkyl wherein the substituent is $C_{1-3}$alkyl or hydroxy, and wherein the aryl group is selected from the group consisting of:

(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl, and mono and di-substituted Aryl as defined above in items (1) to (27) wherein the substitutents on the aryl group are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

$R_3$ is (a) H,
(b) Z, where Z is a pharmaceutically acceptable counterion,
(c) $C_{1-10}$alkyl,
(d) Aryl or Aryl $C_{1-3}$alkyl, wherein the aryl group is selected from the group consisting of
 (1) phenyl, and
 (2) substituted phenyl, wherein the substituent is carboxy, carboxy$C_{1-3}$alkyl, aminocarbonyl, $C_{1-6}$alkylaminocarbonyl;

AA is a single bond or an amino acid of formula II

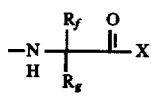

II wherein $R_f$ and $R_g$ are individually selected from:

(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino substituted $C_{2-6}$alkyl
(g) aminocarbonyl $C_{1-6}$alkyl,
(h) mono- or di-$C_{1-6}$alkyl amino $C_{2-6}$alkyl,
(i) guanidino $C_{2-6}$alkyl,
(j) substituted phenyl $C_{1-6}$alkyl, wherein the substitutent is hydrogen, hydroxy, carboxy, $C_{1-4}$ alkyl, or $C_{1-4}$alkyloxy,
(k) substituted indolyl $C_{1-6}$alkyl, wherein the substituent is hydrogen, hydroxy, carboxy, $C_{1-4}$ alkyl, or $C_{1-4}$alkyloxy,
(l) substituted imidazolyl $C_{2-6}$alkyl wherein the substitutent is hydrogen, hydroxy, carboxy, $C_{1-4}$ alkyl, or $C_{1-4}$alkyloxy,
(m) substituted pyridyl $C_{1-6}$alkyl wherein the substitutent is hydrogen, hydroxy, carboxy, $C_{1-4}$ alkyl, or $C_{1-4}$alkyloxy,
(n) substituted pyridylamino $C_{1-6}$alkyl wherein the substitutent is hydrogen, hydroxy, carboxy, $C_{1-4}$ alkyl, or $C_{1-4}$alkyloxy,
(o) substituted pyrimidinyl $C_{1-6}$alkyl wherein the substitutent is hydrogen, hydroxy, carboxy, $C_{1-4}$ alkyl, or $C_{1-4}$alkyloxy, X is

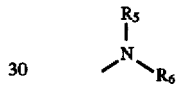

wherein $R_5$ and $R_6$ are each individually selected from the group consisting of:

(a) H,
(b) $C_{1-10}$alkyl,
(c) Aryl or Aryl$C_{1-6}$alkyl, wherein the aryl group is selected from the group consisting of
 (1) phenyl,
 (2) naphthyl,
 (3) pyridyl,
 (4) pyrryl,
 (5) furyl,
 (6) thienyl,
 (7) isothiazolyl,
 (8) imidazolyl,
 (9) benzimidazolyl,
 (10) tetrazolyl,
 (11) pyrazinyl,
 (12) pyrimidyl,
 (13) quinolyl,
 (14) isoquinolyl,
 (15) benzofuryl,
 (16) isobenzofuryl,
 (17) benzothienyl,
 (18) pyrazolyl,
 (19) indolyl,
 (20) isoindolyl,
 (21) purinyl,
 (22) carbazolyl,
 (23) isoxazolyl,
 (24) benzthiazolyl,
 (25) benzoxazolyl,
 (26) thiazolyl, and
 (27) oxazolyl.

and mono and di-substituted Aryl as defined above in items (1) to (27) wherein the substitutents are independently selected from C$_{1-6}$alkyl, C$_{1-6}$alkyloxy, hydroxyC$_{1-6}$alkyl, C$_{1-6}$alkoxyC$_{1-6}$alkyl, halo, hydroxy, amino, C$_{1-6}$alkylamino, aminoC$_{1-6}$alkyl, carboxyl, carboxylC$_{1-6}$alkyl, and C$_{1-6}$alkylcarbonyl;

As will be appreciated by those of skill in the art, the ring structures of R$_1$ (i), (j), (k), (l), (m), (n), (o) and (p) formed by joining R$_a$ and R$_b$ are the same as those described in the first embodiment, and the example structures provided in the first embodiment are equally applicable to the alternative embodiment.

One class of each embodiment concerns compounds wherein

Y is —CH$_2$— or —CH(C$_{1-3}$Alkyl)—,

R$_1$ is substituted C$_{1-6}$alkyl, wherein the substituent is selected from the group consisting of:
(a) hydrogen,
(b) carboxy,
(c) Aryl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl, and
(9) indolyl;

and mono and di-substituted Aryl as defined above in items (1) to (9) wherein the substitutents are independently selected from C$_{1-6}$alkyl, C$_{1-6}$alkyloxy, halo, hydroxy, amino, C$_{1-6}$alkylamino, aminoC$_{1-6}$alkyl, carboxyl, carboxylC$_{1-6}$alkyl, and C$_{1-6}$alkylcarbonyl;

(d)

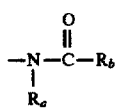

wherein R$_a$ and R$_b$ are each independently hydrogen; Aryl and mono and di-substituted Aryl as defined above (c); or substituted C$_{1-6}$alkyl wherein the substitutent is selected from hydroxy, halo, and phenyl, or wherein R$_a$ and R$_b$ are joined together to form a lactam or benzolactam ring as defined above.

A sub-class of this class is the compounds wherein:
R$_3$ is
(a) H,
(b) Z,
(c) C$_{1-6}$alkyl,
(d) phenyl, substituted phenyl, wherein the substitutent is carboxy, carboxy C$_{1-3}$alkyl, amino carbonyl.

Within this sub-class are the compounds wherein:
AA is an amino acid including glycine, alanine, valine, leucine, isoleucine, 2-tert-butyl-glycine, penicilliamine, serine, threonine, aspartic acid, asparagine, glutamic acid, glutamine, lysine, hydroxy-lysine, homohistidine, arginine, phenylalanine, tyrosine, tryptophan, cysteine, methionine, ornithine, homoserine, or citrulline.

Alternatively, within this sub-class the amino acids AA can be defined as follows:

AA is

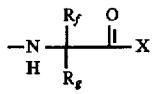

II wherein R$_f$ and R$_g$ are individually selected from:
(a) hydrogen,
(b) C$_{1-4}$alkyl,
(c) mercapto C$_{1-3}$alkyl,
(d) hydroxy C$_{1-4}$alkyl,
(e) carboxy C$_{1-4}$alkyl,
(f) amino C$_{2-4}$alkyl,
(g) aminocarbonyl C$_{1-4}$alkyl,
(h) mono- or di-C$_{1-6}$alkyl amino C$_{2-4}$alkyl,
(i) guanidino C$_{2-4}$alkyl,
(j) substituted phenyl C$_{1-4}$alkyl, wherein the substituent is hydrogen, hydroxy, carboxy, or C$_{1-3}$ alkyl,
(k) substituted indolyl C$_{1-4}$alkyl, wherein the substituent is hydrogen, hydroxy, carboxy, or C$_{1-3}$ alkyl,
(l) substituted imidazolyl C$_{2-6}$alkyl wherein the substituent is hydrogen, hydroxy, carboxy, or C$_{1-4}$ alkyl.

One group of compounds may be further identified as that wherein X is

wherein R$_5$ and R$_6$ are each individually selected from the group consisting of
(a) H,
(b) C$_{1-6}$alkyl, or
(c) Aryl, or ArylC$_{1-6}$alkyl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl, and
(10) pyridyl.

A smaller group within this group are the compounds wherein:
Y is —CH$_2$—
R$_1$ is hydrogen, substituted C$_{1-4}$alkyl or substituted C$_{2-4}$alkenyl wherein the substituent is hydrogen, and Aryl wherein the aryl is selected from the group consisting of
R$_2$ is arylC$_{1-4}$alkyl, or biarylC$_{1-4}$alkyl wherein the aryl group is is selected from the group consisting of phenyl, thienyl, pyridyl, or naphthyl;
R$_3$ is
(a) H, or
(b) Z;
R$_f$ is H;
R$_g$ is
(a) hydrogen;
(b) C$_{1-6}$alkyl; or
(c) guanidino C$_{1-6}$alkyl
R$_5$ is H; and R$_6$ is Aryl or monosubstitued aryl, wherein the aryl is phenyl and the substituent is selected from C$_{1-8}$alkyl, halo, and hydroxy.

R$_b$ is H.

Exemplifying the present invention are the following compounds:

a) 2(R)-(2-(4-(1-n-Propyl)phenyl)ethyl)-1,5-pentanedioic acid 1-(L-leucine, N-phenylamide)amide.
b) 2(R)-(2-(4-(1-n-Propyl)phenyl)ethyl)-1,5-pentanedioic acid 1-(2(S)-t-butyl)glycine, N-phenylamide)amide:
c) 2(R)-(2-(4-(1-n-Propyl)phenyl)ethyl)-1,5-pentanedioic acid 1-(2(S)-t-butyl)glycine, N-(4-pyridyl)amide)amide:
d) 2(R)-(2-(4-(1-n-Propyl)phenyl)ethyl)-1,5-pentanedioic acid 1-(L-arginine, N-methylamide)amide
e) 2(R)-(2-(4-(1-n-Propyl)phenyl)ethyl)-4-methyl-1,5-pentanedioic acid 1-(L-leucine, N-phenylamide)amide
f) 2(R)-(2-(4-(1-n-Propyl)phenyl)ethyl)-4-methyl-1,5-pentanedioic acid 1-(2(S)-t-butyl)glycine, N-phenylamide)amide:
g) 2(R)-(2-(4-(1-n-Propyl)phenyl)ethyl)-4-methyl-1,5-pentanedioic acid 1-(2(S)-(4-thiazolylmethyl)glycine, N-phenylamide)amide:
h) 2(R)-(2-(4-(1-n-Propyl)phenyl)ethyl)-4-methyl-1,5-pentanedioic acid 1-(2(S)-(3-pyridylmethyl)glycine, N-phenylamide)amide:
i) 2(R)-(2-(4-(1-n-Propyl)phenyl)ethyl)-4-methyl-1,5-pentanedioic acid 1-(L-leucine, N-(4-pyridyl)amide)amide:
j) 2(R)-(2-(4-(1-n-Propyl)phenyl)ethyl)-4-methyl-1,5-pentanedioic acid 1-(2(S)-(2-pyridylmethyl)glycine, N-phenylamide)amide:
k) 2(R)-(2-(4-(1-n-Propyl)phenyl)ethyl)-4-methyl-1,5-pentanedioic acid 1-(L-arginine, N-phenylamide)amide:
l) 2(R)-(2-(4-(1-n-Propyl)phenyl)ethyl)-4-methyl-1,5-pentanedioic acid 1-(L-phenylalanine, N-4-pyridyl)amide)amide:
m) 2(R)-(2-(4-(1-n-Propyl)phenyl)ethyl)-4-(1-(4-(N-(2-Oxoisoindolinyl))-butyl))-1,5-pentanedioic acid 1-(L-leucine, N-phenylamide)amide
n) 2(R)-(2-(4-(1-n-Propyl)phenyl)ethyl)-4-(1-(4-(N-(2-Oxoisoindolinyl))-but-2-enyl))-1,5-pentanedioic acid 1-(L-leucine, N-phenylamide) amide
o) 2(R)-(2-(4-(4-fluorophenyl)phenyl)ethyl)-4-methyl-1,5-pentanedioic acid 1-(L-leucine, N-phenylamide)amide.
p) 2(R)-(2-(4-(phenyl)phenyl)ethyl)-4-methyl-1,5-pentanedioic acid 1-(L-leucine, N-phenylamide)amide:
q) 2(R)-(2-(4-(4-methoxyphenyl)phenyl)ethyl)-4-methyl-1,5-pentanedioic acid 1-(L-leucine phenylamide)amide:
r) 2(R)-(2-(4-(4-methylphenyl)phenyl)ethyl)-4-methyl-1,5-pentanedioic acid 1-(L-leucine phenylamide)amide:
s) 2(R)-(2-(4-(4-hydroxy-n-butyl)-phenyl)-ethyl)-4-methylpentanedioic acid 1-(S-leucine phenylamide) amide
t) 2(R),4(S)-(2-(4-(3-hydroxy-n-propyl)phenyl)ethyl)-4-methyl-1,5-pentanedioic acid 1-(L-leucine, N-phenylamide)amide:
u) 2(R)-(2-phenylethyl)-4-methyl-1,5-pentanedioic acid 1-(L-leucine, N-phenylamide)amide
v) 2(R)-(2-(4-(1-n-Propyl)phenyl)ethyl)-1,5-pentanedioic acid 1-(L-leucine, N-ethylamide)amide
w) 2(R)-(2-(4-(1-n-Propyl)phenyl)ethyl)-1,5-pentanedioic acid 1-(L-leucine, N-isopropylamide)amide:
x) 2(R)-(2-(4-(1-n-Propyl)phenyl)propyl)-1,5-pentanedioic acid 1-(2(S)-tert-butyl-glycine, N-(4-pyridyl)amide) amide
y) 2(R)-(3-(4-(1-n-Propyl)phenyl)propyl)-1,3-pentanedioic acid 1-(L-leucine, N-phenylamide)amide:
z) 2(R)-(2-(4-(1-n-Propyl)phenyl)ethyl)-4-hexyl-1,5-pentanedioic acid 1-(L-leucine, N-phenylamide)amide.
aa) 2(R)-(2-(4-(1-n-Propyl)phenyl)ethyl)-4-butyl-1,5-pentanedioic acid 1-(L-leucine, N-phenylamide)amide:
ab) 2(R)-(2-(4-(1-n-Propyl)phenyl)ethyl)-4-(3-methylbenzyl)-1,5-pentanedioic acid 1-(L-leucine, N-phenylamide)amide
ac) 2(R)-(2-(4-(1-n-Propyl)phenyl)ethyl)-4-(4-(2-benzimidazolyl)butyl)-1,5-pentanedioic acid 1-(L-leucine, N-phenylamide)amide
ad) 2(R)-(2-(4-(1-n-Propyl)phenyl)ethyl)-4-(4-(2-benzthiazolyl)butyl)-1,5-pentanedioic acid 1-(L-leucine, N-phenylamide)amide
ae) 2(R)-(2-(4-(1-n-Propyl)phenyl)ethyl)-4-(4-(2-benzoxazolyl)butyl)-1,5-pentanedioic acid 1-(L-leucine, N-phenylamide)amide.
af) 2(R)-(2-(4-(1-n-Propyl)phenyl)ethyl)-4-carboxy-1,9-nonanedioic acid 1-(L-leucine, N-phenylamide)amide 9-piperidineamide.
ag) 2(R)-(2-(4-(1-Propyl)phenyl)ethyl)-4-carboxy-1,9-nonanedioic acid 1-(L-leucine, N-methylamide)amide 9-phenylamide:
ah) 2(R)-(2-(4-(1-n-Propyl)phenyl)ethyl)-4-carboxy-1,9-nonanedioic acid 1-(L-leucine, N-methylamide)amide 9-tert-butylamide:
ai) 2(R)-(2-(4-(1-n-Propyl)phenyl)ethyl)-4-carboxy-1,9-nonanedioic acid 1-(L-leucine, N-methylamide)amide 9-benzylamide:
aj) 2(R)-(2-(4-(1-n-Propyl)phenyl)ethyl)-4-carboxy-1,9-nonanedioic acid 1-(L-leucine, N-methylamide)amide 9-morpholineamide:
ak) 2(R)-(2-(4-(1-n-Propyl)phenyl)ethyl)-4-carboxy-1,9-nonanedioic acid 1-(L-leucine, N-methylamide)amide 9-(1(R)-phenylethyl)amide:
al) 2(R)-(2-(4-(1-n-Propyl)phenyl)ethyl)-4-carboxy-1,9-nonanedioic acid 1-(L-leucine, N-methylamide)amide 9-(1(S)-phenylethyl)amide:
am) 2(R)-(2-(4-(1-n-Propyl)phenyl)ethyl)-4-carboxy-1,9-nonanedioic acid 1-(L-leucine, N-methylamide)amide 9-(N-methyl-N-phenyl)amide:
an) 2(R)-(2-(4-(1-n-Propyl)phenyl)ethyl)-4-carboxy-1,9-nonanedioic acid 1-(L-leucine, N-methylamide)amide 9-(N'-methylpiperazine)amide, trifluoroacetic acid salt:
ao) 2(R)-(2-(4-(1-n-Propyl)phenyl)ethyl)-4-carboxy-1,9-nonanedioic acid 1-(L-leucine, N-methylamide)amide 9-(3-pyridyl)amide:
ap) 2(R)-(2-(4-(1-Propyl)phenyl)ethyl)-4-carboxy-1,9-nonanedioic acid 1-(L-leucine, N-methylamide)amide
aq) 2(R)-(2-(4-(1-Propyl)phenyl)ethyl)-1,5-pentanedioic acid 1-((R)-(S-p-methoxybenzyl)penicillamine, N-phenylamide)amide.
ar) 2(R)-(2-(4-(1-Propyl)phenyl)ethyl)-1,5-pentanedioic acid 1-((R)-(S-p-methoxybenzyl)penicillamine sulfone, N-phenylamide)amide.
as) 2-(2-(4-(1-Propyl)phenyl)ethyl)-4-(1-(4-(2-phthalimido))butyl)-1,5-pentandioic acid 1-(L-leucine, N-methylamide)amide
at) 2(R)-(2-(4-(1-n-Propyl)phenyl)ethyl)-4-(4-benzoylamino-1-butyl)-1,5-pentandioic acid 1-(L-leucine, N-methylamide)amide.
au) 2(R)-(2-(4-(1-n-Propyl)phenyl)ethyl)-4-(4-pivaloylamino-1-butyl)-1,5-pentandioic acid 1-(L-leucine, N-methylamide)amide:
av) 2(R)-(2-(4-(1-n-Propyl)phenyl)ethyl)-4-(4-phenylsulfonylamino-1-butyl)-1,5-pentandioic acid 1-(L-leucine, N-methylamide)amide:
aw) 2(R)-(2-(4-(1-n-Propyl)phenyl)ethyl)-4-(4-(N'-phenylureido)-1-butyl)-1,5-pentandioic acid 1-(L-leucine, N-methylamide)amide.

ax) 2(R)-(2-(4-(1-n-Propyl)phenyl)ethyl)-4-(4-phenyloxycarbonylamino-1-butyl)-1,5-pentandioic acid 1-(L-leucine, N-methylamide)amide.

ay) 2(R)-(2-(4-(1-n-Propyl)phenyl)ethyl)-4-(4-N'-benzyloxycarbonyl amino-L-prolylamino)-1-butyl)-1,5-pentandioic acid 1-(L-leucine, N-methylamide)amide.

az) 2(R)-(2-(4-(1-n-Propyl)phenyl)ethyl)-4-(4-cyclopentylamino-1-butyl)-1,5-pentandioic acid 1-(L-leucine, N-methylamide)amide:

ba) 2(R)-(2-(4-(1-n-Propyl)phenyl)ethyl)-4-(4-(2-carboxybenzoylamino)-1-butyl)-1,5-pentandioic acid 1-(L-leucine, N-methylamide)amide.

bb) 2(R)-(2-(4-(1-n-Propyl)phenyl)ethyl)-4-(4-cyano-1-butyl)-1,5-pentandioic acid 1-(L-leucine, N-phenylamide)amide.

This invention also concerns pharmaceutical composition and methods of treatment of stromelysin-mediated or implicated disorders or diseases (as described above) in a patient (which shall be defined to include man and/or mammalian animals raised in the dairy, meat, or fur industries or as pets) in need of such treatment comprising administration of the stromelysin inhibitors of formula I as the active constituents.

Similarly, this invention also concerns pharmaceutical compositions and methods of treatment of collagenase mediated or implicated disorders or diseases (as described above) in a patient in need of such treatment comprising administration of the collagenase inhibitors of formula (I) as the active constituents.

Similarly, this invention also concerns pharmaceutical compositions and methods of treatment of gelatinase-mediated or implicated disorders or diseases (as described above) in a patient in need of such treatment comprising administration of the gelatinase inhibitors of formula (I) as the active constituents.

Moreover the invention also encompasses compositions, treatment, and method for co-administration of a compound of formula I with a PMN elastase inhibitor such as those described in EP 0 337 549 which published on Oct. 18, 1989, which is hereby incorporated by reference.

Compounds of the instant invention are conveniently prepared using the procedures described generally below and more explicitly described in the Example section thereafter.

SCHEME 1

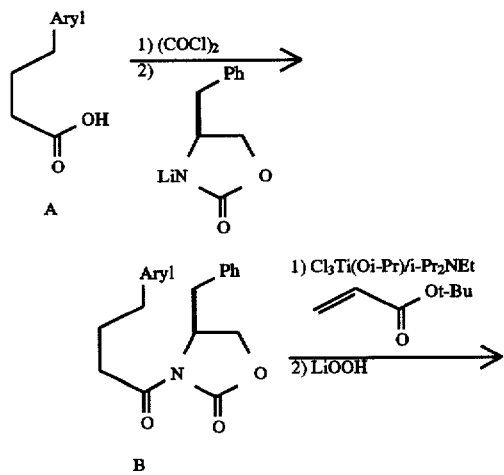

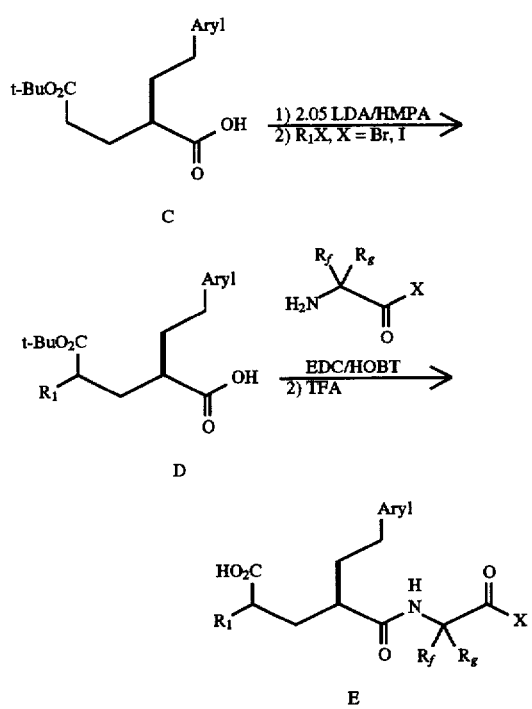

The inhibitors described in Scheme I can be prepared as follows. An arylalkyl carboxylic acid is first converted to its corresponding acid chloride using oxallyl chloride and this is used to acylate lithio-4-benzyl-2-oxazolidinone. The derived imide is then enolized with $Cl_3Ti(Oi-Pr)$ in the presence of Hunig's base and alkylated with t-butyl acrylate. The chiral auxilliary is then remove with lithium hydroperoxide and the resulting acid ester enolized with lithium diisoprpyl amide and alkylated with an alkyl halide. The acid is then coupled to an amine and the t-butyl ester deprotected with trifluoroacetic acid to afford the desired inhibitors.

Compounds of the present invention have inhibitory activities with respect to metalloendoproteinases such as stromelysin, collagenase and gelatinase. The enzyme inhibition assays are described in detail below in the Examples.

The capacity to inhibit the hydrolysis by stromelysin may be demostrated in an assay in which the extent of enzymatic cleavage of a substrate Arg-Pro-Lys-Pro-Leu-Ala-Phe-TrpNH$_2$ at the Ala-Phe is determined fluorometrically (excitation gamma=280 nm; emission gamama=345 nm) with varying concentrations of inhibitor. The capacity of representative compounds of formula I to inhibit collagenase and gelatinase lysis may be determined using the method of M. S. Stack et al, J. Biol. Chem 264, 4277 (1989). In such assay, a fluorogenic substrate Dnp-Pro-Leu-Gly-Leu-Trp-Ala-D-NH$_2$ is used. The tryptophan fluorescence is efficiently quenched by the dinitrophenyl group but when it is hydrolyzed by collagenase or gelatinase, there is increased fluorescence with cleavage occurring at the Gly-Leu bond.

This invention also relates to a method of treatment for patients (including man and/or mammalian animals raised in the dairy, meat, or fur industries or as pets) suffering from disorders or diseases which can be attributed to stromelysin as previously described, and more specifically, a method of treatment involving the administration of the matrix metalloendoproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloendoproteinases such as found in certain metastatic tumor cell lines.

For the treatment of rheumatoid arthritis, osteoarthritis, and in diseases and indications resulting from the over-expression of matrix metalloendoproteinases such as found in certain metastatic tumor cell lines or other diseases mediated by the matrix metalloendoproteinases, the compounds of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula I, and as such are not intended to limit the invention as set forth in the claims appended, thereto.

EXAMPLE 1

2(R)-(2-(4-(1-n-Propyl)phenyl)ethyl)-1,5-pentanedioic acid 1-(L-leucine, N-phenylamide) amide

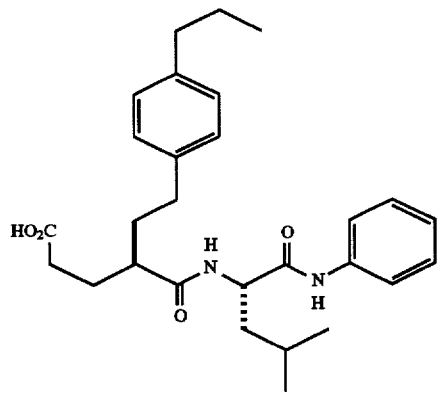

Step A

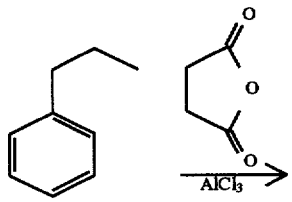

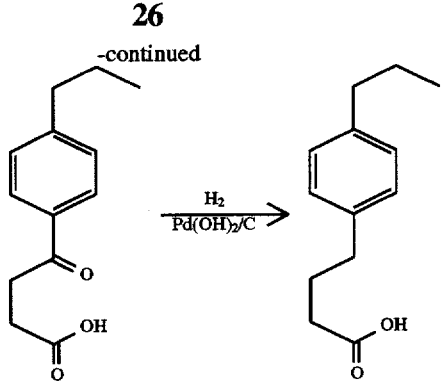

4-(4-(1-n-Propyl)phenyl)butanoic acid: To a solution of propylbenzene (14.6 g, 121.4 mmol) in 243 mL of a solution of aluminum chloride in nitrobenzene (1.0M, 243 mmol) was added succinic anhydride (12.15 g, 121.4 mmol). After 3 h, the reaction was quenched with 2N hydrochloric acid, diluted with ether and washed 5 times with dilute hydrochloric acid. The organics were then extracted three times with dilute sodium hydroxide and the combined aqueous layers washed three times with ether. The aqueous layer was then acidified with concentrated hydrochloric acid and extracted twice with ether. The combined ether layers were dried over magnesium sulfate, filtered and concentrated in vacuo to give a brown free flowing solid. This product was disolved in 250 mL of acetic acid and ~1 g of Pearlman's catalyst was added. The mixture was stirred vigorously under 1 atmosphere of hydrogen for 16 h, filtered through a pad of celite and concentrated in vacuo. The product was diluted with toluene and concentrated in vacuo to remove the remaining acetic acid to afford 19.3 g of the title compound as a pale-tan crystalline solid: 400 MHz $^1$H NMR (CDCl$_3$) δ 7.08 (s, 4H), 2.7–2.3 (m, 6H), 1.94 (m, 2H), 1.62 (m, 2H), 0.93 (t, 3H).

Step B

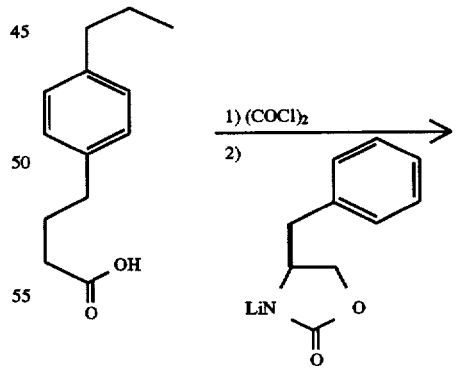

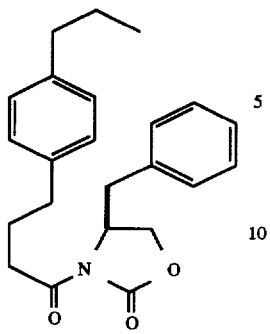

3-(4-(4-(1-n-Propyl)phenyl)butanoyl)-4(S)-phenylmethyl-2-oxazolidinone: 4-(4-(1-n-Propyl)phenyl) butanoic acid (19.3 g) was disolved in dichloromethane and 25 mL of oxalyl chloride was added. After gas evolution ceased (~3 h) the mixture was concentrated in vacuo. To a solution of 4(S)-phenylmethyl-2-oxazolidinone (16.6 g, 93.6 mmol) in 250 mL of dry THF at −78° C. was added butyl lithium (64.4 mL, 1.6M, 102.99 mmol). After 5 min, a solution of the acid chloride in THF was added via cannula. After 15 min, the reaction was partitioned between ethyl acetate and 2N hydrchloric acid and the layers separated. The organics were washed twice with 2N hydrochloric acid and three times with dilute sodium bicarbonate then dried over sodium sulfate, filtered, and concentrated in vacuo. The product was purified by flash filtration through silica-gel eluting with 10% ethyl acetate in hexane to give a pale-yellow oil which crystallized upon dissolution in 5% ethyl acetate in hexane. The mixture was concentrated and recrystallized from hexane to afford the title compound as colorless needles (20.8 g): 400 MHz $^1$H NMR (CDCl$_3$) δ 7.4–7.0 (m, 9H), 4.63 (m, 1H), 4.14 (m, 2H), 3.20 (dd, 1H, J=3.30, 13.27 Hz), 2.97 (m, 2H), 2.73 (dd, 1H, J=9.72, 13.42 Hz), 2.67 (t, 2H, J=7.68 Hz), 2.53 (t, 2H, J=7.61 Hz), 2.00 (m, 2H), 1.61 (m, 2H), 0.92 (t, 3H, J=7.33 Hz).

Step C

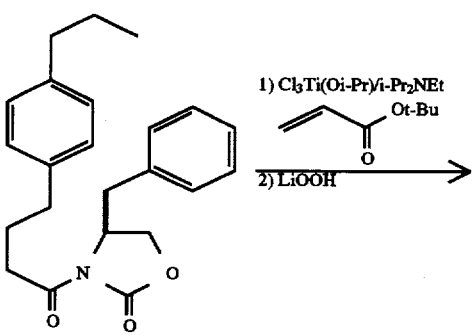

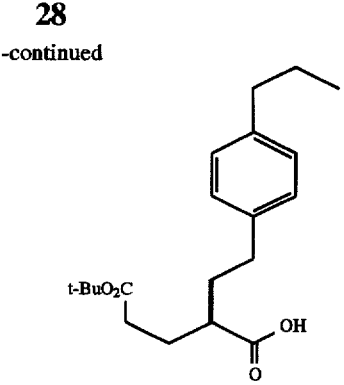

5-tert-Butyl ester 2(R)-(2-(4-(1-n-propyl)phenyl)ethyl)-1, 5-pentanedioic acid: To a solution of tetrachloride (4.80 mL, 43.8 mmol) in 200 mL of dichloromethane at 0° C. was added titanium tetraisopropoxide (4.29 mL, 14.4 mmol). After 5 min, Hunig's base (10.13 mL, 58.2 mmol) was added. After 15 min, a solution of 3-(4-(4-3-(4-(4-(1-n-propyl)phenyl)butanoyl)-4(S)-phenylmethyl-2-oxazolidinone (20.25 g, 55.4 mmol) in 50 mL of dichloromethane was added via cannula and washed in with 10 mL of dichloromethane. After 60 min, freshly distilled tert-butyl acrylate was added and the mixture stirred at 0° C. for 3 h and at ambient temperature for 3 h. The mixture was diluted with ethyl acetate and washed five times with dilute hydrochloric acid and twice with dilute sodium bicarbonate. The organics were then dried over sodium sulfate, filtered, and concentrated in vacuo. The crude product was purified by MPLC (medium pressure liquid chromatography) on silica-gel (55×450 mm column, eluting with first 5% ethyl acetate in hexane then 10% ethyl acetate in hexane) to afford 23.9 g of the Michael adduct as a colorless oil: 400 MHz $^1$H NMR (CDCl$_3$) δ 7.35–7.15 (m, 5H), 7.05 (s, 4H), 4.49 (m, 1H), 4.08 (m, 2H), 3.83 (m, 1H), 3.30 (dd, 1H, J=3.29, 13.26 Hz), 2.7–1.5 (m, 12H), 1.42 (s, 9H), 0.89 (t, 3H, J=7.36 Hz). To a solution of the Michael adduct in 750 mL of THF and 250 mL of water was added 27 mL of 30% H$_2$O$_2$ and 2.23 g of lithium hdroxide monohydrate. After 2 h, TLC showed no starting material. The reaction was quenched with 300 mL of 1M Na$_2$SO$_3$ and 300 mL of saturated NaHCO$_3$. The THF was removed in vacuo and the mixture acidified with 2N hydrochloric acid and extracted three times with ethyl acetate. The combined organic layers were dried over sodium sulfate, filtered, and concentrated in vacuo. The product was purified by MPLC on silica-gel (55×450 mm column, eluting with 20% ethyl acetate in hexane followed by 1% acetic acid and 20% ethyl acetate in hexane) to give 14.5 g of the title compound as a colorless oil: 400 MHz $^1$H NMR (CDCl$_3$) δ 7.07 (s, 4H), 2.7–2.2 (m, 7H), 2.0–1.5 (m, 6H), 1.41 (s, 9H), 0.91 (t, 3H, J=7.28 Hz).

Step D

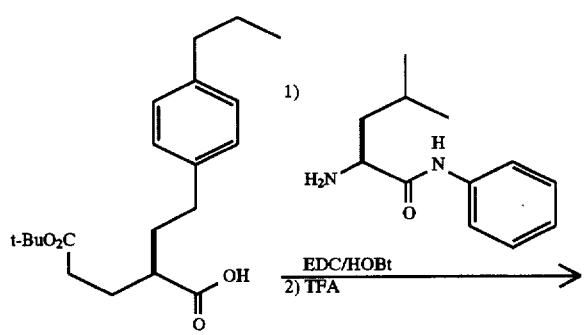

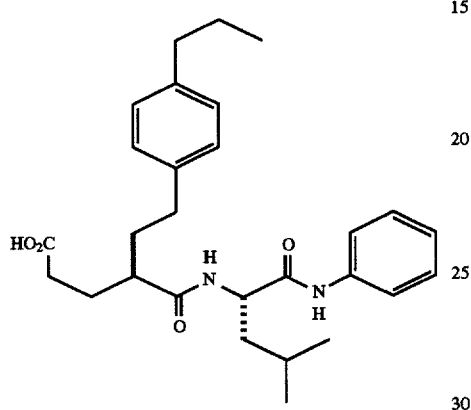

2(R)-(2-(4-(1-n-Propyl)phenyl)ethyl)-1,5-pentanedioic acid 1-(L-leucine, N-phenylamide)amide: To a solution of 5-tert-butyl ester 2(R)-(2-(4-(1-n-propyl)phenyl)ethyl)-1,5-pentanedioic acid (1.01 g, 3.01 mmol), S-leucine phenylamide (652 mg, 3.16 mmol), and hydroxybenzotriazole (HOBt) (610 mg, 4.51 mmol) in 20 mL of THF at 0° C. was added ethyl dimethylaminopropyl carbodiimide (EDC) (634 mg, 3.31 mmol). The mixture was allowed to warm slowly to ambient temperature and stirred overnight. The mixture was diluted with ethyl acetate and washed three times with 2N hydrochloric acid and three times with dilute sodium bicarbonate. The organics were then dried over sodium sulfate, filtered, and concentrated in vacuo. The product was purified by MPLC on silica-gel (35×350 mm column, eluting with 15% ethyl acetate in hexane) to afford 1.34 g of the amide as a colorless solid: 400 MHz $^1$H NMR (CDCl$_3$) δ 8.58 (br s, 1H), 7.49 (d, 2H, J=7.49 Hz), 7.26 (t, 2H, J=7.57 Hz), 7.05 (t, 1H, J=7.40 Hz), 7.00 (d, 2H, J=8.10 Hz), 6.93 (d, 2H, J=8.05 Hz), 6.05 (br d, 1H, J=7.97 Hz), 4.61 (m, 1H), 2.6–1.5 (m, 16H), 1.38 (s, 9H), 0.96 (d, 3H, J=6.47 Hz), 0.93 (d, 3H, J=6.35 Hz), 0.90 (t, 3H, J=7.32 Hz). The tert-butyl ester was dissolved in 10 mL of dichloromethane and 10 mL of TFA was added. After 20 min, the mixture was concentrated in vacuo, diluted with toluene, and concentrated in vacuo. The solid product was recrystallized from ~3% ether in hexane to afford the title compound as a colorless solid: 400 MHz $^1$H NMR (CD$_3$OD) δ 7.50 (d, 2H, J=7.56 Hz), 7.29 (t, 2H, J=7.47 Hz), 7.08 (t, 1H, J=7.42 Hz), 7.01 (s, 4H), 4.60 (dd, 1H, J=5.35, 9.91 Hz), 2.6–2.1 (m, 7H), 1.9–1.5 (m, 9H), 1.00 (d, 3H, J=6.46 Hz), 0.98 (d, 3H, 6.55 Hz), 0.90 (t, 3H, J=7.38 Hz).

The following additional compounds were prepared according to the method of Example 1.

2(R)-(2-(4-(1-n-Propyl)phenyl)ethyl)-1,5-pentanedioic acid 1-(2(S)-t-butyl)glycine, N-phenylamide)amide: mass spectrum: m/z 467 (M+1), 489 (M+Na); 400 MHz $^1$H NMR (CD$_3$OD): δ 0.90 (t, 3H), 1.08 (s, 9H), 1.58 (m, 2H), 4.48 (d, 1H), 7.00 (m, 4H), 7.08 (t, 1H), 7.30 (t, 2H), 7.55 (d, 2H), and 7.87 (d, 1H).

2(R)-(2-(4-(1-n-Propyl)phenyl)ethyl)-1,5-pentanedioic acid 1-(2(S)-t-butyl)glycine, N-(4-pyridyl)amide)amide: mass spectrum: m/z 468 (M+1), 474 (M+Li); 400 MHz $^1$H NMR (CD$_3$OD): δ 0.90 (t, 3H), 1.11 (s, 9H), 1.59 (m, 2H), 2.28 (t, 2H), 2.50 (t, 2H), 7.04 (m, 4H), 8.20 (d, 2H), and 8.60 (d, 2H).

EXAMPLE 2

2(R)-(2-(4-(1-n-Propyl)phenyl)ethyl)-1,5-pentanedioic acid 1-(L-arginine, N-methylamide) amide

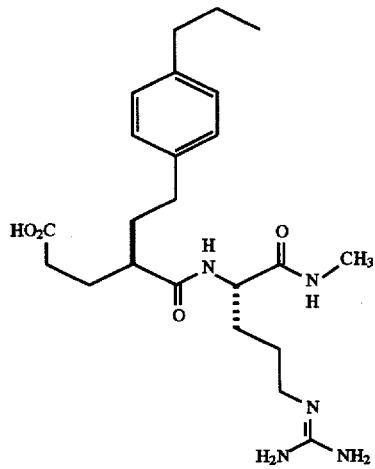

Step A

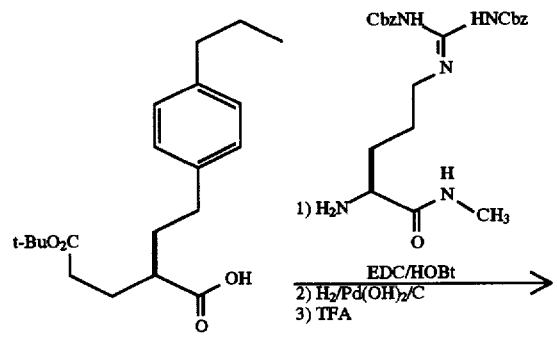

31
-continued

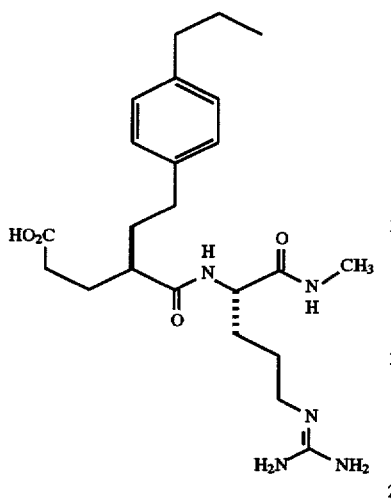

2(R)-(2-(4-(1-n-Propyl)phenyl)ethyl)-1,5-pentanedioic acid 1-(L-arginine, N-methylamide)amide: To a solution of 5-tert-butyl ester 2(R)-(2-(4-(1-n-propyl)phenyl)ethyl)-1,5-pentanedioic acid (406 mg, 1.21 mmol), ω,ω-bis-CBZ S-arginine methylamide hydrochloride (628 mg, 1.28 mmol), hydroxybenzotriazole (HOBt) (246 mg, 1.82 mmol), and N-methylmorpholine (NMM) (422 µL, 3.84 mmol), in 20 mL of DMF at 0° C. was added ethyl dimethylaminopropyl carbodiimide (EDC) (634 mg, 3.31 mmol). The mixture was allowed to warm slowly to ambient temperature and stirred overnight. The mixture was diluted with ethyl acetate and washed three times with 2N hydrochloric acid and three times with dilute sodium bicarbonate. The organics were then dried over sodium sulfate, filtered, and concentrated in vacuo. The product was purified by MPLC on silica-gel (22×300 mm column, eluting with 10%. ethyl acetate in hexane) to afford 238 mg of the amide as a colorless solid: 400 MHz $^1$H NMR (CDCl$_3$) δ 7.4–7.0 (m, 14H), 5.23 (AB, 2H), 5.12 (AB, 2H), 4.52 (m, 1H), 4.27 (m, 1H), 3.78 (m, 1H), 2.6–1.5 (m, 17H), 1.38 (s, 9H), 0.92 (t, 3H). The amide was disolved in 10 mL of dichloromethane and 10 mL of TFA was added. After 40 min, the mixture was concentrated in vacuo, diluted with toluene and concentrated in vacuo to give a colorless solid: 400 MHz $^1$H NMR (CD$_3$OD) δ 7.38 (m, 10H), 7.05 (s, 4H), 5.28 (s, 2H), 5.23 (s, 2H), 4.32 (m, 1H), 3.89 (m, 2H), 2.69 (s, 3H), 2.6–2.1 (m, 6H), 1.9–1.5 (m, 10H), 0.91 (t, 3H, J=7.38 Hz). The acid was disolved in 20 mL of methanol and ~100 mg of Pd(OH)$_2$/C was added. The mixture was stirred vigorously under 1 atmosphere of hydrogen for 90 min the filtered and concentrated in vacuo to afford the title compound as a colorless solid: 400 MHz $^1$H NMR (CD$_3$OD) δ 7.06 (s, 4H), 4.36 (dd, 1H, J=5.76, 8.02 Hz), 3.20 (m, 2H), 2.74 (s, 3H), 2.6–2.2 (m, 7H), 1.9–1.5 (m, 10H), 0.91 (t, 3H, J=7.28 Hz).

32
EXAMPLE 3

2(R)-(2-(4-(1-n-Propyl)phenyl)ethyl)-4-methyl-1,5-pentanedioic acid 1-(L-leucine, N-phenylamide) amide

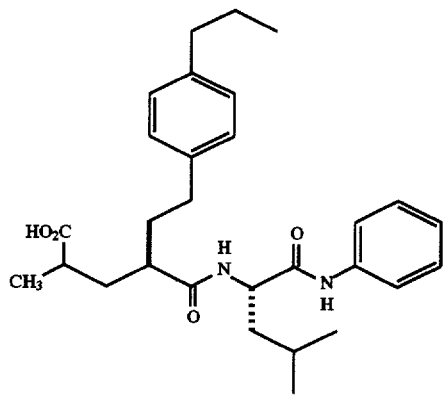

Step A 5-tert-Butyl ester 2(R)-(2-(4-(1-n-propyl)phenyl)ethyl)-4-methyl-1,5-pentanedioic acid: To a soution of lithium diisopropylamide (2.23 mmol) in 5 mL of THF at −78° C. was added a solution of 5-tert-butyl ester 2(R)-(2-(4-(1-n-propyl)phenyl)ethyl)-1,5-pentanedioic acid (355 mg, 1.06 mmol) in 1 mL of THF and 0.5 mL of HMPA. After 30 min at −78° C., methyl iodide (330 µL, 5.3 mmol) was added and the mixture stirred for three hours. The reaction was quenched with excess 2N hydrochloric acid and the mixture diluted with ethyl acetate. The organics were washed three times with 2N hydrochloric acid, dried over sodium sulfate, filtered, and concentrated in vacuo to afford the title compound as a 3:1 mixture of diastereomers: 400 MHz $^1$H NMR (CD$_3$OD) δ 7.08 (m, 4H), 2.9–1.5 (m, 15H), 1.40 (s), 1.38 (s), 1.10 (d, J=6.91 Hz), 1.09 (d, J=6.59 Hz), 0.91 (m, 3H).

Step B 5-tert-Butyl ester 1-benzyl ester 2(R)-(2-(4-(1-n-propyl)phenyl)ethyl)-4-methyl-1,5-pentanedioic acid: To a solution of 5-tert-butyl ester 2(R)-(2-(4-(1-n-propyl)phenyl)ethyl)-4-methyl-1,5-pentanedioic acid from Step A (473 mg) in methylene chloride (10 mL) were added benzyl alcohol (148 µL, 1.43 mmol) followed by 4-dimethylaminopyridine (13 mg, 0.106 mmol) and EDC (312 mg, 1.63 mmol). The reaction mixture was stirred overnight at room temperature, diluted with methylene chloride, washed with water, saturated sodium hydrogencarbonate solution, saturated brine solution, dried (sodium sulfate), and evaporated. The product was purified by flash silica gel chromatography using 3% diethyl ether in hexane to afford the title compound as an approximately 3:1 mixture of diastereomers which was separated by HPLC (Waters Delta-Prep 4000 instrument using a 40×300 mm, 6 micron Nova-Pak silica radial compression column eluting with a gradient from 2–5% diethyl ether in hexane over 45 min at a flow rate of 75 mL/min). Fractions containing the pure less mobile diastereomer were combined and evaporated to afford 98 mg of the title compound as a single isomer at the C-4 position.

Step C 5-tert-Butyl ester 2(R)-(2-(4-(1-n-propyl)phenyl)ethyl)-4-methyl-1,5-pentanedioic acid: A solution of 5-tert-butyl ester 1-benzyl ester 2(R)-(2-(4-(1-n-propyl)phenyl)ethyl)-4-methyl-1,5-pentanedioic acid (97.8 mg, 0.223 mmol) in methanol (4 mL) was stirred for 90 min in the presence of 20% palladium hydroxide-on-carbon (23 mg) under an atmosphere of hydrogen gas. The catalyst was removed by filtration through Celite and washed with methanol. The combined filtrate and washings were evaporated and dried in vacuo to afford 76.9 mg of a single isomer of the title compound as a colorless oil.

Step D 5-tert-Butyl ester 2(R)-(2-(4-(1-n-propyl)phenyl)ethyl)-4-methyl-1,5-pentanedioic acid 1-(L-leucine, N-phenylamide)amide: To a solution of 5-tert-butyl ester 2(R)-(2-(4-(1-n-propyl)phenyl)ethyl)-4-methyl-1,5-pentanedioic acid (76.9 mg, 0.221 mmol) in DMF (2 mL) were added hydroxybenzotriazole (HOBt) (45 mg, 0.333 mmol) and leucine phenyl amide (47.7 mg, 0.231 mmol). The mixture was cooled in an ice-bath and after 15 min EDC (46.5 mg, 0.243 mmol) was added. The reaction mixture was allowed to warm to room temperature and stirred overnight. It was then diluted with diethyl ether, washed with water, N hydrochloric acid, saturated sodium hydrogencarbonate solution, dried (sodium sulfate) and evaporated. The product was purified by flash silica gel chromatography eluting with 15% ethyl acetate in hexane to afford 93.1 mg of the title amide as a single diastereomer at C-4.

Step E

2(R)-(2-(4-(1-n-Propyl)phenyl)ethyl)-4-methyl-1,5-pentanedioic acid 1-(L-leucine, N-phenylamide)amide: A solution of 5-tert-butyl ester 2(R)-(2-(4-(1-n-propyl)phenyl)ethyl)-4-methyl-1,5-pentanedioic acid 1-(L-leucine, N-phenylamide)amide (92 mg) in methylene chloride (2 mL) cooled in an ice-bath was treated with trifluoroacetic acid (0.5 mL) and allowed to warm to room temperature. After several hours, TLC (20% ethyl acetate in hexane) indicated complete disappearance of starting compound. The mixture was evaporated and coevaporated several times with toluene and then dried in vacuo to afford the title compound as a single diastereomer at C-4: mass spectrum: m/z 481 (M+1); 400 MHz $^1$H NMR (CD$_3$OD): δ 0.90 (t, 3H), 0.93 (d, 3H), 0.96 (d, 3H), 1.17 (d, 3H), 2.50 (t, 2H), 4.60 (m, 1H), 7.00 (s, 4H), 7.08 (t, 1H), 7.30 (t, 2H), 7.56 (d, 2H), and 8.33 (d, 1H).

The following additional compounds were prepared according to the method of Example 3.

2(R)-(2-(4-(1-n-Propyl)phenyl)ethyl)-4-methyl-1,5-pentanedioic acid 1-(2(S)-t-butyl)glycine, N-phenylamide) amide: mass spectrum: m/z 481 (M+1); 400 MHz $^1$H NMR (CD$_3$OD): δ 0.90 (t, 3H), 1.08 (s, 9H), 1.19 (d, 3H), 1.58 (m, 2H), 4.49 (d, 1H), 7.00 (m, 4H), 7.10 (t, 1H), 7.30 (t, 2H), 7.53 (d, 2H), and 7.90 (d, 1H).

2(R)-(2-(4-(1-n-Propyl)phenyl)ethyl)-4-methyl-1,5-pentanedioic acid 1-(2(S)-(4-thiazolylmethyl)glycine, N-phenylamide)amide: m/z 522 (M+1); 400 MHz $^1$H NMR (CD$_3$OD): δ 0.90 (t, 3H), 1.02 (d, 3H), 1.58 (m, 2H), 3.27 (dd, 1H), 3.38 (dd, 1H), 4.98 (dd, 1H), 7.00 (m, 4H), 7.09 (t, 1H), 7.30 (t, 2H), 7.39 (d, 1H), 7.52 (d, 2H), and 9.00 (d, 1H).

2(R)-(2-(4-(1-n-Propyl)phenyl)ethyl)-4-methyl-1,5-pentanedioic acid 1-(2(S)-(3-pyridylmethyl)glycine, N-phenylamide)amide: mass spectrum: m/z 516 (M+1); 400 MHz $^1$H NMR (CD$_3$OD): δ 0.90 (t, 3H), 1.03 (d, 3H), 1.58 (m, 2H), 2.50 (t, 2H), 3.20 (dd, 1H), 3.41 (dd, 1H), 4.96 (m, 1H), 7.00 (m, 4H), 7.10 (t, 1H), 7.30 (t, 2H), 7.53 (d, 2H), 7.89 (dd, 1H), 8.41 (d, 1H), 8.56 (d, 1H), and 8.68 (d, 1H).

2(R)-(2-(4-(1-n-Propyl)phenyl)ethyl)-4-methyl-1,5-pentanedioic acid 1-(L-leucine, N-(4-pyridyl)amide)amide: mass spectrum: m/z 482 (M+1); 400 MHz $^1$H NMR (CD$_3$OD): δ 0.90 (t, 3H), 1.18 (d, 3H), 2.52 (t, 2H), 4.58 (m, 1H), 7.03 (m, 4H), 8.19 (d, 2H), and 8.60 (d, 2H).

2(R)-(2-(4-(1-n-Propyl)phenyl)ethyl)-4-methyl-1,5-pentanedioic acid 1-(2(S)-(2-pyridylmethyl)glycine, N-phenylamide)amide: mass spectrum: m/z 516 (M+1); 400 MHz $^1$H NMR (CD$_3$OD): δ 0.90 (t, 3H), 1.04 (d, 3H), 2.50 (t, 2H), 3.37 (dd, 1H), 3.58 (dd, 1H), 5.08 (m, 1H), 7.00 (m, 4H), 7.10 (t, 1H), 7.30 (t, 2H), 7.53 (d, 2H), 7.72 (m, 1H), 7.82 (d, 1H), 8.28 (m, 1H), and 8.69 (d, 1H).

2(R)-(2-(4-(1-n-Propyl)phenyl)ethyl)-4-methyl -1,5-pentanedioic acid 1-(L-arginine, N-phenylamide)amide: mass spectrum: m/z 524 (M+1); 400 MHz $^1$H NMR (CD$_3$OD): δ 0.90 (t, 3H), 1.18 (d, 3H), 1.58 (m, 2H), 2.50 (t, 2H), 4.55 (m, 1H), 7.00 (s, 4H), 7.10 (t, 1H), 7.30 (t, 2H), and 7.56 (d, 2H).

2(R)-(2-(4-(1-n-Propyl)phenyl)ethyl)-4-methyl-1,5-pentanedioic acid 1-(L-phenylalanine, N-4-pyridyl)amide) amide: mass spectrum: m/z 516 (M+1); 400 MHz $^1$H NMR (CD$_3$OD): δ 0.90 (t, 3H), 0.98 (d, 3H), 1.60 (m, 2H), 2.51 (t, 2H), 3.05 (dd, 1H), 3.22 (dd, 1H), 7.02 (m, 4H), 8.12 (d, 2H), and 8.58 (d, 2H).

EXAMPLE 4

2(R)-(2-(4-(1-n-Propyl)phenyl)ethyl)-4-(1-(4-(N-(2-Oxoisoindolinyl))-butyl))-1,5-pentanedioic acid 1-(L-leucine, N-phenylamide)amide

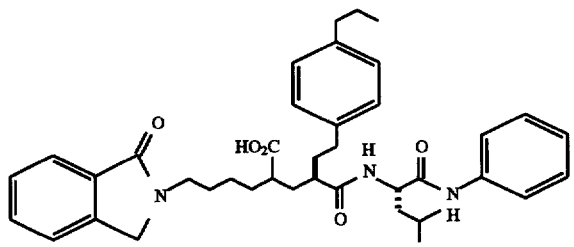

Step A

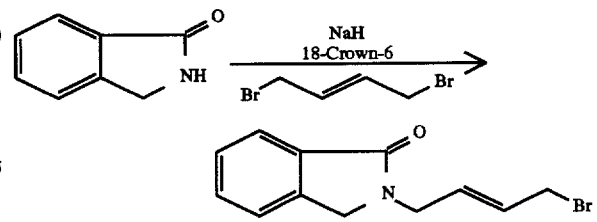

4-(N-(2-Oxoisoindolinyl))-1-bromo-2-butene: To a solution of oxoisoindoline (1.28 g, 9.61 mmol) and 1,4-dibromo-2-butene (20.6 g, 96.1 mmol) in 100 mL of was added sodium hydride (345 mg, 12.0 mmol) and a catalytic mount of 18-crown-6. After 2 h, the mixture was diluted with ether and washed three times with dilute sodium bisulfate the dried over magnesium sulfate, filtered, and concentrated in vacuo. The product was preadsobed onto silica-gel with ether and concentrated to dryness. The free flowing gel was placed atop a short column of silica-gel and eluted first with 5% ethyl acetate in hexane to remove the excess dibromobutene, and then with 50% ethyl acetate in hexane to afford the product. This product was further purified by MPLC on silica-gel (35×350 mm column, eluting with 30% ethyl acetate in hexane) to afford 1.39 g of the title compound as a colorless oil which crystallized on standing: 400 MHz $^1$H NMR (CDCl$_3$) δ 7.84 (d, 1H, J=7.53 Hz), 7.55–7.40 (m, 3H), 5.95–5.75 (m, 2H), 4.35 (s, 2H), 4.24 (d, 2H, J=6.69 Hz), 3.93 (d, 2H, J=7.00 Hz).

Step B

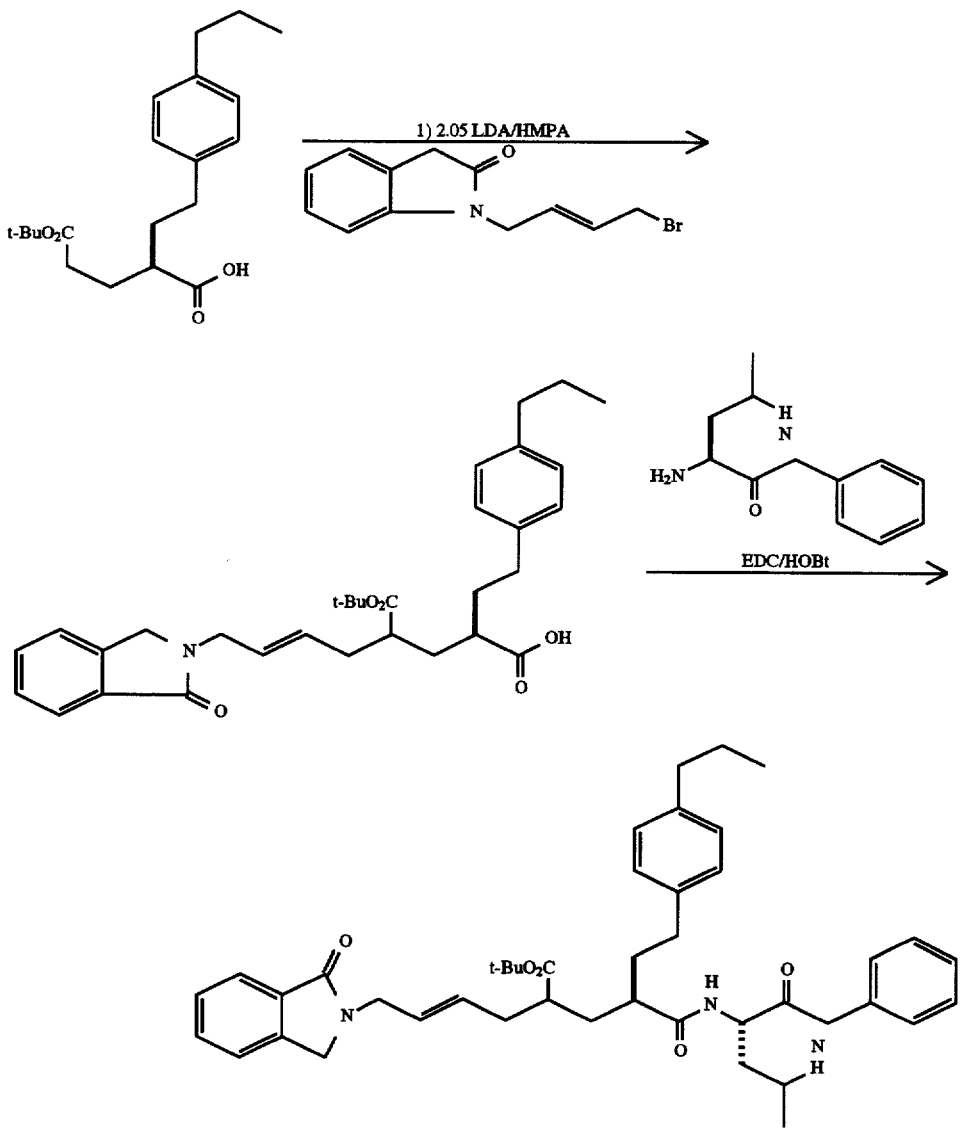

5-tert-Butyl ester 2(R)-(2-(4-(1-n-propyl)phenyl)ethyl)-4-(1-(4-(N-(2-Oxoisoindolinyl))-but-2-enyl))-1,5-pentanedioic acid 1-(L-leucine, N-phenylamide)amide: To a solution of lithium diisopropyl amide (10.47 mmol) in 10 mL of THF at −78° C. was added a solution of 5-tert-butyl ester 2(R)-(2-(4-(1-n-propyl)phenyl)ethyl)-1,5-pentanedioic acid (1.59 g, 4.76 mmol) in 2.5 mL of THF and 2.5 mL of HMPA. After 30 min at −78° C., a solution of 4-(N-(2-Oxoisoindolinyl))-1-bromo-2-butene (1.39 g, 5.24 mmol) was added and the mixture stirred for three hours. The reaction was quenched with 1:1 acetic acid: THF, diluted with ethyl acetate, and washed five times with dilute hydrochloric acid. The mixture was dried over magnesium sulfate and concentrated in vacuo to give a pale-brown oil. The mixture was purified by MPLC on silica-gel (45×350 mm column, eluting with a gradient of dichloromethane to 2% formic acid and 8% methanol in dichloromethane) to give a pale yellow oil. The mixture was then diluted with 3:1 hexane:ether, washed with sodium bicarbonate, dried over magnesium sulfate, and adsorbed onto a 70×100 mm pad of silica-gel. The gel was washed with 1:1 ethyl acetate in hexane (discarded), and eluted with 1% acetic acid and 10% methanol in toluene. This mixture was concentrated in vacuo to give the alkylation product as a pale-yellow glass. This acid, L-leucine, phenylamide (1.47 g, 7.14 mmol), and HOBt (1.29 g, 9.52 mmol) were disolved in 15 mL of DMF and cooled to –0° C. EDC (1.37 g, 7.14 mmol) was added and after 30 min at 0° C., and 2 h at ambient temperature, the mixture was diluted with ethyl acetate and washed three times with dilute hydrochloric acid and three times with dilute sodium bicarbonate. The mixture was dried over sodium sulfate, filtered, and concentrated in vacuo. The product was purified by MPLC on silica-gel (45×350 mm column, eluting with 1:1 ethyl acetate in hexane) to afford a 1:1 mixture of diastereomers which was separated by MPLC (Two Merck Lobar-B columns, eluting with 30% ethyl acetate in hexane) to give 432 mg of the title compounds as a colorless foam: Diastereomer A: 400 MHz $^1$H NMR (CD$_3$OD) δ 7.75 (d, 1H, J=7.61 Hz), 7.6–7.45 (m, 5H), 7.28 (t, 2H, J=7.47 Hz), 7.07 (t, 1H, J=7.37 Hz), 6.99 (s, 4H), 5.57 (m, 2H), 4.58 (dd, 1H, J=4.98, 9.87 Hz), 4.43 (s, 2H), 4.17 (m, 2H), 2.6–2.2 (m, 8H), 1.9–1.5 m, 9H), 1.33 (s, 9H), 0.95 (d, 3H, J=6.64 Hz), 0.93 (d, 3H, J=6.82 Hz), 0.89 (t, 3H, J=7.38 Hz). Diastereomer B: 400 MHz $^1$H NMR (CD$_3$OD) δ 7.75 (d, 1H, J=7.61 Hz), 7.6–7.4 (m, 5H), 7.29 (t, 2H, J=7.47 Hz), 7.08 (t, 1H, J=7.42 Hz), 7.01 (s, 4H), 5.56 (m, 2H), 4.59 (dd, 1H, J=5.12, 10.23 Hz), 4.44 (s, 2H), 4.17 (m, 2H), 2.6–2.1 (m, 8H), 1.9–1.5 (m, 9H), 1.34 (s, 9H), 0.96 (d, 3H, J=6.50 Hz), 0.93 (d, 3H, J=6.50 Hz), 0.90 (t, 3H, J=7.33 Hz).

Step C leucine, N-phenylamide)amide: To a solution of 5-tert-butyl ester 2(R)-(2-(4-(1-n-propyl)phenyl)ethyl)-4-(1-(4-(N-(2-Oxoisoindolinyl))-but-2-enyl))-1,5-pentanedioic acid 1-(L-leucine, N-phenylamide)amide (diastereomer A) in 5 mL of ethyl acetate was added catalytic Pd(OH)$_2$/C. After 15 min under 1 atmosphere of hydrogen, the mixture was filtered and concentrated in vacuo to give a colorless solid: 400 MHz $^1$H NMR (CD$_3$OD) δ 7.77 (d, 1H, J=6.74 Hz), 7.6–7.4 (m, 5H), 7.28 (t, 2H, J=7.56 Hz), 7.08 (t, 1H, J=7.43 Hz), 7.00 (s, 4H), 4.58 (dd, 1H, J=5.02, 9.82 Hz), 4.48 (s, 2H), 3.63 (t, 2H, J=6.73 Hz), 2.6–2.1 (m, 6H), 1.9–1.2 (m, 15H), 1.33 (s, 9H), 0.95 (d, 3H, J=6.32 Hz), 0.94 (d, 3H, J=6.27 Hz), 0.89 (t, 3H, J=7.28 Hz). The above procedure was repeated for diastereomer B to give a colorless solid: 400 MHz $^1$H NMR (CD$_3$OD) δ 7.77 (d, 1H, J=6.60 Hz), 7.6–7.4 (m, 5H), 7.28 (t, 2H, J=5.53 Hz), 7.07 (t, 1H, J=6.22 Hz), 7.01 (s, 4H), 4.60 (dd, 1H, J=5.11, 10.19 Hz), 4.46 (s, 2H), 3.60 (t, 2H, J=7.06 Hz), 2.6–2.4 (m, 4H), 2.27 (m, 1H), 2.17 (m, 1H), 1.9–1.2 (m, 15H), 1.34 (s, 9H), 0.96 (d, 3H, J=6.45 Hz), 0.93 (d, 3H, J=6.45 Hz), 0.89 (t, 3H, J=7.29 Hz). Diastereomer A was then disolved in dichloromethane and an equal portion of TFA was added. After 30 min, the mixture was concentrated in vacuo, diluted with toluene, and concentrated in vacuo to afford the title compound as a colorless solid: 400 MHz $^1$H NMR (CD$_3$OD) δ 7.77 (d, 1H, J=7.65 Hz), 7.6–7.4 (m, 5H), 7.28 (t, 2H, J=7.51 Hz), 7.08 (t, 1H, J=7.42 Hz), 6.99 (s, 4H), 4.58 (dd, 1H, J=5.21, 9.82 Hz), 4.49 (s, 2H), 3.62 (dt, 2H, J=1.85,7.05 Hz), 2.6–2.2 (m, 6H), 2.0–1.2 (m, 15H), 0.94 (d, 3H, J=6.27 Hz), 0.93 (d, 3H, J=6.27 Hz), 0.89 (t, 3H, J=7.14 Hz). The above procedure was again applied to diastereomer B to afford the title compound as a colorless solid: 400 MHz $^1$H NMR (CD$_3$OD) δ 7.75 (d, 1H, J=7.61 Hz), 7.6–7.4 (m,

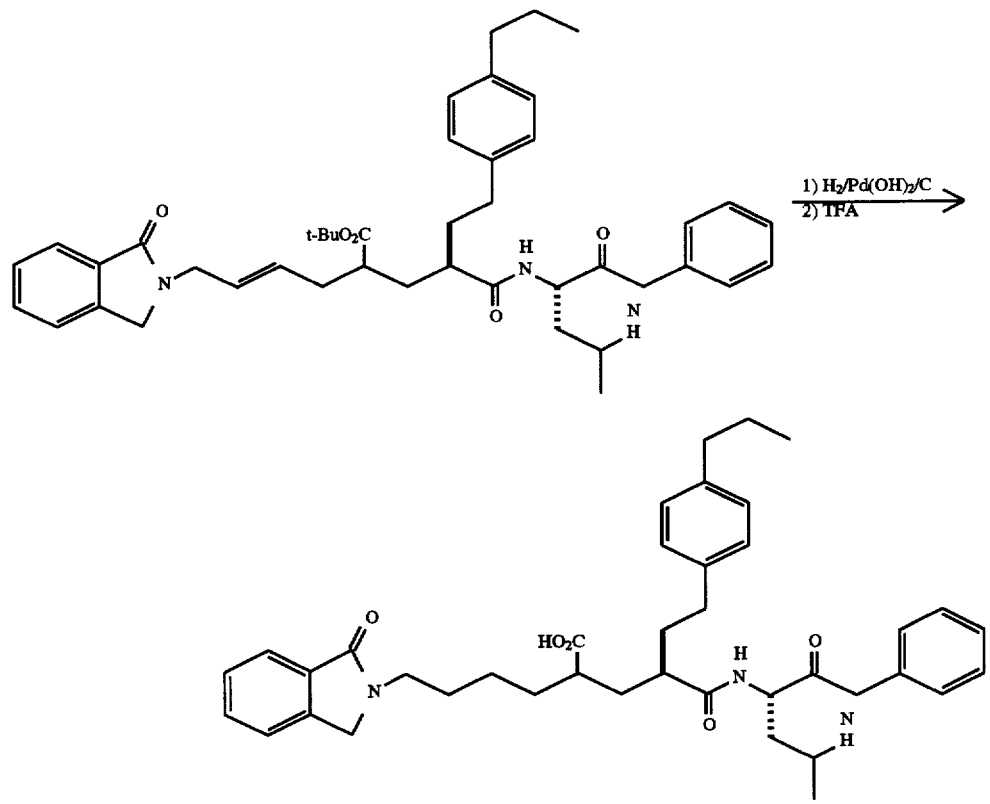

2(R)-(2-(4-(1-n-Propyl)phenyl)ethyl)-4-(1-(4-(N-(2-Oxoisoindolinyl))-butyl))-1,5-pentanedioic acid 1-(L-

5H), 7.27 (t, 2H, J=5.62 Hz), 7.06 (t, 1H, J=6.31 Hz), 6.99 (s, 4H), 4.56 (dd, 1H, J=5.07, 10.33 Hz), 4.48 (s, 2H), 3.60

(t, 2H, J=7.06 Hz), 2.6–2.2 (m, 6H), 1.9–1.2 (m, 15H), 0.96 (d, 3H, J=6.55 Hz), 0.93 (d, 3H, J=6.55 Hz), 0.89 (t, 3H, J=7.38 Hz).

EXAMPLE 5

2(R)-(2-(4-(1-n-Propyl)phenyl)ethyl)-4-(1-(4-(N-(2-Oxoisoindolinyl))-but-2-enyl))-1,5-pentanedioic acid 1-(L-leucine, N-phenylamide) amide Step A 2(R)-(2-(4-(1-n-Propyl)phenyl)ethyl)-4-(1-(4-(N-(2-Oxoisoindolinyl))-but-2-enyl))-1,5-pentanedioic acid 1-(L-leucine,N-phenylamide)amide: To a solution of 5-tert-butyl ester 2(R)-(2-(4-(1-n-propyl)phenyl)ethyl)-4-(1-(4-(N-(2-Oxoisoindolinyl))-but-2-enyl))-1,5-pentanedioic acid 1-(L-leucine, N-phenylamide)amide (diastereomer A) in dichloromethane was added an equal volume of TFA. After 60 min, the mixture was concentrated in vacuo, diluted with toluene, and concentrated in vacuo to give the title compound as a colorless solid: 400 MHz $^1$H NMR (CD$_3$OD) δ 7.75 (d, 1H, J=7.65 Hz), 7.6–7.4 (m, 5H), 7.28 (t, 2H, J=7.46 Hz), 7.07 (t, 1H, J=7.42 Hz), 6.98 (s, 4H), 5.67 (m, 1H), 5.56 (m, 1H), 4.57 (dd, 1H, J=5.12, 9.78 Hz), 4.42 (s, 2H), 4.17 (m, 2H), 2.6–2.3 (m, 8H), 2.0–1.5 (m, 9H), 0.95 (d, 3H, J=6.36 Hz), 0.93 (d, 3H, J=6.46 Hz), 0.89 (t, 3H, J=7.33 Hz).

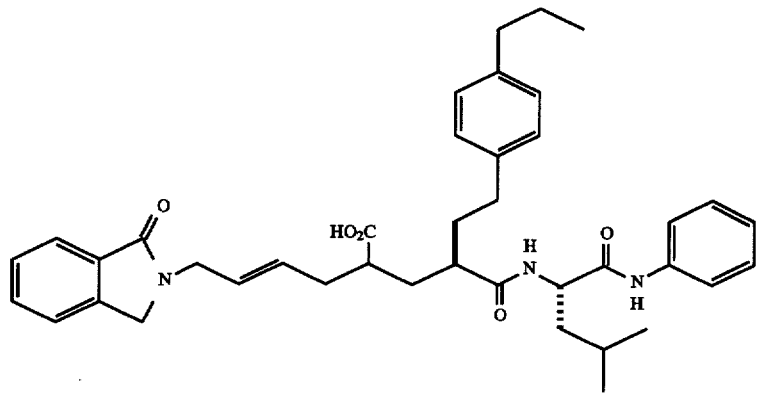

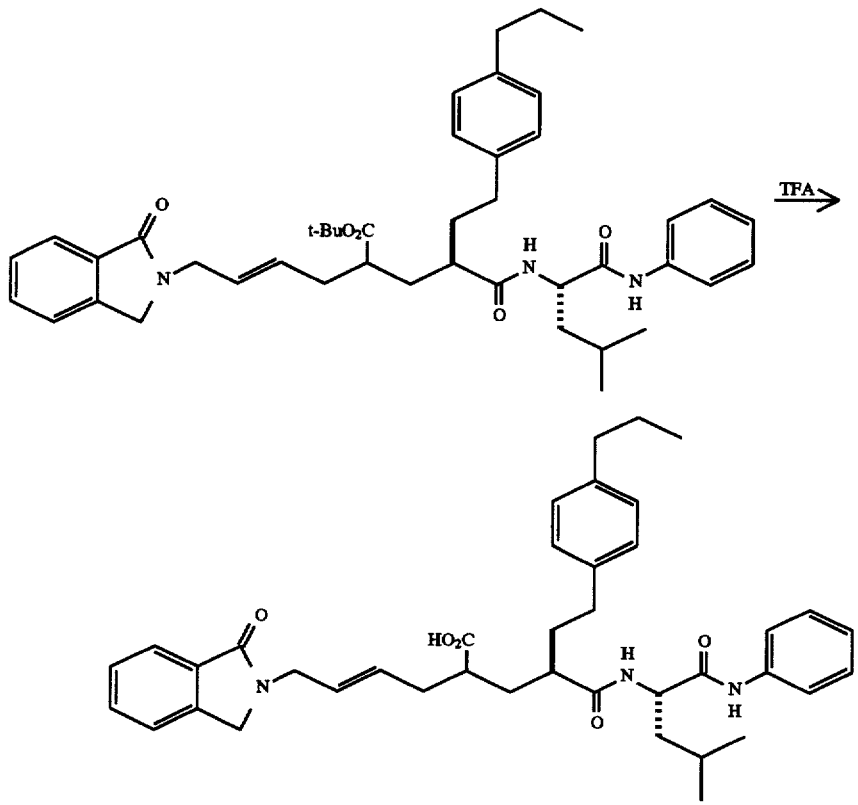

The above procedure was repeated for 2(R)-(2-(4-(1-Propyl)-phenyl)-ethyl)-4-(1-(4-(N-(2-Oxoisoindolinyl))-but-2-enyl))-pentanedioic acid 1-(S-leucine phenylamide) amide 5-tert-ester (diastereomer B) to afford the title compound as a colorless solid: 400 MHz $^1$H NMR (CD$_3$OD) δ 7.75 (d, 1H, J=7.64 Hz), 7.6–7.4 (m, 5H), 7.28 (t, 2H, J=7.52 Hz), 7.07 (t, 1H, J=7.43 Hz), 7.00 (s, 4H), 5.66 (m, 1H), 5.55 (m, 1H), 4.55 (dd, 1H, J=5.21, 10.32 Hz), 4.45 (s, 2H), 4.17 (d, 2H, J=6.13 Hz), 2.6–2.1 (m, 8H), 1.9–1.5 (m, 9H), 0.96 (d, 3H, J=6.54 Hz), 0.92 (d, 3H, J=6.69 Hz), 0.90 (t, 3H, J=7.38 Hz).

EXAMPLE 6

2(R)-(2-(4-(4-fluorophenyl)phenyl)ethyl)-4-methyl-1,5-pentanedioic acid 1-(L-leucine, N-phenylamide) amide

Step A 5-tert-Butyl 2(R)-(2-(4-(iodo)phenyl)ethyl)-4-methyl-1,5-pentanedioic acid 1-(L-leucine, N-phenylamide)amide: To a solution of 5-tert-butyl 2(R)-(2-(4-(iodo)phenyl)ethyl)-4-methyl-1,5-pentanedioic acid [prepared according to the method outlined in Scheme A where aryl is 4-iodophenyl and $R_1$ is $CH_3$ and described in detail in Example 1] (875 mg, 2.02 mmol), leucine phenyl amide (501 mg, 2.43 mmol), hydroxybenzotriazole (328 mg, 2.43 mmol) in 5 mL of THF at 25° was added ethyl dimethylaminopropyl carbodiimide (EDC) (776 mg, 4.05 mmol). The mixture was stirred overnight at room temperature. The mixture was diluted with ethyl acetate and washed successively with saturated sodium bicarbonate solution, water, and saturated sodium chloride solution. The organics were then dried over magnesium sulfate, filtered, and concentrated in vacuo. The product was purified by MPLC on silica-gel (40×350 mm column, eluting with 15% ethyl acetate in hexane) to afford 900 mg of the amide as a colorless solid (~2:1 mixture of diastereomers).

Step B 5-tert-Butyl 2(R)-(2-(4-(4-fluorophenyl)phenyl)ethyl)-4-methyl-1,5-pentanedioic acid 1-(L-leucine, N-phenylamide) amide: To a solution of 5-tert-butyl 2(R)-(2-(4-(iodo)phenyl)ethyl)-4-methyl-1,5-pentanedioic acid 1-(L-leucine, N-phenylamide)amide (100 mg, 0.16 mmol), 2.0M sodium carbonate (206 mL, 0.41 mmol), 4-fluorobenzeneboronic acid (25 mg, 0.18 mmol) in 2 mL of toluene and 1 mL of ethanol at 25° was added tetrakis(triphenylphosphine)palladium(0) (10 mg, 0.008 mmol). The mixture was stirred for 6 hours at 95°. After cooling to room temperature, the mixture was diluted with ethyl acetate and washed five times with 2N HCl. The organics were then dried over magnesium sulfate, filtered, and concentrated in vacuo. The product was purified by MPLC on silica-gel (21×300 mm column, eluting with 15% ethyl acetate in hexane) to afford ~40 mg of the biaryl as a colorless solid (~2:1 mixture of diastereomers).

Step C

2(R)-(2-(4-(4-fluorophenyl)phenyl)ethyl)-4-methyl-1,5-pentanedioic acid 1-(L-leucine, N-phenylamide)amide: To a solution of 5-tert-butyl 2(R)-(2-(4-(4-fluorophenyl)phenyl)ethyl)-4-methyl-1,5-pentanedioic acid 1-(L-leucine, N-phenylamide)amide (~40 mg) in 1 mL of methylene chloride at 0° was added ~0.5 mL trifluoroacetic acid. The mixture was allowed to warm to room temperature and stirred for 6 hours. The mixture was diluted with toluene and concentrated in vacuo. The product was purified by MPLC on silica-gel (21×100 mm column, eluting a gradient from 0 to 5% (5% acetic acid in methanol) in methylene chloride to afford 35 mg of the acid as a colorless solid (~2:1 mixture of diastereomers): MS: m/z 533.0 (M+1); (2:1 mixture of diastereomers): 400 MHz $^1$H NMR: ($CDCl_3$) δ 9.22 (s, 1 H), 7.42 (m, 4 H), 7.33 (d, 2 H, J=8 Hz), 7.08 (m, 7 H), 6.93 (t, 1 H, J=7 Hz), 4.65 (m, 1 H), 2.64 (m, 1 H), 2.49 (m, 2 H), 2.37 (m, 1 H), 2.12 (m, 1 H), 1.96 (m, 1 H), 1.76 (m, 3 H), 1.64 (m, 1 H), 1.53 (m, 1 H), 1.20 (d, 3 H, J=7 Hz), 1.02 (d, 3 H, J=7 Hz), 0.94 (d, 3 H, J=6 Hz).

The following additional compounds were prepared according to the method of Example 6.

2(R)-(2-(4-(phenyl)phenyl)ethyl)-4-methyl-1,5-pentanedioic acid 1-(L-leucine, N-phenylamide)amide: MS: m/z 515.1 (M+1); (2:1 mixture of diastereomers): 400 MHz $^1$H NMR: ($CD_3OD$) δ 7.54 (d, 2 H, J=8 Hz), 7.52 (m, 2 H), 7.45 (d, 2 H, J=8 Hz), 7.39 (t, 2 H, J=8 Hz), 7.29 (m, 3 H), 7.20 (d, 2 H, J=7 Hz), 7.08 (dd, 1 H, J=7 Hz), 4.58 (m, 1 H), 2.62 (t, 1 H, J=6 Hz), 2.49 (m, 1 H), 2.39 (m, 1 H), 2.03 (m, 1 H), 1.90–1.49 (m, 7 H), 1.17 (d, 3 H), 0.99 (dd, 6 H).

2(R)-(2-(4-(4-methoxyphenyl)phenyl)ethyl)-4-methyl-1,5-pentanedioic acid 1-(L-leucine phenylamide)amide: MS: m/z 545.2 (M+1); (2:1 mixture of diastereomers): 400 MHz $^1$H NMR: ($CDCl_3$) δ 9.39 (s, 1 H), 7.40 (dd, 4 H, J=8 Hz), 7.31 (dd, 2 H, J=8 Hz), 7.21 (m, 1 H), 7.05 (m, 3 H), 6.99 (m, 1 H), 6.89 (m, 3 H), 4.70 (m, 1 H), 3.81 (s, 3 H), 2.62 (m, 1 H), 2.49 (m, 3 H), 2.11 (m, 1 H), 1.90 (m, 2 H), 1.76 (m, 2 H), 1.68 (m, 1 H), 1.56 (m, 1 H), 1.21 (d, 3 H, J=7 Hz), 1.01 (d, 3 H, J=7 Hz), 0.94 (d, 3 H, J=6 Hz).

2(R)-(2-(4-(4-methylphenyl)phenyl)ethyl)-4-methyl-1,5-pentanedioic acid 1-(L-leucine phenylamide)amide: MS: m/z 529.2 (M+1); (2:1 mixture of diastereomers): 400 MHz $^1$H NMR: ($CDCl_3$) δ 9.20 (m, 1 H), 7.39 (m, 4 H), 7.18 (m, 3 H), 7.10 (m, 4 H), 7.01 (m, 1 H), 6.93 (m, 1 H), 6.85 (m, 1 H), 4.64 (m, 1 H), 2.62 (m, 1 H), 2.46 (m, 2 H), 2.36 (s, 3 H), 2.10 (m, 1 H), 1.95 (m, 1 H), 1.73 (m, 3 H), 1.63 (m, 2 H), 1.56 (m, 1 H), 1.21 (d, 3 H, J=7 Hz), 1.00 (d, 3 H, J=7 Hz), 0.93 (d, 3 H, J=6 Hz).

EXAMPLE 7

2(R)-(2-(4-(4-hydroxy-n-butyl)-phenyl)-ethyl)-4-methylpentanedioic acid 1-(S-leucine phenylamide) amide

Step A 5-tert-Butyl 2(R)-(2-(4-(4-hydroxy-n-butynyl)phenyl)ethyl)-4-methyl-1,5-pentanedioic acid 1-(L-leucine, N-phenylamide)amide: To a solution of 5-tert-butyl 2(R)-(2-(4-(iodo)phenyl)ethyl)-4-methyl-1,5-pentanedioic acid 1-(L-leucine, N-phenylamide)amide [prepared according to the method outlined in Scheme A where aryl is 4-iodophenyl and $R_1$ is $CH_3$ and described in detail in Example 6] (104 mg, 0.17 mmol), copper(I) iodide (2 mg), 3-butyn-1-ol (19 μL, 0.26 mmol) in 1 mL of DMF and 1 mL of diisopropylamine at 25° was added bis(triphenylphosphine)palladium (II)acetate (7 mg, 0.009 mmol). The mixture was stirred overnight at room temperature. The mixture was diluted with ethyl acetate and washed five times with 2N HCl, and once each with water and saturated sodium chloride The organics were then dried over magnesium sulfate, filtered, and concentrated in vacuo. The product was purified by MPLC on silica-gel (21×300 mm column, eluting with 35% ethyl acetate in hexane) to afford 85 mg of the alkyne as a tan solid (~2:1 mixture of diastereomers).

Step B 5-tert-Butyl 2(R)-(2-(4-(4-hydroxy-n-butyl)phenyl)ethyl)-4-methyl-1,5-pentanedioic acid 1-(L-leucine, N-phenylamide)amide: To a solution of 5-tert-butyl 2(R)-(2-(4-(4-hydroxy-n-butynyl)phenyl)ethyl)-4-methyl-1,5-pentanedioic acid 1-(L-leucine, N-phenylamide)amide (85 mg), 10% palladium on carbon (10 mg) in 1 mL of MeOH at 25° was added hydrogen gas by balloon. The mixture was stirred overnight at room temperature. The mixture was filtered through a 0.45 micron nylon filter with EtOAc to remove the catalyst, then concentrated in vacuo to afford 95 mg of the alkane as a colorless oil (~2:1 mixture of diastereomers).

Step C

2(R)-(2-(4-(4-hydroxy-n-butyl)phenyl)ethyl)-4-methyl-1,5-pentanedioic acid 1-(L-leucine, N-phenylamide)amide: To a solution of 5-tert-butyl 2(R)-(2-(4-(4-hydroxy-n-butyl)phenyl)ethyl)-4-methyl-1,5-pentanedioic acid 1-(L-leucine, N-phenylamide)amide (95 mg) in 2 mL of methylene chloride at 0° was added ~0.5 mL trifluoroacetic acid. The mixture was allowed to warm to room temperature and stirred for 6 hours. The mixture was diluted with toluene and concentrated in vacuo. The product was purified by MPLC on silica-gel (21×100 mm column, eluting a gradient from 0 to 5% (5% acetic acid in methanol) in methylene chloride to afford 75 mg of the product as a colorless solid (~2:1 mixture of diastereomers): mass spectrum: m/z 514.2 (M+3); (2:1 mixture of diastereomers): 400 MHz $^1$H NMR: (CD$_3$OD) δ 7.55 (d, 2 H, J=8 Hz), 7.29 (dd, 1 H, J=8 Hz), 7.08 (dd, 1 H, J=7 Hz), 7.03 (s, 5 H), 4.58 (m, 1 H), 4.36 (t, 3 H, J=6 Hz), 2.56 (m, 4 H), 2.46 (m, 1 H), 2.36 (m, 1 H), 2.00 (m, 1 H), 1.83–1.57 (m, 9 H), 1.15 (d, 3 H, J=7 Hz), 0.99 (dd, 6 H).

The following additional compound was prepared according to the method of Example 7.

2(R),4(S)-(2-(4-(3-hydroxy-n-propyl)phenyl)ethyl)-4-methyl-1,5-pentanedioic acid 1-(L-leucine, N-phenylamide)amide: MS: m/z 500.0 (M+3); (2:1 mixture of diastereomers): 400 MHz $^1$H NMR: (CD$_3$OD) δ 8.33 (d, 1 H, J=8 Hz), 7.55 (d, 2 H, J=8 Hz), 7.29 (dd, 2 H, J=8 Hz), 7.08 (dd, 1 H, J=7 Hz), 7.04 (s, 5 H), 4.59 (m, 1 H), 4.33 (t, 2 H, J=6 Hz), 2.64 (t, 2 H, J=7 Hz), 2.55 (m, 2 H), 2.47 (m, 1 H), 2.38 (m, 1 H), 2.00 (m, 3 H), 1.81 (m, 1 H), 1.73 (m, 2 H), 1.61 (m, 1 H), 1.50 (m, 1 H), 1.16 (d, 3 H, J=7 Hz), 0.99 (dd, 6 H, J=6 Hz).

EXAMPLE 8

2(R)-(2-phenylethyl)-4-methyl-1,5-pentanedioic acid 1-(L-leucine, N-phenylamide)amide

Step A 5-tert-Butyl 2(R)-(2-phenylethyl)-4-methyl-1,5-pentanedioic acid 1-(L-leucine, N-phenylamide)amide: To a solution of 5-tert-butyl 2(R)-(2-(4-(iodo)phenyl)ethyl)-4-methyl-1,5-pentanedioic acid 1-(L-leucine, N-phenylamide)amide (100 mg, 0.16 mmol), 20% Pd(OH)$_2$ on carbon (10 mg) in 1 mL of MeOH with three drops of acetic acid at 25° was added hydrogen gas by balloon. The mixture was stirred overnight at room temperature. The mixture was filtered through a 60 mL fritted funnel filled with silica gel with EtOAc to remove the catalyst, then concentrated in vacuo to afford ~50 mg of the ester as a yellowish oil.

Step B

2(R)-(2-phenylethyl)-4-methyl-1,5-pentanedioic acid 1-(L-leucine, N-phenylamide)amide: To a solution of 5-tert-butyl 2(R)-(2-phenylethyl)-4-methyl-1,5-pentanedioic acid 1-(L-leucine, N-phenylamide)amide (~50 mg), in 1 mL of methylene chloride at 0° was added ~0.5 mL trifluoroacetic acid. The mixture was allowed to warm to room temperature and stirred for 16 hours. The mixture was diluted with toluene and concentrated in vacuo. The product was purified by MPLC on silica-gel (21×100 mm column, eluting a gradient from 0 to 5% (5% acetic acid in methanol) in methylene chloride to afford 45 mg of the acid as a colorless solid (~2:1 mixture of diastereomers): MS: m/z 439.2 (M+1); (2:1 mixture of diastereomers): 400 MHz $^1$H NMR: (CDCl$_3$) δ 9.25 (s, 1 H), 7.39 (d, 2 H, J=8 Hz), 7.20–7.05 (m, 6 H), 6.99–6.87 (m, 2 H), 4.65 (m, 1 H), 2.61 (m, 1 H), 2.46 (m, 2 H), 2.33 (m, 1 H), 2.10 (m, 1 H), 1.94 (m, 1 H), 1.75 (m, 4 H), 1.63 (m, 1 H), 1.52 (m, 1 H), 1.19 (d, 3 H, J=7 Hz), 1.01 (d, 3 H, J=6 Hz), 0.93 (d, 6H, J=6 Hz).

EXAMPLE 9

2(R)-(2-(4-(1-n-Propyl)phenyl)ethyl)-1,5-pentanedioic acid 1-(L-leucine, N-ethylamide)amide

Step A

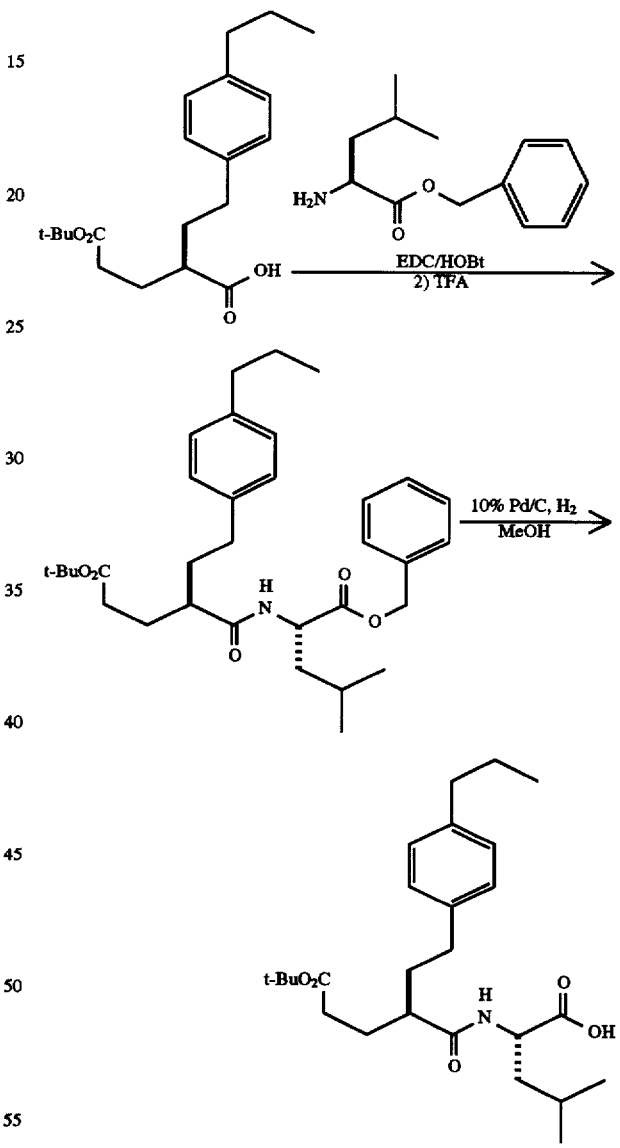

2(R)-(2-(4-(1-n-Propyl)phenyl)ethyl)pentanedioic acid 1-(L-leucine)amide: To a solution of 5-tert-butyl ester 2(R)-(2-(4-(1-n-propyl)phenyl)ethyl)-1,5-pentanedioic acid (0.67 g, 2.0 mmol), S-leucine benzyl ester (865 mg, 2.2 mmol), and hydroxybenzotriazole (HOBt) (405 mg, 3.0 mmol) in 15 mL of methylene chloride at 0° C. was added ethyl dimethylaminopropyl carbodiimide (EDC) (765 mg, 4.0 mmol). The mixture was allowed to warm slowly to ambient temperature and stirred overnight. The mixture was diluted with 10 mL of methylene chloride and washed two times with water and three times with dilute sodium bicarbonate. The organics were pooled then dried over magnesium sulfate, filtered, and concentrated in vacuo. The product was purified by MPLC on silica-gel (35×350 mm column, eluting with 10% ethyl acetate in hexane) to afford 1.16 g of the amide benzyl ester as a colorless oil: 400 MHz $^1$H NMR (CDCl$_3$) δ 7.32 (m, 5H), 7.04 (s, 5H), 5.87(br d, 1H, J=7.9 Hz), 5.15 (S,2H), 4.61 (m, 1H), 2.6–1.5 (m, 16H), 1.37(s, 9H), 0.93–0.89(m, 12H,). The tert-butyl benzyl diester was dissolved in 20 mL of dichloromethane and 55 mg of 10% palladium on carbon was added, the flask fitted with a stir bar, rubber septum and balloon reservoir filled with hydrogen. After 2 h, the mixture was filtered and rinsed through a Celite pad with methanol and concentrated in vacuo to afford the title compound as a colorless thick oil: 400 MHz $^1$H NMR (CDCl$_3$) δ 7.09–7.03 (m, 5H), 6.03 (br d, 1H, J=7.9), 4.60 (m, 1H), 2.69–2.60 (m, 1H), 2.52 (d, 1H, J=6 Hz), 2.49 (d, 1H, J=6 Hz), 2.3–1.5 (m, 13H), 1.37(s, 9H), 0.95–0.89 (m, 9H).

20% ethyl acetate in hexane) to afford 700 mg of the ethyl amide as a colorless solid: 400 MHz $^1$H NMR (CDCl$_3$) δ 8.02 (bd, 1H, J=8 Hz), d 7.09–6.9(m, 5H), 4.60 (q, 1H, J=7 Hz), 3.25 (m,2H J=7Hz),2.6–2.2 (m, 10H), 1.95–1.55 (m, 10H), 1.10(s, 3H, J=8.5 Hz), 0.95–0.89 (m, 3H) mass spectrum (M$^+$=418).

The following additional compound was prepared according to the method of Example 9.

2(R)-(2-(4-(1-n-Propyl)phenyl)ethyl)-1,5-pentanedioic acid 1-(L-leucine, N-isopropylamide)amide: MS (M$^+$=432); 400 MHz $^1$H NMR (CDCl$_3$) δ 7.03–6.96 (m,4H), 4.45 (m, 1H), 4.0 (bm, 1H) (m,2H J=7Hz),2.55–1.55 (m, 16H), 1.13(dd, 6H, J=11Hz, J=6Hz), 0.95–0.89 (m, 9H).

EXAMPLE 10

2(R)-(2-(4-(1-n-Propyl)phenyl)propyl)-1,5-pentanedioic acid 1-(2(S)-tert-butyl-glycine, N-(4-pyridyl)amide)amide Step B Step A

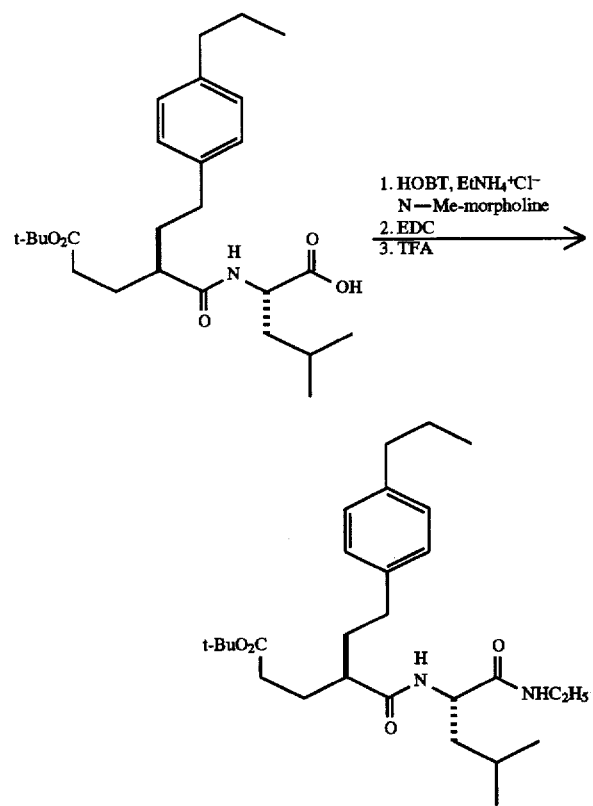

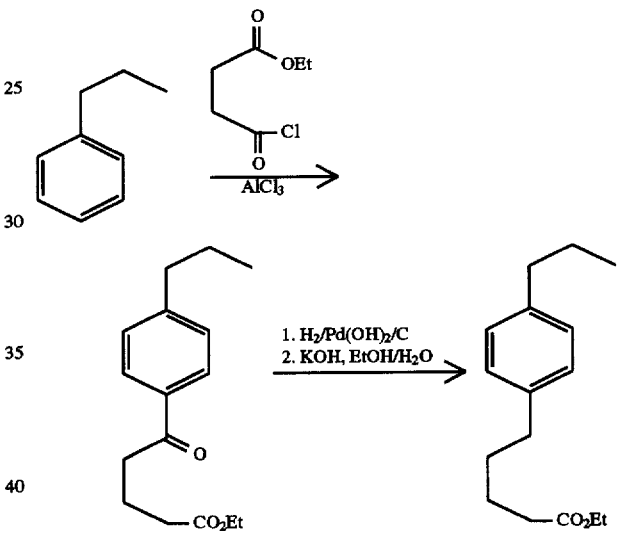

2(R)-(2-(4-(1-n-Propyl)phenyl)ethyl)-1,5-pentanedioic acid 1-(L-leucine, N-ethylamide)amide: To a solution of 2(R)-(2-(4-(1-n-propyl)phenyl)ethyl)pentanedioic acid 1-(L-leucine)amide (0.100 g, 0.22 mmol), ethylamine hydrochloride (30 mg, 0.45 mmol), and hydroxybenzotriazole (HOBt) (45 mg, 0.33 mmol) in 5 mL of methylene chloride at 0° C. was added ethyl dimethylaminopropyl carbodiimide (EDC) (85 mg, 0.45 mmol). The mixture was allowed to warm slowly to ambient temperature and stirred overnight. The mixture was diluted with 5 mL of methylene chloride and washed two times with 2 mL 2N hydrochloric acid water and two times with dilute sodium bicarbonate. The organic layer was then dried over magnesium sulfate, filtered, and concentrated in vacuo. The product was purified by MPLC on silica-gel (15×350 mm column, eluting with 5-(4-(1-n-Propyl)phenyl)pentanoic acid. To a solution of propylbenzene (24.0 mmol, 200 mmole) in 200 mL of methylene chloride cooled to 0° was added 4-chloroformyl butyric acid, ethyl ester (33.0 g, 186 mmol). Aluminum chloride (29.4 g, 220 mmol) was added portionwise over 30 minutes (15°±5). Warm to room temperature for 1 hr, then reflux gently for 3 hrs. The reaction was quenched with 2N hydrochloric acid, diluted with ether and washed 5 times with dilute hydrochloric acid. The organics were then extracted three times with dilute sodium hydroxide and the combined aqueous layers washed three times with ether. The aqueous layer was then acidified with concentrated hydrochloric acid and extracted twice with ether. The combined ether layer was washed with brine, dried over magnesium sulfate, filtered and concentrated in vacuo to give 12.3 g of a viscous oil which was chromatographed on silica gel (87/13 hexane/ethyl acetate) to give 10.3 g of pure product. The product (7 g, 27 mmol) was dissolved in 50 mL of acetic acid and ~250 mg of Pearlman's catalyst was added. The mixture was stirred vigorously under 1 atmosphere of hydrogen for 16 h, filtered through a pad of celite and concentrated in vacuo. The product was diluted with toluene and concentrated in vacuo to remove the remaining acetic acid to afford 5.8 g of the title compound ethyl ester as an oil: 400 MHz $^1$H NMR (CDCl$_3$) 7.06 (s, 4H), 4.09 (q, 2H, J=7Hz), 2.6–2.5

(m, 4H), 2.32–2.28 (t, 2H, J=8 H z), 1.7–1.6 (m, 4H), 1.23 (t, 3H, J=7Hz), 0.91 (t, 3H, J=7Hz). The ethyl ester was removed by hydrolysis in 3/1 ethanol/water by stirring with 3 equivalents of potassium hydroxide over 24 hr. The solution was acidified with concentrated HCl and the solvent removed under reduced pressure. The reaction mixure was redissolved in water and the product extracted with ether. The ether layer was dried over MgSO$_4$, filtered and the solvent removedunder reduced pressure to yield 4.9 g of product.

Employing the methodology described in Example 1, 5-(4-(1-n-propyl)phenyl)-1-pentanoic acid was converted to 5-tert-butyl ester 2(R)-(3-(4-(1-propyl)phenyl)propyl)-1,5-pentanedioic acid.

Step B

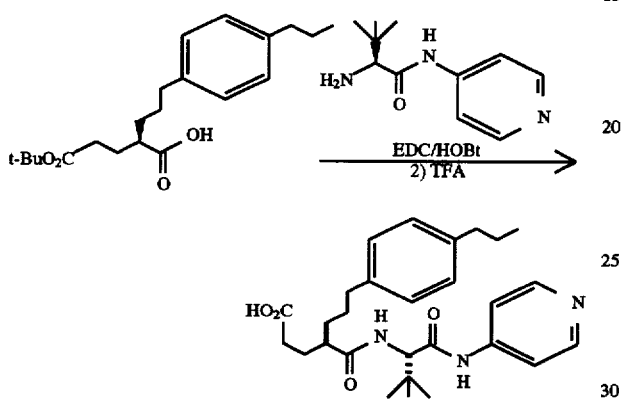

2(R)-(3-(4-(1-n-Propyl)phenyl)propyl)-1,5-pentanedioic acid 1-((2(S)-tert-butyl)glycine, N-(4-pyridyl)amide)amide: To a solution of 5-tert-butyl ester 2(R)-(3-(4-(1-propyl) phenyl)propyl)-1,5-pentanedioic acid (51 mg, 0.145 mmol), 2(S)-tert-butylglycine-(4-pyridyl)amide (25 mg, 0.12 mmol), hydroxybenzotriazole (HOBt) (24 mg, 0.18 mmol), and N-methylmorpholine (NMM) (40 µL, 0.86 mmol), in 800 µL of dichloromethane at 0° C. was added ethyl dimethylaminopropyl carbodiimide (EDC) (46 mg, 0.24 mmol). The mixture was allowed to warm slowly to ambient temperature and stirred overnight. The mixture was diluted with dichloromethane and washed once times with dilute sodium bicarbonate. The organic layer was then dried over magnesium sulfate, filtered, and concentrated in vacuo. The product was purified by MPLC on silica-gel (8×300 mm column, eluting with 80% ethyl acetate in hexane) to afford 70 mg of the amide acid 5-tert-butyl ester as a colorless oil. 400 MHz $^1$H NMR (CDCl$_3$) δ 9.0 (bs), 8.36 (d, 2H, J=6 Hz), 7.38 (d, 2H, J=6 Hz), 6.94 (d, 2H, J=6Hz), 6.96 (d, 2H, J=6Hz), 6.40 (d, 1H, J=8 Hz), 4.50(d, 1H, J=7 Hz), 2.5–1.5 (m, 15H), 1.41 (s, 9H), 1.06 (s, 9H), 0.89 (t, 3H, J=7 Hz). The tert-butyl ester was hydrolyzed in trifluoroacetic acid and the acid was removed as an azeotrope with toluene under reduced pressure. 400 MHz $^1$H NMR (CDCl$_3$) δ 8.50 (bd, 2H, J=6 Hz), 8.00 (d, 2H, J=6 Hz), 6.97 (d, 4H, J=3 Hz), 4.50 (d, 1H, J=7 Hz), 2.55–1.45 (m, 15H), 1.06 (s, 9H), 0.87 (t, 3H, J=7 Hz), mass spectrum (M$^+$=481).

The following additional compound was prepared according to the method of Example 10.

2(R)-(3-(4-(1-n-Propyl)phenyl)propyl)-1,3-pentanedioic acid 1-(L-leucine, N-phenylamide)amide: 400 MHz $^1$H NMR (CDCl$_3$) δ 9.0 (bs), 7.41 (d, 2H, J=7.56 Hz), 7.18 (t, 2H, J=7.47 Hz), 7.04 (t, 1H, J=7.42 Hz), 6.94 (d, 2H, J=6Hz), 6.89 (d, 2H, J=6Hz) 4.75 (dd, 1H, J=5Hz, J=9 Hz), 2.5–2.2 (m, 9H), 1.9–1.3 (m, 9H), 0.98 (d, 3H, J=6.46 Hz), 0.98 (d, 3H, 6.55 Hz), 0.90 (t, 3H, J=7.38 Hz). Mass spec (M$^+$=480).

EXAMPLE 11

2(R)-(2-(4-(1-n-Propyl)phenyl)ethyl)-4-hexyl-1,5-pentanedioic acid 1-(L-leucine, N-phenylamide) amide

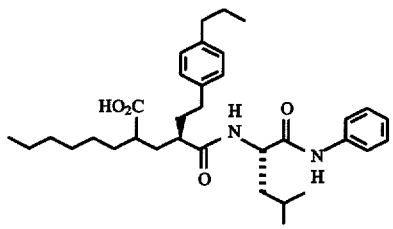

Step A

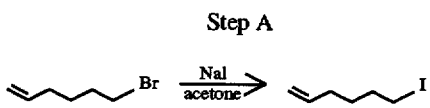

6-Iodo-1-hexene: A suspension of sodium iodide (55.00 g, 367 mmol) in acetone (50 mL) was stirred as 6-bromo-1-hexene (16.5 mL, 20.1 g, 123 mmol) was added dropwise over 30 min. The mixture was stirred at room temperature for 30 min and then heated to reflux for 3 h. After cooling to room temperature, the mixture was diluted with water (300 mL) and extracted with of ether (3×40 mL). The combined organic extracts were washed with 1N aqueous sodium bisulfite (20 mL) followed by saturated aqueous sodium chloride (40 mL). After drying over sodium sulfate, most of the ether was distilled off at atmospheric pressure. The remaining material was distilled at reduced pressure to yield 21.8 g (84% yield) of the title compound as a clear liquid, B.p. 72°–73.5° C. (18 mm Hg): 400 MHz $^1$H NMR (CDCl$_3$) δ 5.76 (ddt, 1H, J=16, 9, 6.5 Hz), 4.99 (dq, 1H, J=16, 1.5 Hz), 4.94 (dm, 1H, J=9 Hz), 3.17 (t, 2H, J=6.5 Hz), 2.06 (q, 2H, J=7 Hz), 1.82 (quintet, 2H, J=7 Hz), 1.48 (quintet, 2H, J=7 Hz).

Step B

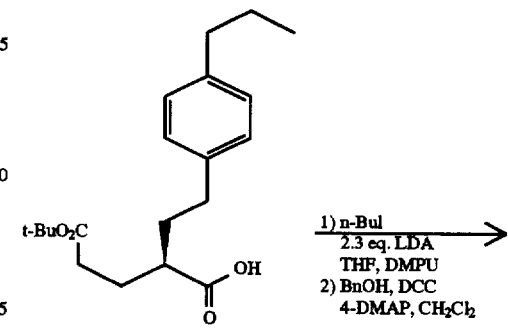

49
-continued

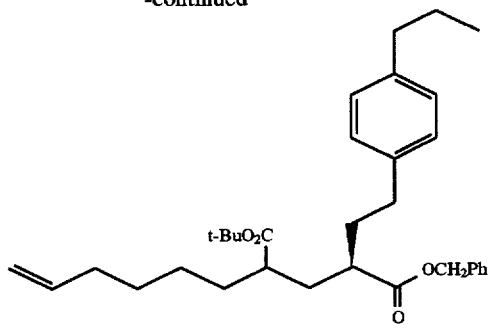

1-Benzyl ester 5-tert-butyl ester 2(R)-(2-(4-(1-n-propyl)phenyl)ethyl)-4-(5-hexen-1-yl)-1,5-pentanedioic acid: THF (2.4 mL) was cooled to about −20° C. and a cyclohexane solution of 1.5M lithium diisopropylamide mono (tetrahydrofuran) (1.52 mL, 2.30 mmol) was added. The solution was cooled to −70° C. and 5-tert-butyl ester 2(R)-(2-(4-(1-n-propyl)phenyl)ethyl)-1,5-pentanedioic acid (335 mg, 1.00 mmol) was added as a solution in THF (0.30 mL) and 1,3-dimethyl-3,4,5,6-tetrahydro-2(1H)-pyrimidinone (0.50 mL). An additional portion of THF (0.30 mL) was used to rinse the transfer needle. The solution was stirred at −70° C. for 1 h before the addition of 6-iodo-1-hexene (0.71 mL, 1.05 g, 5.00 mmol). After 3.75 h at −70° C., the mixture was allowed to warm up to room temperature over 20 min before being diluted with 0.5N aqueous hydrochloric acid (20 mL). The mixture was extracted with two portions of ethyl acetate (50 mL and 15 mL). The organic layers were extracted in succession with saturated aqueous sodium chloride (20 mL), dried (sodium sulfate), decanted, and evaporated to yield 648 mg of crude 5-tert-butyl ester 2(R)-(2-(4-(1-n-propyl)phenyl)ethyl)-4-(5-hexen-1-yl)-1,5-pentanedioic acid.

A solution of the crude carboxylic acid, benzyl alcohol (0.210 mL, 219 mg, 2.03 mmol), and 4-(dimethylamino)pyridine (24 mg, 0.20 mmol) in dichloromethane (3.0 mL) was stirred at room temperature as 1,3-dicyclohexylcarbodiimide (270 mg, 1.31 mmol) was added with additional dichlormethane (0.5 mL) to rinse. After 1 h, a few drops of water were added along with hexane (5 mL). After 10 min, the mixture was filtered and the precipitate was washed with hexane (5 mL). The filtrate was diluted with hexane (30 mL) and washed with 2N aqueous hydrochloric acid (15 mL), saturated aqueous sodium bicarbonate (15 mL), and saturated aqueous sodium chloride (15 mL). The organic layer was dried over sodium sulfate, filtered, and evaporated to yield 606 mg of yellow oil. Flash column chromatography on silica gel eluting with 4% ether in hexane gave the more polar diastereomer of 1-benzyl ester 5-tert-butyl ester 2(R)-(2-(4-(1-n-propyl)phenyl)ethyl)-4-(5-hexen-1-yl)-1,5-pentanedioic acid as 317 mg (63% yield for alkylation and esterification) of colorless oil: 400 MHz $^1$H NMR (CDCl$_3$) δ 7.37–7.27 (m, 5H), 7.04 (d, 2H, J=8 Hz), 6.98 (d, 2H, J=8 Hz), 5.74 (ddt, 1H, J=16, 10, 7 Hz), 5.10 (s, 2H), 4.95 (dq, 1H, J=16, 1.5 Hz), 4.90 (dm, 1H, J=10 Hz), 2.56–2.40 (m, 5H), 2.26–2.17 (m, 1H), 2.02–1.73 (m, 5H), 1.63–1.43 (m, 5H), 1.38 (s, 9H), 1.38–1.13 (m, 4H), 0.91 (t, 3H, J=7 Hz).

50
Step C

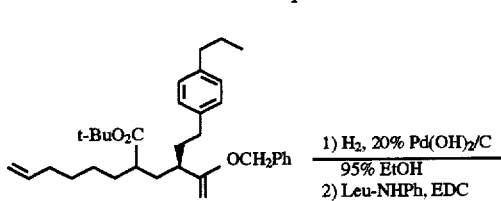

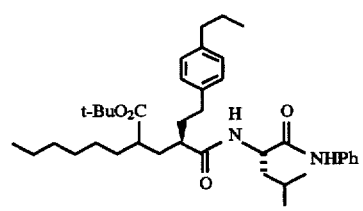

5-tert-Butyl ester 2(R)-(2-(4-(1-n-propyl)phenyl)ethyl)-4-hexyl-1,5-pentanedioic acid 1-(L-leucine, N-phenylamide) amide: 1-Benzyl ester 5-tert-butyl ester 2(R)-(2-(4-(1-n-propyl)phenyl)ethyl)-4-(5-hexen-1-yl)-1,5-pentanedioic acid (210 mg, 0.414 mmol) from the preceeding step was stirred in 95% ethanol (14 mL) containing 20% palladium hydroxide on carbon (57 mg) in a round-bottom flask connected to a hydrogen-filled balloon. After 3.5 h, the flask was purged with nitrogen and the contents were filtered through a 0.45 micron membrane. The filtrate was evaporated to give 159 mg of 5-tert-butyl ester 2(R)-(2-(4-(1-n-propyl)phenyl)ethyl)-4-hexyl-1,5-pentanedioic acid as a colorless oil (92% yield).

A solution of the crude carboxylic acid (159 mg, 0.38 mmol), 1-hydroxybenzotriazole hydrate (77 mg, 0.50 mmol), and L-leucine, N-phenylamide (90 mg, 0.44 mmol) in DMF (2.8 mL) was cooled in an ice bath and 1-(3-dimethylaminopropyl)-3-ethylcarbodiimide hydrochloride (86 mg, 0.45 mmol) was added. The mixture was stirred at 0° C. for 2.5 h with gradual warming to room temperature over another 2.5 h. The mixture was diluted with ethyl acetate (35 mL) and washed with saturated aqueous sodium bicarbonate (2×30 mL) and saturated aqueous sodium chloride (2×30 mL). The aqueous layers were extracted in succession with ethyl acetate (20 mL). The combined organic layers were dried (sodium sulfate), decanted, and evaporated to give 231 mg of white foam. Flash column chromatography on silica gel (11 g), eluting with 10% ethyl acetate/hexane (150 mL) and 15% ethyl acetate/hexane (150 mL) yielded 165 mg (71% yield) of 5-tert-butyl ester 2(R)-(2-(4-(1-n-propyl)phenyl)ethyl)-4-hexyl-1,5-pentanedioic acid 1-(L-leucine, N-phenylamide)amide as a colorless film: 400 MHz $^1$H NMR (CDCl$_3$) δ 8.58 (s, 1H), 7.50 (d, 2H, J=8 Hz), 7.25 (t, 2H, J=8 Hz), 7.05 (t, 1H, J=8 Hz), 7.00 (d, 2H, J=8 Hz), 6.92 (d, 2H, J=8 Hz), 5.93 (d, 1H, J=8 Hz), 4.53 (q, 1H, J=7 Hz), 2.54 (ddd, 1H, J=13, 9, 5 Hz), 2.49 (t, 2H, J=7 Hz), 2.37 (dt, 1H, J=13, 8 Hz), 2.28 (tt, 1H, J=8, 5 Hz), 2.11–2.03 (m, 1H0, 1.96–1.45 (m, 11H), 1.37 (s, 9H), 1.30–1.16 (m, 8H), 0.96 (d, 3H, J=6 Hz), 0.94 (d, 3H, J=6 Hz), 0.90 (t, 3H, J=7 Hz), 0.85 (t, 3H, J=7 Hz).

Step D

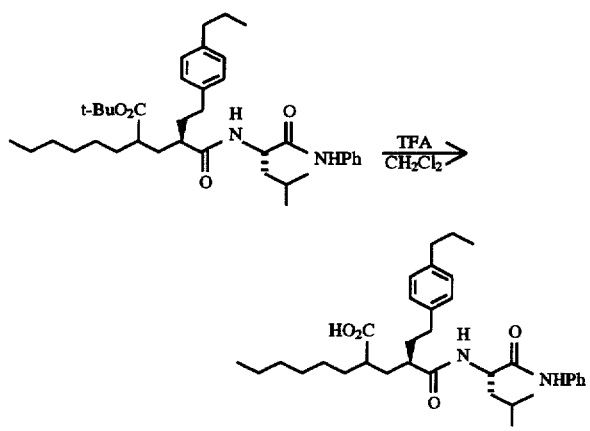

2(R)-(2-(4-(1-n-Propyl)phenyl)ethyl)-4-hexyl-1,5-pentanedioic acid 1-(L-leucine, N-phenylamide)amide: Trifluoroacetic acid (2.4 mL) was added to a 0° C. solution of 5-tert-butyl ester 2(R)-(2-(4-(1-n-propyl)phenyl)ethyl)-4-hexyl-1,5-pentanedioic acid 1-(L-leucine, N-phenylamide) amide (161 mg, 0.27 mmol) in dichloromethane (2.4 mL). The solution was stirred for 3 h at 0° C. and then 1.5 h at room temperature. Toluene was added and the solution was evaporated. This was repeated with two additional portions of toluene. The residue was dissolved in methanol and filtered through a 0.45 micron membrane. Evaporation of the filtrate gave 128 mg (88% yield) of the title compound as an off-white powder: 400 MHz $^1$H NMR (CDCl$_3$) δ 9.54 (s, 1H), 7.31 (d, 2H, J=7 Hz), 7.01 (s, 4H), 6.97 (t, 2H, J=8 Hz), 6.84 (t, 1H, J=8 Hz), 4.63 (q, 1H, J=7 Hz), 2.66–2.56 (m, 1H), 2.50 (t, 2H, J=7 Hz), 2.50–2.42 (m, 1H), 2.38–2.20 (m, 2H), 2.08 (dt, 1H, J=13, 9 Hz), 1.99–1.88 (m, 1H), 1.83–1.50 (m, 6H), 1.58 (sextet, 2H, J=7 Hz), 1.46–1.36 (m, 1H, 1.30–1.16 (m, 8H), 1.04 (d, 3H, J=6 Hz), 0.92 (d, 3H, J=6 Hz), 0.90 (t, 3H, J=7 Hz), 0.84 (t, 3H, J=7 Hz).

The following additional compounds were prepared according to the method of Example 11.

2(R)-(2-(4-(1-n-Propyl)phenyl)ethyl)-4-butyl-1,5-pentanedioic acid 1-(L-leucine, N-phenylamide)amide: 400 MHz $^1$H NMR (CDCl$_3$) δ 9.50 (s, 1H), 7.34 (d, 2H, J=7.5 Hz), 7.04 (s, 4H), 7.00 (t, 2H, J=7.5 Hz), 6.87 (t, 1H, J=7.5 Hz), 6.67 (bd, 1H, J=5 Hz), 4.64 (q, 1H, J=7.5 Hz), 2.64 (ddd, 1H, J=14, 10, 5 Hz), 2.56–2.45 (m, 3H), 2.39–2.30 (m, 1H), 2.30–2.23 (m, 1H), 2.10 (dt, 1H, J=14, 9 Hz), 2.01–1.91 (m, 2H), 1.86–1.52 (m, 8H), 1.49–1.39 (m, 1H), 1.32–1.24 (m, 4H), 1.06 (d, 3H, J=6 Hz), 0.94 (d, 3H, J=6 Hz), 0.93 (t, 3H, J=7 Hz), 0.88 (t, 3H, J=7 Hz); MS (FAB), m/e=523 [M+1].

2(R)-(2-(4-(1-n-Propyl)phenyl)ethyl)-4-(3-methylbenzyl)-1,5-pentanedioic acid 1-(L-leucine, N-phenylamide)amide (62:38 mixture of diastereomers): 400 MHz $^1$H NMR (CD$_3$OD) δ 6.9–7.6(m, 13H), 2.86–2.3(m, 8H), 2.28 (s, 3H), 2.0–1.5 (m, 9H), 0.98(2d, J=7.57 Hz), 0.90 (t, 3H, J=7.32Hz). MS (FAB-pos), m/e=571.3 [M+1].

EXAMPLE 12

2(R)-(2-(4-(1-n-Propyl)phenyl)ethyl)-4-(4-(2-benzimidazolyl)butyl)-1,5-pentanedioic acid 1-(L-leucine, N-phenylamide)amide, trifluoroacetic acid salt

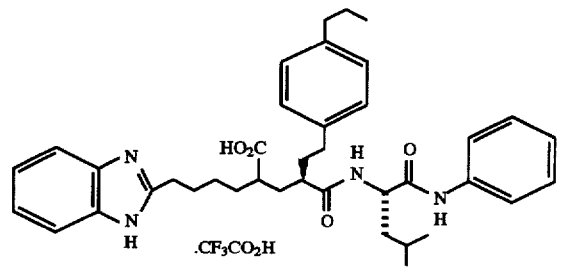

Step A

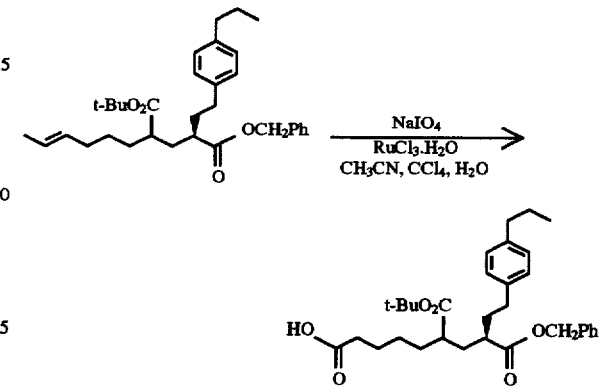

1-Benzyl ester 2(R)-(2-(4-(1-n-propyl)phenyl)ethyl)-4-(tert-butoxycarbonyl)-1,9-nonanedioic acid: Acetonitrile (7.6 mL) and water (11.4 mL) were added to a solution of 1-benzyl ester 5-tert-butyl ester 2(R)-(2-(4-(1-n-propyl)phenyl)ethyl)-4-(5-hexen-1-yl)-1,5-pentanedioic acid [from Example 11] (1.90 g, 3.75 mmol) in carbon tetrachloride (7.6 mL). Sodium periodate (1.83 g, 8.55 mmol) was added along with ruthenium trichloride hydrate (18 mg, 0.087 mmol), and the mixture was stirred at room temperature under nitrogen. The mixture was partitioned between dichloromethane (100 mL) and water (100 mL). The aqueous layer was extracted with dichloromethane (3×50 mL). The combined organic extracts were dried (magnesium sulfate), filtered, and evaporated. The residue was dissolved in ether and filtered through celite. The filtrate was evaporated to yield 2.01 g of dark oil. Flash column chromatography on silica gel (150 g) packed in hexane and eluting with 10% ethyl acetate/hexane (2 L) followed by 1% acetic acid in 10% ethyl acetate/hexane (2 L) yielded 1.47 g (74% yield) of 1-benzyl ester 2(R)-(2-(4-(1-n-propyl)phenyl)ethyl)-4-(tert-butoxycarbonyl)-1,9-nonanedioic acid as a colorless oil: 400 MHz $^1$H NMR (CDCl$_3$) δ 7.37–7.27 (m, 5H), 7.04 (d, 2H, J=8 Hz), 6.98 (d, 2H, J=8 Hz), 5.10 (s, 2H), 2.5602.40 (m, 5H), 2.28 (t, 2H, J=7 Hz), 2.25–2.17 (m, 1H), 1.99–1.84 (m, 2H), 1.82–1.72 (m, 1H), 1.64–1.46 (m, 6H), 1.43–1.35 (m, 1H), 1.37 (s, 9H), 1.30–1.19 (m, 2H), 0.90 (t, 3H, J=7 Hz).

Step B

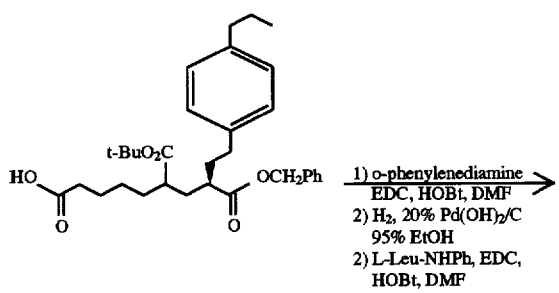

1) o-phenylenediamine
   EDC, HOBt, DMF
2) H₂, 20% Pd(OH)₂/C
   95% EtOH
2) L-Leu-NHPh, EDC,
   HOBt, DMF

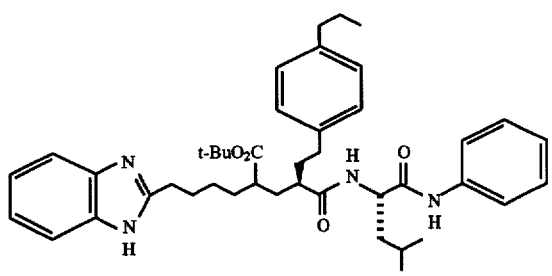

5-tert-Butyl ester 2(R)-(2-(4-(1-n-propyl)phenyl)ethyl)-4-(4-(2-benzimidazolyl)-butyl)-1,5-pentanedioic acid 1-(L-leucine, N-phenylamide)amide: 1-Hydroxybenzotriazole hydrate (136 mg, 0.89 mmol) and 1-(3-dimethylaminopropyl)-3-ethylcarbodiimide hydrochloride (146 mg, 0.76 mmol) were added to a solution of 2(R)-(2-(4-(1-n-propyl)phenyl)ethyl)-4-(tert-butoxycarbonyl)nonanedioic acid 1-benzyl ester (334 mg, 0.64 mmol) in DMF (4.6 mL). After 1.5 h, o-phenylenediamine (86 mg, 0.80 mmol) was added. After an additional 4 h, the mixture was diluted with ethyl acetate (75 mL) and washed with saturated aqueous sodium bicarbonate (2×75 mL) followed by saturated aqueous sodium chloride (2×75 mL). The aqueous layers wer extracted in succession with ethyl acetate (50 mL). The combined organic extracts were dried (sodium sulfate), decanted, and evaporated to give a brown oil which was dissolved in acetic acid (22.6 mL). The acetic acid solution was heated to 60° C. for 2.5 h, cooled to room temperature, and evaporated. The residue was dissolved in ethyl acetate (50 mL), washed with saturated aqueous sodium bicarbonate (50 mL) and saturated aqueous sodium chloride (50 mL), dried (sodium sulfate), decanted, and evaporated to yield 344 mg of crude 1-benzyl ester 5-tert-butyl ester 2(R)-(2-(4-(1-n-propyl)phenyl)ethyl)-4-(4-(2-benzimidazolyl)butyl)pentanedioic acid as an orange oil.

A portion (100 mg) of the crude product was dissolved in 95% ethanol (7.0 mL) and stirred with 20% palladium hydroxide/carbon (29.9 mg) in a round bottom flask connected to a hydrogen-filled balloon. After 40 min, the flask was purged with nitrogen and the mixture was filtered through a 0.45 micron membrane. Evaporation of the filtrate yielded 88 mg of crude 5-tert-butyl ester 2(R)-2-(2-(4-(1-n-propyl)phenyl)ethyl)-4-(4-(2-benzimidazolyl)butyl)-1,5-pentanedioic acid as pale yellow residue.

1-Hydroxybenzotriazole hydrate (32 mg, 0.21 mmol) and L-leucine, N-phenylamide (38 mg, 0.18 mmol) were added to a solution of the crude hydrogenation product (80 mg) from the preceding step in DMF (1.2 mL). The solution was cooled to 0° C. and 1-(3-dimethylaminopropyl)-3-ethylcarbodiimide hydrochloride (36 mg, 0.19 mmol) was added. The mixture was stirred 2.5 h at 0° C. and 2.5 h at room temperature before being diluted with ethyl acetate (20 mL) and washed with saturated aqueous sodium bicarbonate (2×15 mL) and saturated aqueous sodium chloride (2×15 mL). The aqueous layers were extracted in succession with ethyl acetate (15 mL). The combined organic layers were dried (sodium sulfate), decanted, and evaporated to yield 116 mg of pale yellow residue. Flash column chromatography on silica gel (17 g) packed in dichloromethane and eluting with 20–40% ethyl acetate/dichloromethane yielded 58 mg of partially purified material. Flash column chromatography again on silica gel (9 g) packed in hexane and eluting with 40% ethyl acetate/hexane (400 mL) gave 41 mg (35% yield over three steps) of 5-tert-butyl ester 2(R)-(2-(4-(1-n-propyl)phenyl)ethyl)-4-(4-(2-benzimidazolyl)butyl) pentanedioic acid 1-(L-leucine, N-phenylamide)amide as a colorless film: 400 MHz $^1$H NMR (CDCl₃) δ 9.63 (bs, 1H), 8.67 (s, 1H), 7.66 (bs, 1H), 7.48 (d, 2H, J=7 Hz), 7.37 (bs, 1H), 7.24 (t, 2H, J=7 Hz), 7.20–7.15 (m, 2H), 7.04 (t, 1H, J=7 Hz), 6.98 (d, 2H, J=8 Hz), 6.88 (d, 2H, J=8 Hz), 6.57 (d, 1H, J=8 Hz), 4.59 (q, 1H, J=7 Hz), 2.87 (t, 2H, J=7 Hz), 2.49–2.41 (m, 1H), 2.48 (t, 2H, J=7 Hz), 2.40–2.25 (m, 2H), 2.18–2.09 (m, 1H), 1.94–1.22 (m, 15H), 1.33 (2, 9H), 0.94 (d, 3H, J=6 Hz), 0.92 (d, 3H, J=6 Hz), 0.89 (t, 3H, J=7 Hz).

Step C

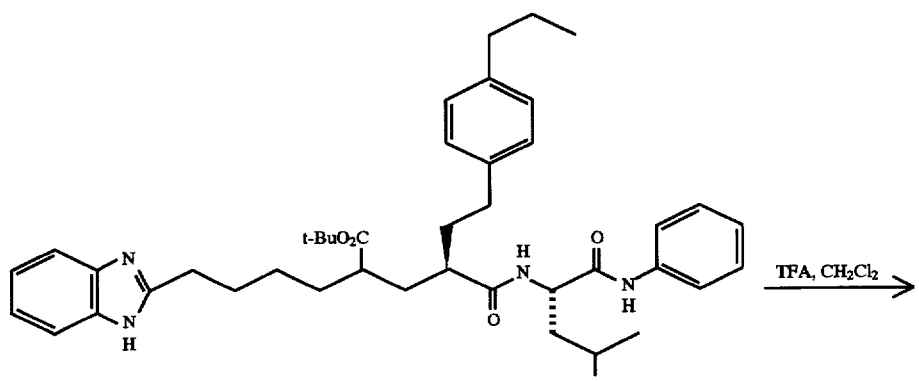

TFA, CH₂Cl₂

-continued

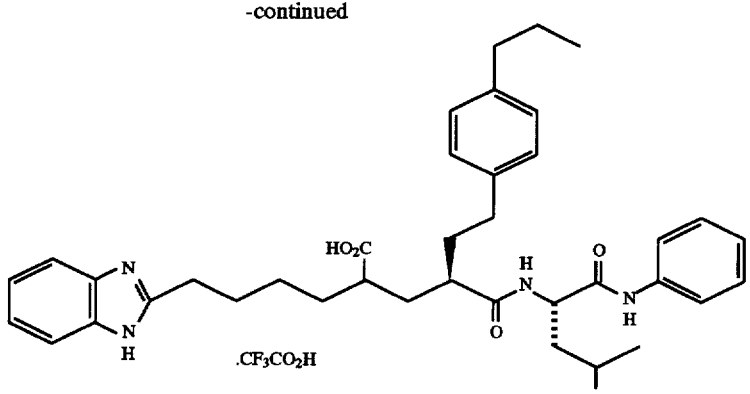

2(R)-(2-(4-(1-n-Propyl)phenyl)ethyl)-4-(4-(2-benzimidazolyl)-butyl)-1,5-pentanedioic acid 1-(L-leucine, N-phenylamide)amide, trifluoroacetic acid salt: Trifluoroacetic acid (0.3 mL) was added to a 0° C. solution of 5-tert-butyl ester 2(R)-2-(2-(4-(1-n-propyl)phenyl)ethyl)-4-(4-(2-benzimidazolyl)butyl)pentanedioic acid 1-(L-leucine, N-phenylamide)amide (20 mg, 0.029 mmol) in dichloromethane (0.3 mL). The solution was stirred for 2.75 h at 0° C. followed by 1 h at room temperature. Toluene was added and the solution was evaporated. Added and evaporated toluene two additional times. The residue was dissolved in ethyl acetate, filtered through a 0.45 micron membrane, and evaporated to give 16 mg (73% yield) of the title compound as a colorless film: 400 MHz $^1$H NMR (CD$_3$OD) δ 7.72 (dd, 2H, J=6, 3 Hz), 7.56 (dd, 2H, J=6, 3 Hz), 7.53 (d, 2H, J=8 Hz), 7.27 (t, 2H, J=8 Hz), 7.06 (t, 1H, J=8 Hz), 7.00 (s, 4H), 4.57 (dd, 1H, J=9, 5 Hz), 3.14 (t, 2H, J=8 Hz), 2.59–2.35 (m, 3H), 2.49 (t, 3H, J=8 Hz), 2.00–1.52 (m, 13H), 1.48–1.35 (m, 2H), 0.96 (d, 3H, J=6 Hz), 0.94 (d, 3H, J=6 Hz), 0.89 (t, 3H, J=7 Hz). MS (FAB), m/e=639 [M+1].

EXAMPLE 13

2(R)-(2-(4-(1-n-Propyl)phenyl)ethyl)-4-(4-(2-benzthiazolyl)butyl)-1,5-pentanedioic acid 1-(L-leucine, N-phenylamide)amide, trifluoroacetic acid salt

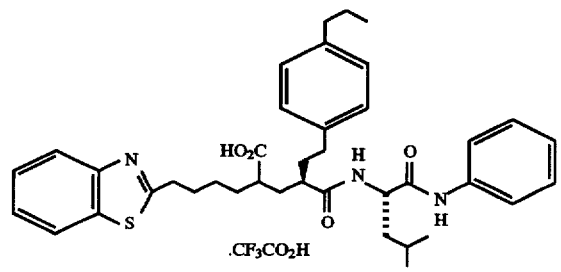

Step A

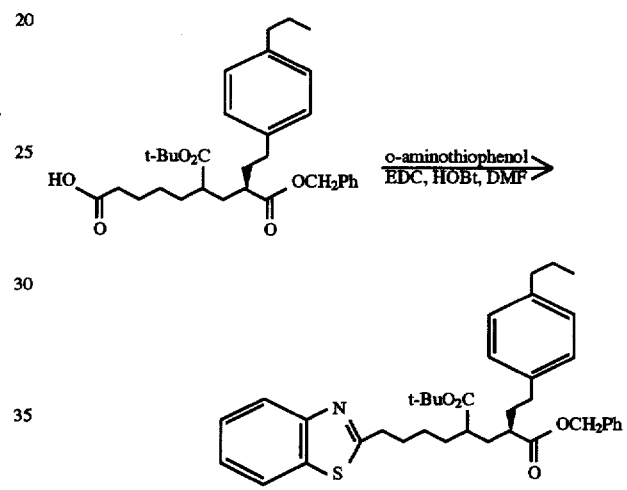

1-Benzyl ester 5-tert-butyl ester 2(R)-(2-(4-(1-n-propyl)phenyl)ethyl)-4-(4-(2-benzthiazolyl)-butyl)-1,5-pentanedioic acid: 1-Hydroxybenzotriazole hydrate (23 mg, 0.15 mmol) and 1-(3-dimethylaminopropyl)-3-ethylcarbodiimide hydrochloride (25 mg, 0.13 mmol) were added to a solution of 1-benzyl ester 2(R)-(2-(4-(1-n-propyl)phenyl)ethyl)-4-(tert-butoxycarbonyl)-1,9-nonanedioic acid [from Example 12] (50 mg, 0.095 mmol) in DMF (0.8 mL). After 2 h, o-aminothiophenol (0.013 mL, 0.015 mg, 0.12 mmol) was added. After an additional 4 h, the mixture was diluted with ethyl acetate (15 mL) and washed with saturated aqueous sodium bicarbonate (2×15 mL) followed by saturated aqueous sodium chloride (2×15 mL). The aqueous layers wer extracted in succession with ethyl acetate (10 mL). The combined organic extracts were dried (sodium sulfate), decanted, and evaporated to give 63 mg of yellow material which was dissolved in acetic acid (4.0 mL). The acetic acid solution was heated in a 140° C. oil bath for 4 h, cooled to room temperature, and evaporated. The residue was dissolved in ethyl acetate (20 mL), washed with saturated aqueous sodium bicarbonate (20 mL) and saturated aqueous sodium chloride (20 mL), dried (sodium sulfate), decanted, and evaporated. Flash column chromatogrpahy on silica gel (7.5 g) eluting with 5% ethyl acetate/hexane (200 mL) and 10% ethyl acetate/hexane (200 mL) yielded 20 mg (34% yield) of 1-benzyl ester 5-tert-butyl ester 2(R)-(2-(4-

(1-n-propyl)phenyl)ethyl)-4-(4-(2-benzthiazolyl)butyl)-1,5-pentanedioic acid: 400 MHz $^1$H NMR (CDCl$_3$) δ 7.93 (d, 1H, J=7 Hz), 7.80 (d, 1H, J=7 Hz), 7.42 (td, 1H, J=7, 1 Hz), 7.37–7.26 (m, 6H), 7.04 (d, 2H, J=8 Hz), 6.98 (d, 2H, J=8 Hz), 5.10 (s, 2H), 3.04 (t, 2H, J=7 Hz), 2.55–2.40 (m, 3H), 2.50 (t, 2H, J=7 Hz), 2.27–2.19 (m, 5H), 2.00–1.72 (m, 5H), 1.63–1.24 (m, 7H), 1.34 (s, 9H), 0.90 (t, 3H, J=7 Hz).

Step B

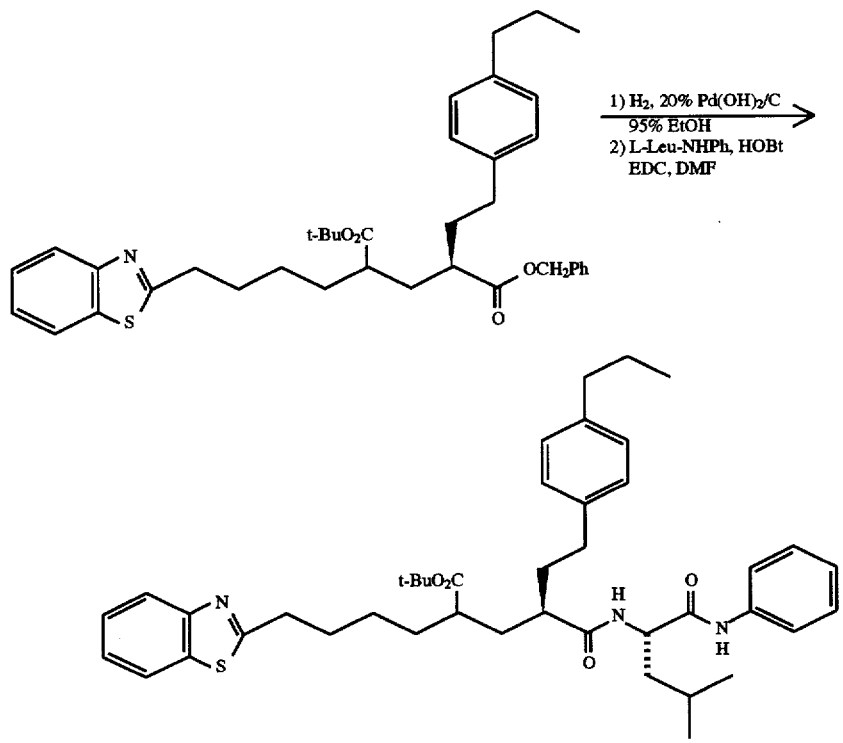

5-tert-Butyl ester 2(R)-(2-(4-(1-n-propyl)phenyl)ethyl)-4-(4-(2-benzthiazolyl)-butyl)-1,5-pentanedioic acid 1-(L-leucine, N-phenylamide)amide: 1-Benzyl ester 5-tert-butyl ester 2(R)-(2-(4-(1-n-propyl)phenyl)ethyl)-4-(4-(2-benzthiazolyl)-butyl)-1,5-pentanedioic acid (33 mg, 0.054 mmol) was dissolved in 95% ethanol (2.2 mL) and stirred with 20% palladium hydroxide/carbon (16 mg) in a round bottom flask connected to a hydrogen-filled balloon. Additional portions of 20% palladium hydroxide/carbon (16 mg, 16 mg, and 17 mg) were added at 3 h, 5.5 h, and 8 h after the start of the reaction. After a total of 31 h, the reaction mixture was filtered through a 0.45 micron membrane and the filtrate was evaporated. The residue was redissolved in 95% ethanol (1.6 mL) and hydrogenation was allowed to proceed overnight with 20% palladium hydroxide/carbon (23 mg). The following day, additional fresh catalyst (24 mg) was added, followed 8 h later by another 13 mg. After 2 h, the mixture was filtered through a 0.45 micron membrane and the catalyst was rinsed with 15:1 95% ethanol/acetic acid. Evaporation of the filtrate yielded 19 mg of crude 2(R)-(2-(4-(1-n-propyl)phenyl)ethyl)-4-(4-(2-benzthiazolyl)butyl)-1,5-pentanedioic acid.

1-Hydroxybenzotriazole hydrate (7.5 mg, 0.049 mmol) and L-leucine, N-phenylamide (9 mg, 0.04 mmol) were added to a solution of the crude hydrogenation product (19 mg) dissolved in DMF (0.3 mL). The solution was cooled to 0° C. and 1-(3-dimethylaminopropyl)-3-ethylcarbodiimide hydrochloride (8.2 mg, 0.043 mmol) was added. The mixture was stirred 2.5 h at 0° C. and 3 h at room temperature before being diluted with ethyl acetate (10 mL) and washed with saturated aqueous sodium bicarbonate (2×10 mL) and saturated aqueous sodium chloride (2×10 mL). The aqueous layers were extracted in succession with ethyl acetate (6 mL). The combined organic layers were dried (sodium sulfate), decanted, and evaporated to yield 25 mg of colorless residue. Flash column chromatography on silica gel (4 g) packed in dichloromethane and eluting with 20–40% ethyl acetate/dichloromethane yielded 58 mg of partially purified material. Flash column chromatography again on silica gel (9 g) packed in hexane and eluting with 10% ethyl acetate/hexane (150 mL) and 15% ethyl acetate/hexane (150 mL) gave 11 mg (46% yield over two steps) of 5-tert-butyl ester 2(R)-2-(2-(4-(1-n-propyl)phenyl)ethyl)-4-(4-(2-benzthiazolyl)butyl)-pentanedioic acid 1-(L-leucine, N-phenylamide)amide as a colorless film: 400 MHz $^1$H NMR (CDCl$_3$) δ 8.57 (s, 1H), 7.93 (d, 1H, J=7 Hz), 7.81 (d, 1H, J=7 Hz), 7.50 (d, 2H, J=7 Hz), 7.42 (td, 1H, J=7, 1 Hz), 7.32 (td, 1H, J=7, 1 Hz), 7.26 (t, 2H, J=7 Hz), 7.05 (t, 1H, J=7 Hz), 6.99 (d, 2H, J=8 Hz0, 6.89 (d, 2H, J=8 Hz), 6.08 (d, 1H, J=7 Hz), 4.57 (td, 1H, J=7, 6 Hz), 3.07 (t, 2H, J=7 Hz), 2.53–2.44 (m, 1H), 2.48 (t, 2H, J=7 Hz), 2.37–2.25 (m, 2H), 2.08–2.00 (m, 1H), 1.93–1.24 (m, 18H), 1.33 (s, 9H), 0.94 (d, 3H, J=6 Hz), 0.92 (d, 3H, J=6 Hz), 0.89 (t, 3H, J=7 Hz).

Step C

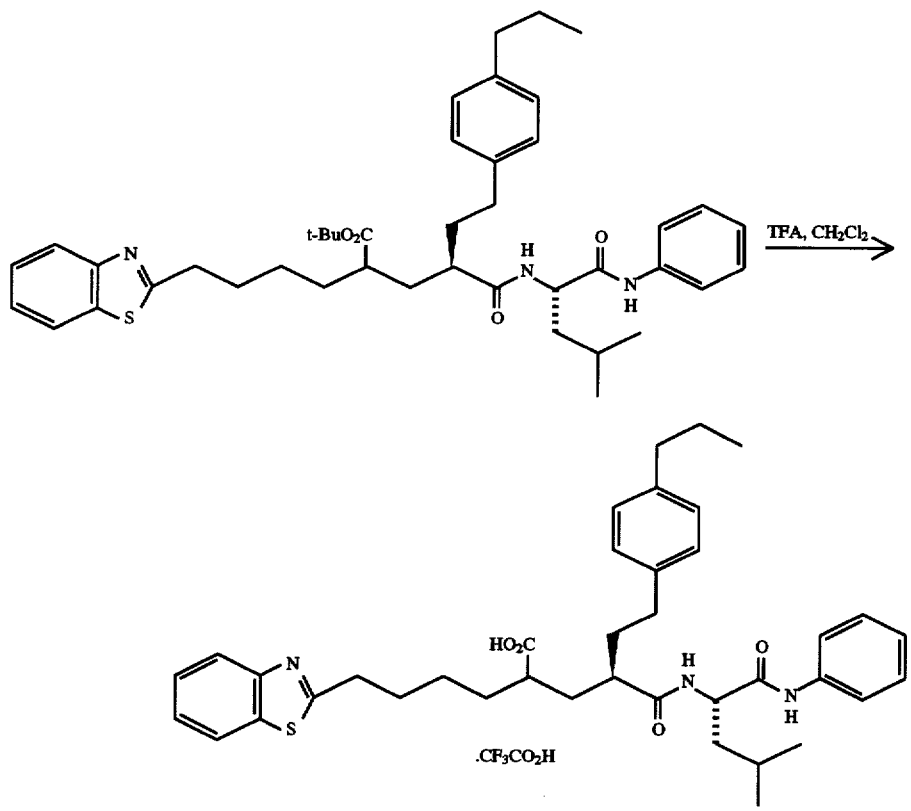

2(R)-(2-(4-(1-n-Propyl)phenyl)ethyl)-4-(4-(2-benzthiazolyl)-butyl)-1,5-pentanedioic acid 1-(L-leucine, N-phenylamide)amide, trifluoroacetic acid salt: Trifluoroacetic acid (0.25 mL) was added to a 0° C. solution of 5-tert-butyl ester 2(R)-(2-(4-(1-n-propyl)phenyl)ethyl)-4-(4-(2-benzthiazolyl)butyl)-1,5-pentanedioic acid 1-(L-leucine, N-phenylamide)amide (11 mg, 0.015 mmol) in dichloromethane (0.25 mL). The solution was stirred for 1 h at 0° C. followed by 1 h at room temperature. Toluene was added and the solution was evaporated. Added and evaporated toluene two additional times. The residue was dissolved in ethyl acetate, filtered through a 0.45 micron membrane, and evaporated to give 10 mg of colorless film. Preparative HPLC on a 22 mm×25 cm Whatman ODS-3 column eluting with 70% acetonitrile/30% water/0.05% trifluoroacetic acid yielded the title compound as 7.5 mg (75% yield) of colorless film: 400 MHz $^1$H NMR (CD$_3$OD) δ 7.92 (d, 1H, J=8 Hz), 7.90 (d, 1H, J=8 Hz), 7.55 (d, 2H, J=8 Hz), 7.48 (td, 1H, J=8, 1.5 Hz), 7.39 (td, 1H, J=8, 1.5 Hz), 7.28 (t, 2H, J=8 Hz), 7.07 (t, 1H, J=8 Hz), 7.00 (s, 4H), 4.57 (dd, 1H, J=9, 5 Hz), 3.13 (t, 2H, J=7 Hz), 2.57–2.40 (m, 3H), 2.48 (t, 2H, J=8 Hz), 2.37–2.28 (m, 1H), 1.99–1.27 (m, 15H), 0.92 (d, 3H, J=6 Hz), 0.91 (d, 3H, J=6 Hz), 0.89 (t, 3H, J=7 Hz). MS (FAB), m/e=656 [M+1].

EXAMPLE 14

2(R)-(2-(4-(1-n-Propyl)phenyl)ethyl)-4-(4-(2-benzoxazolyl)butyl)-1,5-pentanedioic acid 1-(L-leucine, N-phenylamide)amide

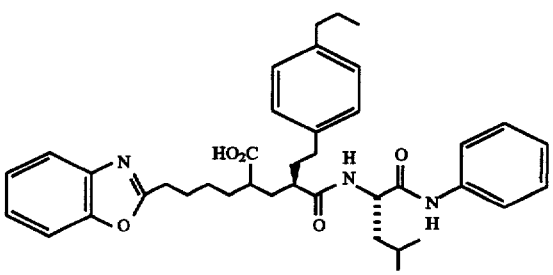

Step A

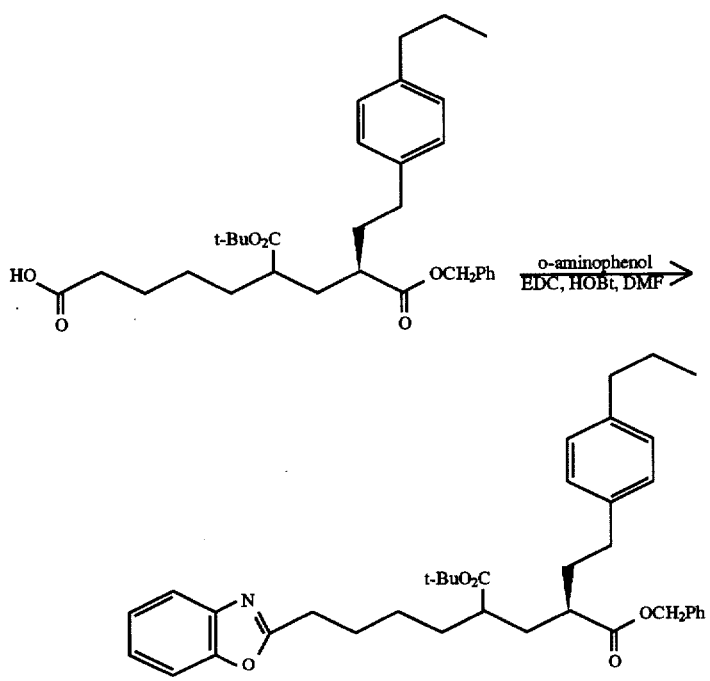

1-Benzyl ester 5-tert-butyl ester 2(R)-(2-(4-(1-n-propyl)phenyl)ethyl)-4-(4-(2-benzoxazolyl)-butyl)-1,5-pentanedioic acid: 1-Hydroxybenzotriazole hydrate (137 mg, 0.90 mmol) and 1-(3-dimethylaminopropyl)-3-ethylcarbodiimide hydrochloride (155 mg, 0.81 mmol) were added to a solution of 1-benzyl ester 2(R)-(2-(4-(1-n-propyl)phenyl)ethyl)-4-(tert-butoxycarbonyl)-1,9-nonanedioic acid (300 mg, 0.57 mmol) in DMF (5.2 mL). After 2.5 h, o-aminophenol (89 mg, 0.82 mmol) was added. After an additional 4 h, the mixture was diluted with ethyl acetate (120 mL) and washed with saturated aqueous sodium bicarbonate (2×100 mL) followed by saturated aqueous sodium chloride (2×100 mL). The aqueous layers wer extracted in succession with ethyl acetate (75 mL). The combined organic extracts were dried (sodium sulfate), decanted, and evaporated to give 389 mg of orange oil which was dissolved in acetic acid (25 mL). The acetic acid solution was refluxed for 2 h, cooled to room temperature, and evaporated. The residue was dissolved in ethyl acetate (100 mL), washed with saturated aqueous sodium bicarbonate (100 mL) and saturated aqueous sodium chloride (100 mL), dried (sodium sulfate), decanted, and evaporated. Flash column chromatogrpahy on silica gel (30 g) packed in dichloromethane and eluting with 2% ethyl acetate/dichloromethane (400 mL) yielded 0.14 g (41% yield) of 1-benzyl ester 5-tert-butyl ester 2(R)-2-(2-(4-(1-n-propyl)phenyl)ethyl)-4-(4-(2-benzoxazolyl)butyl)-1,5-pentanedioic acid: 400 MHz $^1$H NMR (CDCl$_3$) δ 7.66–7.61 (m, 1H), 7.46–7.43 (m, 1H), 7.36–7.24 (m, 7H), 7.04 (d, 2H, J=8 Hz), 6.98 (d, 2H, J=8 Hz), 5.10 s, 2H), 2.86 (t, 2H, J=7 Hz), 2.55–2.39 (m, 3H), 2.50 (t, 2H, J=7 Hz), 2.27–2.18 (m, 1H), 2.00–1.72 (m, 5H), 1.63–1.24 (m, 7H), 1.33 (s, 9H), 0.90 (t, 3H, J=7 Hz).

Step B

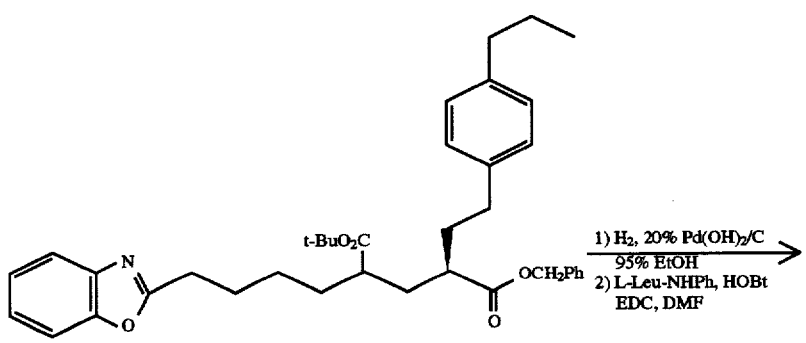

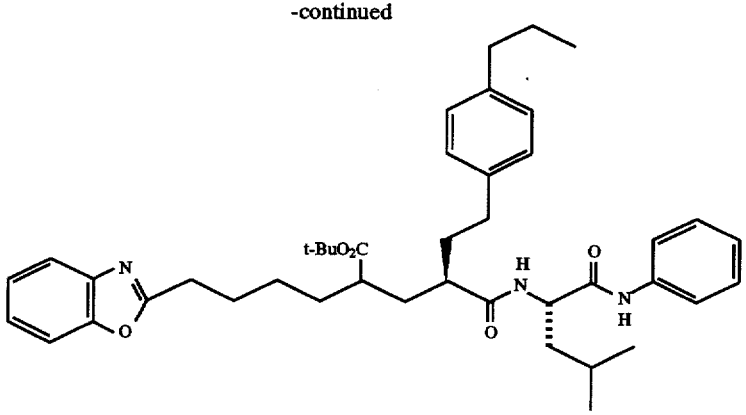

5-tert-Butyl ester 2(R)-(2-(4-(1-n-propyl)phenyl)ethyl)-4-(4-(2-benzoxazolyl)-butyl)-1,5-pentanedioic acid 1-(L-leucine, N-phenylamide)amide: 2(R)-2-(2-(4-(1-n-Propyl)phenyl)ethyl)-4-(4-(2 -benzoxazolyl)-butyl)pentanedioic acid 1-benzyl ester 5-tert-butyl ester (141 mg, 0.24 mmol) was dissolved in 95% ethanol (10.0 mL) and stirred with 20% palladium hydroxide/carbon (49 mg) in a round bottom flask connected to a hydrogen-filled balloon. After 1 h, the mixture was filtered through a 0.45 micron membrane. Evaporation of the filtrate yielded 118 mg (98% yield) of crude 5-tert-butyl 2(R)-2-(2-(4-(1-n-propyl)phenyl)ethyl)-4-(4-(2-benzoxzolyl)butyl)-1,5-pentanedioic acid.

1-Hydroxybenzotriazole hydrate (46 mg, 0.30 mmol) and L-leucine, N-phenylamide (55 mg, 0.27 mmol) were added to a solution of the crude hydrogenation product (112 mg) dissolved in DMF (1.8 mL). The solution was cooled to 0° C. and 1-(3-dimethylaminopropyl)-3-ethylcarbodiimide hydrochloride (50 mg, 0.26 mmol) was added. The mixture was stirred 2.5 h at 0° C. and 2.5 h at room temperature before being diluted with ethyl acetate (25 mL) and washed with saturated aqueous sodium bicarbonate (2×20 mL) and saturated aqueous sodium chloride (2×20 mL). The aqueous layers were extracted in succession with ethyl acetate (20 mL). The combined organic layers were dried (sodium sulfate), decanted, and evaporated to yield 160 mg of colorless residue. Flash column chromatography on silica gel (16 g) packed in hexane and eluting with 20% ethyl acetate/hexane (500 mL) yielded 123 mg (80% yield) of 5-tert-butyl ester 2(R)-(2-(4-(1-n-propyl)phenyl)ethyl)-4-(4-(2-benzoxazolyl)butyl)-1,5-pentanedioic acid 1-(L-leucine, N-phenylamide)amide as a colorless oil: 400 MHz $^1$H NMR (CDCl$_3$) δ 8.55 (s, 1H), 7.66–7.61 (m, 1H), 7.50 (d, 2H, J=7 Hz), 7.47–7.42 (m, 1H), 7.30–7.23 (m, 4H), 7.06 (t, 1H, J=7 Hz), 6.98 (d, 2H, J=8 Hz), 6.89 (d, 2H, J=8 Hz), 6.12 (d, 1H, J=7 Hz), 4.57 (td, 1H, J=7, 6 Hz), 2.89 (t, 2H, J=7 Hz), 2.54–2.45 (m, 1H), 2.48 (t, 2H, J=7 Hz), 2.38–2.26 (m, 2H), 2.09–2.01 (m, 1H), 1.74–1.30 (m, 15H), 1.33 (s, 9H), 0.94 (d, 3H, J=6 Hz), 0.92 (d, 3H, J=6 Hz), 0.89 (t, 3H, J=7 Hz).

Step C

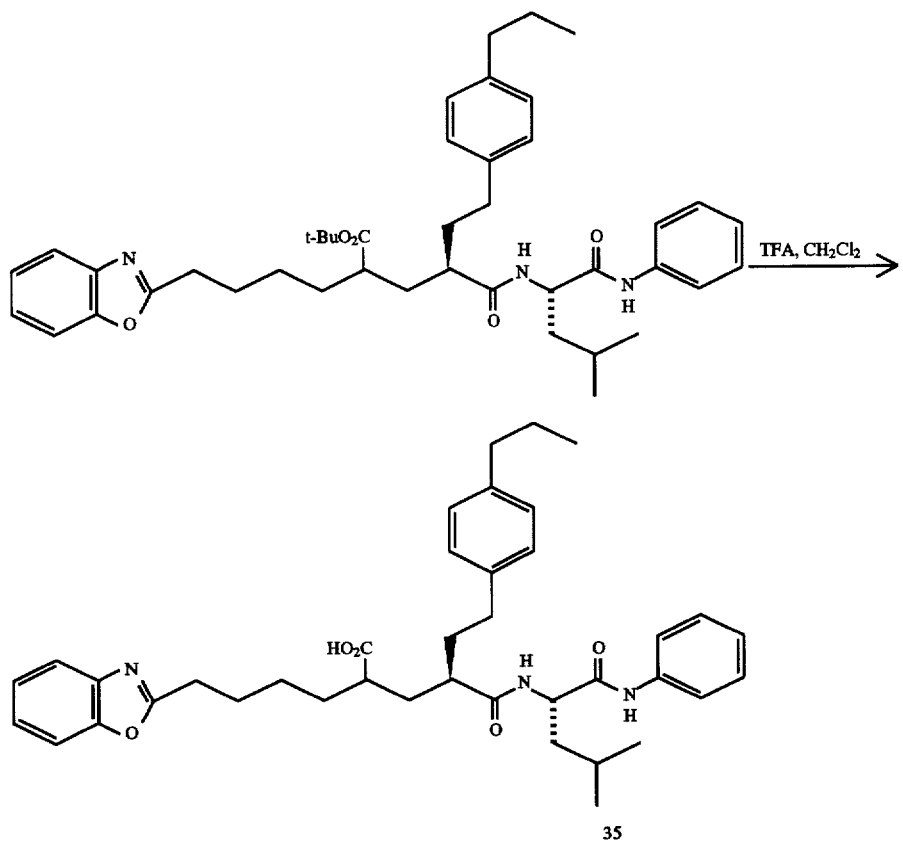

2(R)-(2-(4-(1-n-Propyl)phenyl)ethyl)-4-(4-(2-benzoxazolyl)butyl)-1,5-pentanedioic acid 1-(L-leucine, N-phenylamide)amide: Trifluoroacetic acid (3.0 mL) was added to a 0° C. solution of 5-tert-butyl ester 2(R)-(2-(4-(1-n-propyl)phenyl)ethyl)-4-(4-(2-benzoxazolyl)butyl)-1,5-pentanedioic acid 1-(S-leucine, N-phenylamide)amide (123 mg, 0.177 mmol) in dichloromethane (3.0 mL). The solution was stirred for 2 h at 0° C. followed by 1.5 h at room temperature. Toluene was added and the solution was evaporated. Added and evaporated toluene two additional times. The residue was dissolved in ethyl acetate, filtered through a 0.45 micron membrane, and evaporated to give 116 mg of the title compound as an off-white foam: 400 MHz $^1$H NMR (CD$_3$OD) δ 7.67–7.60 (m, 1H), 7.57–7.52 (m, 3H), 7.37–7.31 (m, 2H), 7.28 (t, 2H, J=8 Hz), 7.07 (t, 1H, J=8 Hz), 7.00 (s, 4H), 4.57 (dd, 1H, J=9, 5 Hz), 2.96 (t, 2H, J=7 Hz), 2.59–2.40 (m, 5H), 2.38–2.28 (m, 1H), 1.99–1.31 (m, 15H), 0.94 (d, 6H, J=6 Hz), 0.89 (t, 3H, J=8 Hz). MS (FAB), m/e=640 [M+1].

EXAMPLE 15

2(R)-(2-(4-(1-n-Propyl)phenyl)ethyl)-4-carboxy-1,9-nonanedioic acid 1-(L-leucine, N-phenylamide) amide 9-piperidineamide

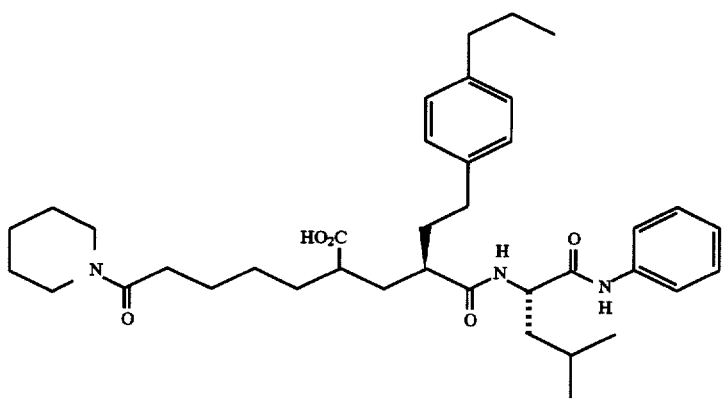

Step A

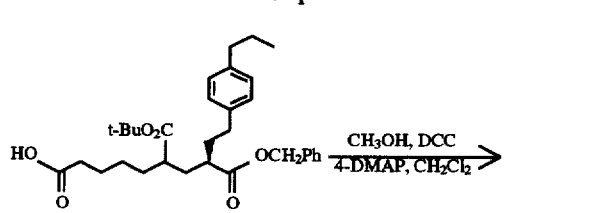

1-Benzyl ester 9-methyl ester 2(R)-(2-(4-(1-n-propyl)phenyl)ethyl)-4-(tert-butoxycarbonyl)-1,9-nonanedioic acid: Methanol (0.53 mL, 0.42 g, 13 mmol) and 4-(dimethylamino)pyridine (154 mg, 1.26 mmol) were added to a solution of 1-benzyl ester 2(R)-(2-(4-(1-n-propyl)phenyl)ethyl)-4-(tert-butoxycarbonyl)-1,9-nonanedioic acid [from Example 12] (3.28 g, 6.25 mmol) in dichloromethane (19 mL). A solution of 1,3-dicyclohexylcarbodiimide (1.95 g, 9.43 mmol) in dichloromethane (3.8 mL) was added, with additional dichloromethane (3.8 mL) to rinse. After 4 h of stirring at room temperature, the reaction mixture was diluted with hexane (45 mL) and water (3 mL) was added. The mixture was filtered and the precipitate was washed with hexane (30 mL). The filtrate was diluted with hexane (75 mL) and washed with 2N aqueous hydrochloric acid (125 mL), saturated aqueous sodium bicarbonate (125 mL), and saturated aqueous sodium chloride (125 mL). The organic layer was dried (sodium sulfate), filtered, and evaporated to give 3.66 g of pale yellow oil. Flash column chromatography on silica gel (110 g) eluting with 10% ethyl acetate/hexane (1 L) gave 2.75 g (82% yield) of 1-benzyl ester 9-methyl ester 2(R)-(2-(4-(1-n-propyl)phenyl)ethyl)-4-(tert-butoxycarbonyl)-1,9-nonanedioic acid as a colorless oil: 400 MHz $^1$H NMR (CDCl$_3$) δ 7.37–7.28 (m, 5H), 7.04 (d, 2H, J=8 Hz), 6.98 (d, 2H, J=8 Hz), 5.10 (s, 2H), 3.62 (s, 3H), 2.56–2.39 (m, 5H), 2.24 (t, 2H, J=7 Hz), 2.25–2.17 (m, 1H), 1.99–1.84 (m, 2H), 1.82–1.73 (m, 1H), 1.63–1.45 (m, 6H), 1.42–1.33 (m, 1H), 1.37 (s, 9H), 1.28–1.17 (m, 2H), 0.90 (t, 3H, J=7 Hz).

Step B

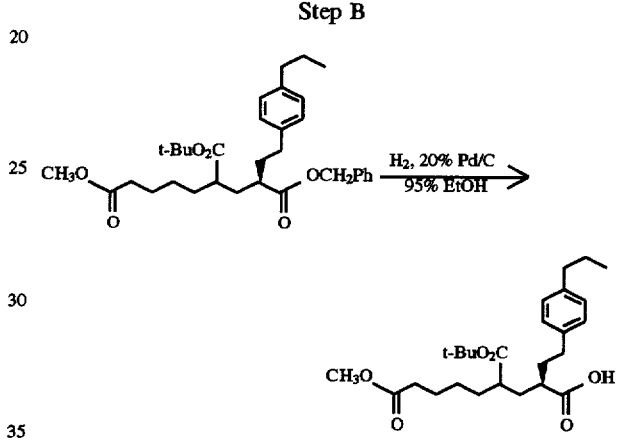

9-Methyl ester 2(R)-(2-(4-(1-n-propyl)phenyl)ethyl)-4-(tert-butoxycarbonyl)-1,9-nonanedioic acid: A solution of 2(R)-(2-(4-(1-n-propyl)phenyl)ethyl)-4-(tert-butoxycarbonyl)nonanedioic acid 1-benzyl ester 9-methyl ester (2.75 g, 5.10 mmol) in 95% ethanol (120 mL) was stirred with 20% palladium hydroxide on carbon (1.107 g) in a round bottom flask connected to a hydrogen-filled balloon. After 1.5 h, the mixture was centrifuged and the supernatant was filtered through a 0.45 micron membrane. The catalyst was rinsed with additional 95% ethanol and the filtrate was evaporated to yield 2.29 g (100% yield) of 9-methyl ester 2(R)-(2-(4-(1-n-propyl)phenyl)ethyl)-4-(tert-butoxycarbonyl)-1,9-nonanedioic acid as a colorless oil: 400 MHz $^1$H NMR (CDCl$_3$) δ 7.07 (s, 3H), 3.03 (3, 3H), 2.64 (ddd, 1H, J=14, 10, 5), 2.57–2.48 (m, 1H), 2.52 (t, 2H, J=7.5 Hz), 2.46–2.36 (m, 1H), 2.33–2.24 (m, 1H), 2.26 (t, 2H, J=7 Hz), 2.03–1.87 (m, 2H), 1.86–1.75 (m, 1H), 1.65–1.50 (m, 6H), 1.46–1.36 (m, 1H), 1.38 (s, 9H), 1.32–1.22 (m, 2H), 0.91 (t, 3H, J=7 Hz).

Step C

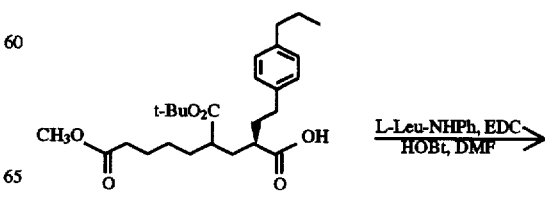

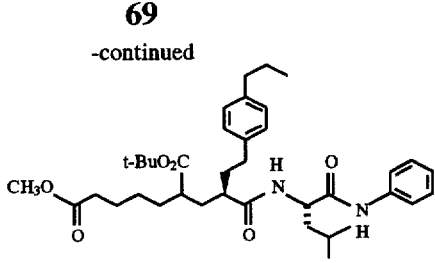

9-Methyl ester 2(R)-(2-(4-(1-n-propyl)phenyl)ethyl)-4-(tert-butoxycarbonyl)-1,9-nonanedioic acid 1-(L-leucine, N-phenylamide)amide: 1-Hydroxybenzotriazole hydrate (24 mg, 0.16 mmol) and L-leucine, N-phenylamide (28 mg, 0.14 mmol) were added to a solution of 9-methyl ester 2(R)-(2-(4-(1-n-propyl)phenyl)ethyl)-4-(tert-butoxycarbonyl)-1,9-nonanedioic acid (48 mg, 0.11 mmol) in DMF (1.0 mL). The solution was cooled to 0° C. and 1-(3-dimethylaminopropyl)-3-ethylcarbodiimide hydrochloride (26 mg, 0.14 mmol) was added. The mixture was stirred at 0° C. for 2 h and at room temperature for 3 h before being diluted with ethyl acetate (15 mL) and washed with saturated aqueous sodium bicarbonate (2×10 mL) and saturated aqueous sodium chloride (2×10 mL). The aqueous layers were extracted in succession with ethyl acetate (10 mL). The combined organic layers were dried (sodium sulfate), decanted, and evaporated. Flash column chromatography on silica gel (5 g) packed in dichloromethane and eluting with 5% ethyl acetate/dichloromethane (100 mL) and 10% ethyl acetate/dichloromethane (50 mL) yielded 54 mg (79% yield) of 9-methyl ester 2(R)-(2-(4-(1-n-propyl)phenyl)ethyl)-4-(tert-butoxycarbonyl)-1,9-nonanedioic acid 1-(L-leucine, N-phenylamide)amide as a white foam: 400 MHz $^1$H NMR (CDCl$_3$) δ 8.52 (s, 1H), 7.50 (d, 2H, J=7 Hz), 7.27 (t, 2H, J=7 Hz), 7.06 (t, 1H, J=7 Hz), 7.00 (d, 2H, J=7 Hz), 6.92 (d, 2H, J=7 Hz), 5.95 (d, 1H, J=7 Hz), 4.56 (td, 1H, J=7, 5.5 Hz), 3.63 (s, 3H), 2.54 (ddd, 1H, J=13, 9, 4 Hz), 2.49 (t, 2H, J=7 Hz), 2.36 (dt, 1H, J=13, 7 Hz), 2.32–2.24 (m, 1H), 2.26 (t, 2H, J=7 Hz), 2.11–2.01 (m, 1H), 1.96–1.20 (m, 15H), 1.37 (s, 9H), 0.96 (d, 3H, J=6 Hz), 0.94 (d, 3H, J=6 Hz), 0.89 (t, 3H, J=7 Hz).

Step D

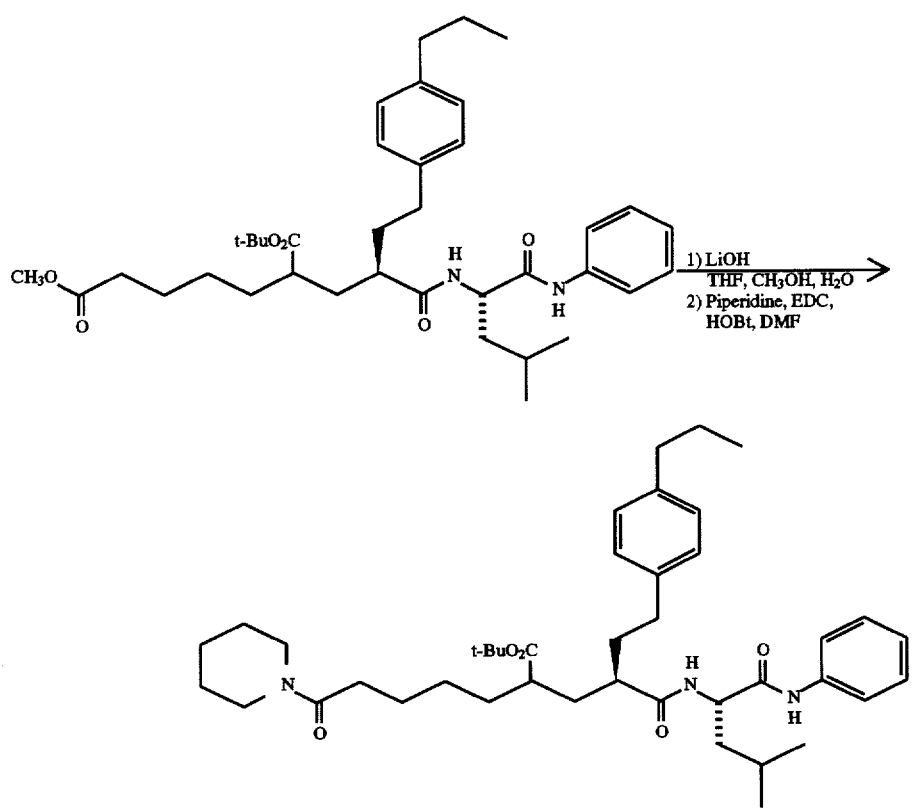

2(R)-(2-(4-(1-n-Propyl)phenyl)ethyl)-4-(tert-butoxycarbonyl)-1,9-nonanedioic acid 1-(L-leucine, N-phenylamide)amide 9-piperidineamide: A solution of 9-methyl ester 2(R)-2-(2-(4-(1-n-propyl)phenyl)ethyl)-4-(tert-butoxycarbonyl)-1,9-nonanedioic acid 1-(L-leucine, N-phenylamide)amide (50 mg, 0.079 mmol) in THF (1.5 mL) and methanol (1.0 mL) was stirred at 0° C. as 0.18N aqueous lithium hydroxide (0.50 mL, 0.09 mmol) was added. The reaction mixture was stirred 1.5 h at 0° C. and 5.5 h at room temperature. NMR of a worked-up aliquot (0.35 mL) showed 25% methyl ester remaining. Additional 0.18N aqueous lithium hydroxide (0.18 mL, 0.032 mmol) was added and stirring was continued at room temperature for 4 h. The mixture was partitioned between ethyl acetate (50 mL) and 2N aqueous hydrochloric acid (25 mL). The organic layer was washed with saturated aqueous sodium chloride (25 mL), dried (sodium sulfate), decanted, and evaporated to give crude 2(R)-(2-(4-(1-n-propyl)phenyl)ethyl)-4-(tert-butoxycarbonyl)-1,9-nonanedioic acid 1-(L-leucine, N-phenylamide)amide as 44 mg of colorless film.

A portion of the crude acid (38 mg, 0.061 mmol) was dissolved in DMF (0.5 mL). Piperidine (0.007 mL, 6 mg, 0.07 mmol), 1-hydroxybenzotriazole hydrate (13 mg, 0.085 mmol), and 1-(3-dimethylaminopropyl)-3-ethylcarbodiimide hydrochloride (14 mg, 0.073 mmol) were added and the mixture was stirred at room temperature for 5 h. The reaction mixture was diluted with ethyl acetate (15 mL) and washed with saturated aqueous sodium bicarbonate (2×10 mL) and saturated aqueous sodium chloride (2×10 mL). The aqueous layers were extracted in succession with ethyl acetate (10 mL). The combined organic layers were dried (sodium sulfate), decanted, and evaporated. Flash column chromatography on silica gel (3.5 g) packed in dichloromethane and eluting with 10% ethyl acetate/dichloromethane (100 mL) and 20% ethyl acetate/dichloromethane (150 mL) gave 34 mg (81% yield) of 2(R)-(2-(4-(1-n-propyl)phenyl)ethyl)-4-(tert-butoxycarbonyl)nonanedioic acid 1-(L-leucine, N-phenylamide)amide 9-piperidineamide as a colorless film: 400 MHz $^1$H NMR (CDCl$_3$) δ 8.74 (s, 1H), 7.50 (d, 2H, J=7 Hz), 7.25 (t, 2H, J=7 Hz), 7.04 (t, 1H, J=7 Hz), 6.99 (d, 2H, J=7 Hz), 6.92 (d, 2H, J=7 Hz), 6.47 (d, 1H, J=7 Hz), 4.59 (q, 1H, J=7 Hz), 3.55–3.45 (m, 2H), 3.39–3.31 (m, 2H), 2.57–2.46 (m, 1H), 2.48 (t, 2H, J=7 Hz), 2.38 (dt, 1H, J=13, 7 Hz), 2.32–2.22 (m, 3H), 2.20–2.11 (m, 1H), 1.97–1.20 (m, 21H), 1.37 (s, 9H), 0.96 (d, 3H, J=6 Hz), 0.94 (d, 3H, J=6 Hz), 0.89 (t, 3H, J=7 Hz).

Step E

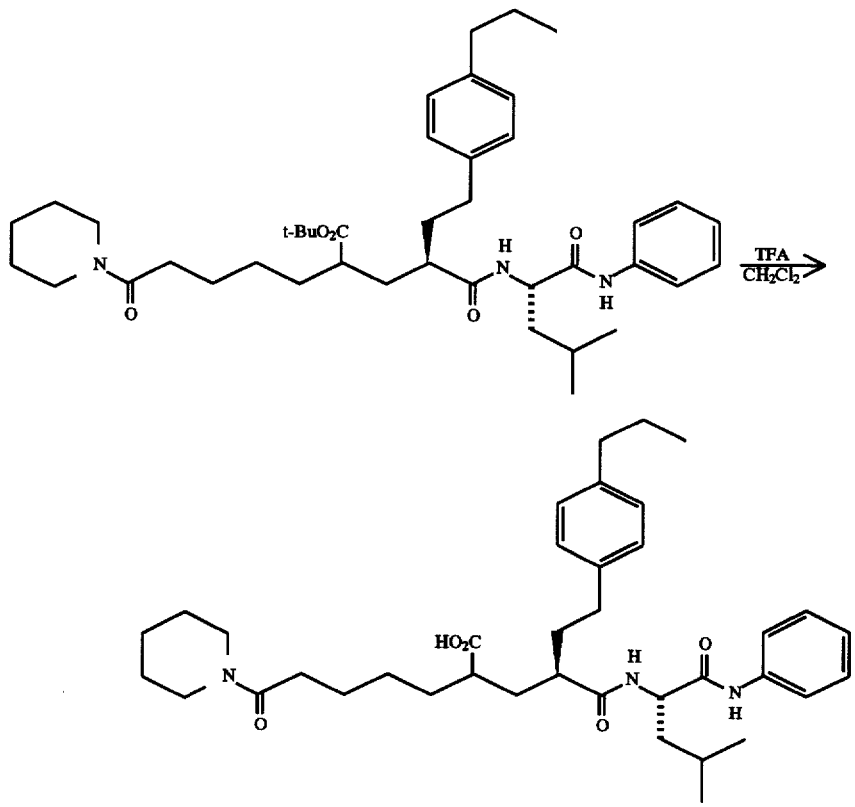

2(R)-(2-(4-(1-n-Propyl)phenyl)ethyl)-4-carboxy-1,9-nonanedioic acid 1-(L-leucine, N-phenylamide)amide 9-piperidineamide: Trifluoroacetic acid (0.85 mL) was added to a 0° C. solution of 2(R)-2-(2-(4-(1-n-propyl)phenyl)ethyl)-4-(tert-butoxycarbonyl)-1,9-nonanedioic acid 1-(S-leucine, N-phenylamide)amide 9-piperidineamide (34 mg, 0.049 mmol) in dichloromethane (0.85 mmol). The solution was stirred for 1 h at 0° C. and 1 h at room temperature. Toluene was added and the solution was evaporated. Repeated addition and evaporation with two additional portions of toluene. The residue was dissolved in ethyl acetate, filtered through a 0.45 micron membrane, and evaporated to give the title compound as 31 mg (100% yield) of off-white foam: 400 MHz $^1$H NMR (CD$_3$OD) δ 7.55 (d, 2H, J=8 Hz), 7.29 (t, 2H, J=8 Hz), 7.08 (t, 1H, J=8 Hz), 7.01 (s, 4H), 4.58 (dd, 1H, J=10, 5 Hz), 3.52 (t, 2H, J=5 Hz), 3.46 (t, 2H, J=5 Hz), 2.60–2.41 (m, 5H), 2.38–2.29 (m, 1H), 2.36 (t, 2H, J=7 Hz), 1.99–1.26 (m, 21H), 1.01 (d, 3H, J=6 Hz), 0.98 (d, 3H, J=6 Hz), 0.90 (t, 3H, J=7 Hz). MS (FAB), m/e=634 [M+1].

The following additional compounds were prepared according to the method of Example 15.

2(R)-(2-(4-(1-n-Propyl)phenyl)ethyl)-4-carboxy-1,9-nonanedioic acid 1-(L-leucine, N-methylamide)amide 9-phenylamide: 400 MHz $^1$H NMR (CD$_3$OD) δ 7.53 (d, 2H, J=8 Hz), 7.27 (t, 2H, J=8 Hz), 7.06 (t, 1H, J=8 Hz), 7.04 (s, 4H), 4.39 (dd, 1H, J=9, 5 Hz), 2.72 (s, 3H), 2.58–2.27 (m, 4H), 2.51 (t, 2H, J=8 Hz), 2.37 (t, 2H, J=8 Hz), 1.98–1.27 (m, 15H), 0.94 (d, 3H, J=6 Hz), 0.92 (d, 3H, J=6 Hz), 0.91 (t, 3H, J=7 Hz). MS (FAB), m/e=580 [M+1].

2(R)-(2-(4-(1-n-Propyl)phenyl)ethyl)-4-carboxy-1,9-nonanedioic acid 1-(L-leucine, N-methylamide)amide 9-tert-butylamide: 400 MHz $^1$H NMR (CD$_3$OD) δ 7.06 (s, 4H), 4.39 (dd, 1H, J=9, 5 Hz), 2.72 (s, 3H), 2.58–2.25 (m, 4H), 2.52 (t, 2H, J=7 Hz), 2.08 (t, 2H, J=7.5 Hz), 1.96–1.45 (m, 13H), 1.38–1.20 (m, 2H), 1.30 (s, 9H), 0.96 (d, 3H, J=6 Hz), 0.93 (d, 3H, J=6 Hz), 0.91 (t, 3H, J=7 Hz).

2(R)-(2-(4-(1-n-Propyl)phenyl)ethyl)-4-carboxy-1,9-nonanedioic acid 1-(L-leucine, N-methylamide)amide 9-benzylamide: 400 MHz $^1$H NMR (CD$_3$OD) δ 7.32–7.18 (m, 5H), 7.07 (s, 4H), 4.39 (dd, 1H, J=9, 5 Hz), 4.33 (s, 2H), 2.72 (s, 3H), 2.58–2.35 (m, 3H), 2.51 (t, 2H, J=7 Hz), 2.33–2.25 (m, 1H), 2.22 (t, 2H, J=7 Hz), 1.96–1.45 (m, 13H), 1.41–1.22 (m, 2H), 0.95 (d, 3H, J=6 Hz), 0.92 (d, 3H, J=6 Hz), 0.91 (t, 3H, J=7 Hz). MS (FAB), m/e=594 [M+1].

2(R)-(2-(4-(1-n-Propyl)phenyl)ethyl)-4-carboxy-1,9-nonanedioic acid 1-(L-leucine, N-methylamide)amide 9-morpholineamide: 400 MHz ¹H NMR (CD₃OD) δ 7.07 (s, 4H), 4.39 (dd, 1H, J=9, 5 Hz), 3.67–3.59 (m, 4H), 3.58–3.49 (m, 4H), 2.72 (s, 3H), 2.58–2.26 (m, 4H), 2.52 (t, 2H, J=7 Hz), 2.37 (t, 2H, J=7 Hz), 1.96–1.25 (m, 15H), 0.96 (d, 3H, J=6 Hz), 0.93 (d, 3H, J=6 Hz), 0.91 (t, 3H, J=7 Hz). MS (FAB), m/e=574 [M+1].

2(R)-(2-(4-(1-n-Propyl)phenyl)ethyl)-4-carboxy-1,9-nonanedioic acid 1-(L-leucine, N-methylamide)amide 9-(1(R)-phenylethyl)amide: 400 MHz ¹H NMR (CD₃OD) δ 7.28 (d, 4H, J=5 Hz), 7.22–7.16 (m, 1H), 7.06 (s, 4H), 4.97 (q, 1H, J=7 Hz), 4.38 (dd, 1H, J=9, 5 Hz), 2.72 (s, 3H), 2.58–2.45 (m, 2H), 2.52 (t, 2H, J=7 Hz), 2.44–2.34 (m, 1H), 2.32–2.24 (m, 1H), 2.19 (t, 2H, J=7 Hz), 1.96–1.44 (m, 13H), 1.41 (d, 3H, J=7 Hz), 1.38–1.21 (m, 2H), 0.94 (d, 3H, J=6 Hz), 0.91 (d, 3H, J=6 Hz), 0.91 (t, 3H, J=7 Hz). MS (FAB), m/e=608 [M+1].

2(R)-(2-(4-(1-n-Propyl)phenyl)ethyl)-4-carboxy-1,9-nonanedioic acid 1-(L-leucine, N-methylamide)amide 9-(1(S)-phenylethyl)amide: 400 MHz ¹H NMR (CD₃OD) δ 7.28 (d, 4H, J=5 Hz), 7.21–7.15 (m, 1H), 7.06 (s, 4H), 4.97 (q, 1H, J=7 Hz), 4.39 (dd, 1H, J=9, 5 Hz), 2.72 (s, 3H), 2.58–2.42 (m, 2H), 2.52 (t, 2H, J=7 Hz), 2.42–2.33 (m, 1H), 2.32–2.23 (m, 1H), 2.19 (t, 2H, J=7 Hz), 1.95–1.44 (m, 13H), 1.41 (d, 3H, J=7 Hz), 1.36–1.21 (m, 2H), 0.96 (d, 3H, J=6 Hz), 0.93 (d, 3H, J=6 Hz), 0.91 (t, 3H, J=7 Hz). MS (FAB), m/e=608 [M+1].

2(R)-(2-(4-(1-n-Propyl)phenyl)ethyl)-4-carboxy-1,9-nonanedioic acid 1-(L-leucine, N-methylamide)amide 9-(N-methyl-N-phenyl)amide: 400 MHz ¹H NMR (CD₃OD) δ 7.45 (t, 2H, J=7 Hz), 7.37 (t, 1H, J=7 Hz), 7.25 (d, 2H, J=7 Hz), 7.06 (s, 4H), 4.38 (dd, 1H, J=9, 5 Hz), 3.22 (s, 3H), 2.72 (s, 3H), 2.57–2.44 (m, 2H), 2.52 (t, 2H, J=7 Hz), 2.40–2.32 (m, 1H), 2.26–2.18 (m, 1H), 2.08 (t, 2H, J=7 Hz), 1.92–1.39 (m, 13H), 1.24–1.06 (m, 2H), 0.92 (d, 3H, J=6 Hz), 0.90 (d, 3H, J=6 Hz), 0.90 (t, 3H, J=7 Hz). MS (FAB), m/e=594 [M+1].

2(R)-(2-(4-(1-n-Propyl)phenyl)ethyl)-4-carboxy-1,9-nonanedioic acid 1-(L-leucine, N-methylamide)amide 9-(N'-methylpiperazine)amide, trifluoroacetic acid salt: 400 MHz ¹H NMR (CD₃OD, spectrum near coalsecence, partial description) δ 7.07 (s, 4H), 4.39 (dd, 1H, J=9, 5 Hz), 2.92 (s, 3H), 2.72 (s, 3H), 2.58–2.27 (m, 8H), 1.96–1.46 (m, 13H), 1.42–1.26 (m, 2H), 0.96 (d, 3H, J=6 Hz), 0.93 (d, 3H, J=6 Hz), 0.91 (t, 3H, J=7 Hz). MS (FAB), m/e=587 [M+1].

2(R)-(2-(4-(1-n-Propyl)phenyl)ethyl)-4-carboxy-1,9-nonanedioic acid 1-(L-leucine, N-methylamide)amide 9-(3-pyridyl)amide: 400 MHz ¹H NMR (CD₃OD) δ 9.38 (s, 1H), 8.49 (d, 1H, J=5 Hz), 8.41 (d, 1H, J=9 Hz), 7.95 (dd, 1H, J=9, 5 Hz), 7.06 (s, 4H), 4.40 (dd, 1H, J=9, 5 Hz), 2.72 (s, 3H), 2.58–2.20 (m, 5H), 2.51 (t, 2H, J=7 Hz), 2.46 (t, 2H, J=7 Hz), 1.97–1.27 (m, 16H), 0.95 (d, 3H, J=6 Hz), 0.92 (d, 3H, J=6 Hz), 0.91 (t, 3H, J=7 Hz).

EXAMPLE 16

2(R)-(2-(4-(1-n-Propyl)phenyl)ethyl)-4-carboxy-1,9-nonanedioic acid 1-(L-leucine, N-methylamide) amide

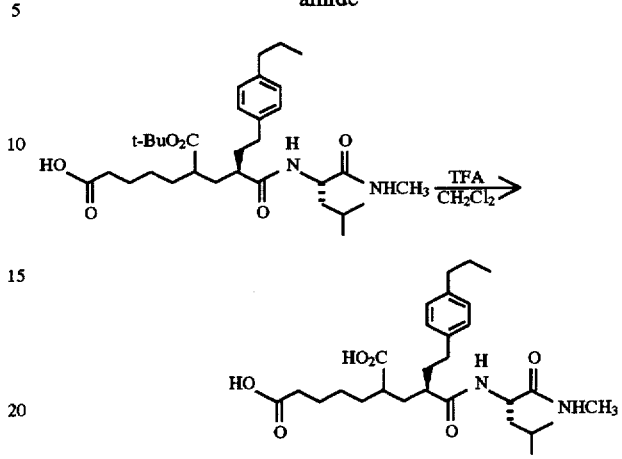

Trifluoroacetic acid (2.0 mL) was added to a solution of 2(R)-(2-(4-(1-n-propyl)phenyl)ethyl)-4-(tert-butoxycarbonyl)nonanedioic acid 1-(S-leucine, N-methylamide)amide (82 mg, 0.15 mmol) in dichloromethane (2.0 mL). The solution was stirred for 3 h at 0° C. and for 2 h at room temperature. Toluene was added and the solution was evaporated. Repeated addition and evaporation with two additional portions of toluene. The residue was dissolved in methanol, filtered through a 0.45 micron membrane, and evaporated. Preparative HPLC on a 22 mm×25 cm Whatman ODS-3 column eluting with 38% acetonitrile/62% water/0.05% trifluoroacetic acid gave the title compound as 44 mg (59% yield) of colorless film: 400 MHz ¹H NMR (CD₃OD) δ 7.06 (s, 4H), 4.39 (dd, 1H, J=9, 5 Hz), 2.72 (s, 3H), 2.59–2.45 (m, 2H), 2.52 (t, 2H, J=7 Hz), 2.45–2.35 (m, 1H), 2.33–2.24 (m, 1H), 2.26 (t, 2H, J=7 Hz), 1.96–1.44 (m, 13H), 1.41–1.21 (m, 2H), 0.96 (d, 3H, J=6 Hz), 0.93 (d, 3H, J=6 Hz), 0.91 (t, 3H, J=7 Hz).

EXAMPLE 17

2(R)-(2-(4-(1-n-Propyl)phenyl)ethyl)-1,5-pentanedioic acid 1-((R)-(S-p-methoxybenzyl) penicillamine, N-phenylamide)amide

Step A 5-tert-Butyl ester 2(R)-(2-(4-(1-n-propyl)phenyl)ethyl)-1,5-pentanedioic acid 1-((R)-(S-p-methoxybenzyl) penicillamine, N-phenylamide)amide: To a solution of 5-tert-butyl ester 2(R)-(2-(4-(1-propyl)phenyl)ethyl)-1,5-pentanedioic acid (260 mg, 0.777 mmol) in DMF (5 mL) were added hydroxybenzotriazole (HOBt) (157 mg, 1.16 mmol) and R-(S-p-methoxybenzyl)penicillamine, N-phenylamide (267 mg, 0.775 mmol). The mixture was cooled in an ice-bath and after 15 min EDC (178 mg, 0.928 mmol) was added. The reaction mixture was allowed to warm to room temperature and stirred overnight. It was then diluted with ethyl acetate, washed with water, 2N hydrochloric acid, saturated sodium hydrogencarbonate solution, dried (sodium sulfate) and evaporated. The product was purified by flash silica gel chromatography eluting with 15% ethyl acetate in hexane to afford 374 mg of the title amide.

Step B

2(R)-(2-(4-(1-n-Propyl)phenyl)ethyl)-1,5-pentanedioic acid 1-((R)-(S-p-methoxybenzyl)penicillamine, N-phenylamide)amide: A solution of 5-tert-butyl ester 2(R)-(2-(4-(1-propyl)phenyl)ethyl)-1,5-pentanedioic acid 1-(R-(S-p-methoxybenzyl)penicillamine phenylamide)amide (303 mg) in methylene chloride (10 mL) cooled in an ice-bath was treated with trifluoroacetic acid (2.5 mL) and then kept in the refrigerator overnight. The mixture was evaporated and coevaporated several times with toluene and then dried in vacuo to afford the title compound: mass spectrum: m/z 611 (M+Li); 400 MHz $^1$H NMR (CD$_3$OD): δ 0.90 (t, 3H), 1.42 (s, 3H), 1.57 (s, 3H), 3.75 (s, 3H), 3.88 (q, 2H), 6.80 (d, 2H), 7.00 (m, 4H), 7.31 (t, 2H), and 7.59 (d, 2H).

EXAMPLE 18

2(R)-(2-(4-(1-n-Propyl)phenyl)ethyl)-1,5-pentanedioic acid 1-((R)-(S-p-methoxybenzyl) penicillamine sulfone, N-phenylamide)amide

Step A 5-tert-Butyl ester 2(R)-(2-(4-(1-n-propyl)phenyl)ethyl)-1,5-pentanedioic acid 1-((R)-(S-p-methoxybenzyl) penicillamine sulfone, N-phenylamide)amide: A solution of 5-tert-butyl ester 2(R)-(2-(4-(1-n-propyl)phenyl)ethyl)-1,5-pentanedioic acid 1-(R)-(S-p-methoxybenzyl)penicillamine, N-phenylamide)amide (106 mg, 0.160 mmol) in methanol (10 mL) was treated with a solution of OXONE, monopersulfate compound (197 mg) in water (5 mL) until TLC (20% ethyl acetate in hexane) indicated complete conversion into a slower-moving product. The mixture was diluted with water (100 mL) and extracted with methylene chloride (2×50 mL). The combined organic extracts were dried (sodium sulfate) and evaporated. The product was purified by flash silica gel chromatography eluting with 20% ethyl acetate in hexane to afford 38 mg of the title amide.

Step B

2(R)-(2-(4-(1-n-Propyl)phenyl)ethyl)-1,5-pentanedioic acid 1-((R)-(S-p-methoxybenzyl)penicillamine sulfone, N-phenylamide)amide. A solution of 5-tert-butyl ester 2(R)-(2-(4-(1-n-propyl)phenyl)ethyl)-1,5-pentanedioic acid 1-(R)-(S-p-methoxybenzyl)penicillamine sulfone, N-phenylamide)amide (38 mg) in methylene chloride (2 mL) cooled in an ice-bath was treated with trifluoroacetic acid (0.3 mL) and then allowed to stand at room temperature until complete disappearance of starting compound. The mixture was evaporated and coevaporated several times with toluene and then dried in vacuo to afford the title compound: mass spectrum: m/z 659 (M+Na); 400 MHz $^1$H NMR (CD$_3$OD): δ 0.90 (t, 3H), 1.60 (s, 3H), 1.68 (s, 3H), 3.80 (s, 3H), 4.39 (d, 1H), 4.65 (d, 1H), 6.98 (s, 4H), 7.11 (t, 1H), and 7.58 (d, 2H).

EXAMPLE 19

2(R)-(2-(4-(1-n-Propyl)phenyl)ethyl)-4-(1-(4-(2-phthalimido))butyl)-1,5-pentandioic acid 1-(L-leucine, N-methylamide)amide

Step A 5-tert-Butyl ester 2(R)-(2-(4-(1-n-propyl)phenyl)ethyl)-4-(4-iodo-1-butyl)-1,5-pentandioic acid. To a solution of lithium diisopropylamide (2.3 mmol) in 15 ml of THF at −78° C. was added a solution of 5-tert-butyl ester 2-(2-(4-(1-n-propyl)phenyl)ethyl)-1,5-pentanedioic acid (1.0 g, 2.99 mmol) in 5 ml of THF and 1.5 ml of DMPU. After 1 h at −78° C., 1,4-diiodobutane (1.97 ml, 14.95 mmol) was added and the mixture stirred for 1 h at −78° C., 1 h at −60° C., and 18 h at −20° C. The reaction was quenched with excess 3N HCl, extracted with ethyl acetate, washed ethyl acetate with brine, dried over sodium sulfate, filtered, and concentrated in vacuo to give the title compound as a crude amber oil (5.32 g): 400MHz $^1$H NMR(CDCl$_3$) δ 7.06(m,4H), 3.19(m, 2H), 1.4(s,9H), 0.91(t,3H)

Step B

1-Benzyl ester 5-tert-butyl ester 2(R)-(2-(4-(1-n-propyl) phenyl)ethyl)-4-(4-iodo-1-butyl)-1,5-pentandioic acid. To a solution of 5.32 g of crude 5-tert-butyl ester 2(R)-(2-(4-(1-n-propyl)phenyl)ethyl)-4-(1-iodobutyl)-1,5-pentandioic acid in 50 ml of methylene chloride was added benzyl alcohol (1.06 ml, 10.3 mmol), 4-dimethylaminopyridine (DMAP) (162 mg, 1.33 mmol), and EDC(2.36 g, 12.36 mmol), and stirred overnight. The mixtured was diluted with methylene chloride, washed with water, saturated solution of sodium bicarbonate, and brine. The organics were dried with sodium sulfate, filtered, and concentrated in vacuo to give 6 g of a crude amber oil. The product was purified on silica-gel by eluting with 5% ether in hexane to give 1.10 g (mixture-1) of amber oil (containing the pure isomer and approximately 25% of unalkylated starting acid) and fractions giving 0.71 g (mixture-2) of amber oil (containing a mixture of isomers): 400MHz $^1$H NMR(CDCl$_3$) (mixture-1) δ 7.37 (m, 5H), 7.05–6.98(dd, 4H), 5.12(m, 2H), 3.12(t, 2H), 1.4(s, 9H), 0.91(t, 3H); (mixture-2) δ 7.37(m, 5H), 7.05–6.98(dd, 4H), 5.12(m, 2H), 3.12(m, 2H), 1.4(s, 9H), 1.35(s, 9H), 0.91(m, 3H).

Step C

1-Benzyl ester 5-tert-butyl ester 2(R)-(2-(4-(1-n-propyl) phenyl)ethyl)-4-(1-(4-(2-phthimido))butyl)-1,5-pentandioic acid. To a solution of 1-benzyl ester 5-tert-butyl ester 2(R)-(2-(4-(1-n-propyl)phenyl)ethyl)-4-(1-iodobutyl)-1,5-pentandioic acid (mixture-1)(1.10 g, 1.81 mmol) in 10 ml of DMF was added potassium phthalimide (336 mg, 1.81 mmol) and stirred at room temperature for 1 h and 50° C. for 2 h. The reaction was diluted with methylene chloride, washed with water, brine, dried over sodium sulfate, filtered, and concentrated in vacuo to give 1.22 g of a yellow oil. The product was purified on silica-gel by eluting with 20% ether in hexane and columned a second time on silica-gel eluting with 10% ethyl acetate in hexane to give 357 mg of the title compound (pure isomer of unknown configuration): 400MHz $^1$H NMR(CDCl$_3$) δ 7.80–7.68(m, 4H), 7.37(m, 5H), 7.05–6.98(dd, 4H), 5.1(s, 2H), 3.62(t, 2H), 1.35(s, 9H), 0.91 (m, 3H). MS: 539(M-benzyl group)

Step D 5-tert-Butyl ester 2(R)-(2-(4-(1-n-propyl)phenyl)ethyl)-4-(1-(4-(2-phthalimido))butyl)-1,5-pentandioic acid. To a solution of 1-benzyl ester 5-tert-butyl ester 2(R)-(2-(4-(1-n-propyl)phenyl)ethyl)-4-(1-(4-(2-phthalimido))-butyl)-1,5-pentandioic acid (357 mg, 0.57 mmol) in 5 ml of methanol was added catalytic Pd(OH)$_2$/C. After 3.5 h under 1 atmosphere of hydrogen, the mixture was filtered and concentrated in vacuo to give a colorless oil (297 mg): 400MHz $^1$H NMR(CDCl$_3$) δ 7.80–7.68(m, 4H), 7.05(s, 4H), 3.65(t, 2H), 1.35(s, 9H), 0.91(t, 3H).

Step E 5-tert-Butyl ester 2(R)-(2-(4-(1-n-propyl)phenyl)ethyl)-4-(1-(4-(2-phthalimido))butyl)-1,5-pentandioic acid 1-(L-leucine, N-methylamide)amide. To a solution of 5-tert-butyl ester 2(R)-(2-(4-(1-n-propyl)phenyl)ethyl)-4-(1-(4-(2-phthalimido))butyl)-1,5-pentandioic acid in 5 ml of DMF cooled to 0° C. was added NMM (67 ul, 0.61 mmol), HOBt (112 mg, 0.83 mmol), and Leucine methylamide hydrochloride. The mixture was stirred at 0° C. for 15 min, and EDC (127 mg, 0.61 mmol) was added and the mixture was allowed to warm slowly to room temperature and stirred overnight. The mixture was diluted with ethyl acetate and washed with 2N HCl, saturated sodium bicarbonate, and water. The organics were dried over sodium sulfate, filtered, and concentrated in vacuo. The product was purified on silica-gel eluting with 1% methanol in methylene chloride to give 279 mg of the title compound: 400MHz $^1$H NMR (CDCl$_3$) δ 7.85–7.70(m, 4H), 7.03(q, 4H), 6.30(m, 1H), 6.18(d, 1H), 3.65(t, 2H), 2.80(d, 3H), 1.35(s, 9H), 0.88(m, 9H). MS: 684 (M+Na)

Step F 5-tert-Butyl ester 2(R)-(2-(4-(1-n-propyl)phenyl)ethyl)-4-(4-amino-1-butyl)-1,5-pentandioic acid 1-(L-leucine, N-methylamide)amide. A solution of 5-tert-butyl ester 2(R)-(2-(4-(1-Propyl)phenyl)ethyl)-4-(1-(4-(2-phthalimido))butyl)-1,5-pentandioic acid 1-(L-leucine, N-methylamide)amide (217 mg, 0.33 mmol) in 1.97 ml of 0.5 Molar hydrazine in methanol was stirred overnight at room temperature. The mixture was concentrated and purified on silica-gel eluting with 5% methanol in methylene chloride containing 0.5% ammonium hydroxide to give the title compound as a clear glass: 400MHz $^1$H NMR(CDCl$_3$) δ 7.05(q, 4H), 6.40(m, 1H), 6.17(d, 1H), 2.78(d, 3H), 2.66(t, 2H), 1.37(s, 9H), 0.92(m, 9H).

Step G

2(R)-(2-(4-(1-n-propyl)phenyl)ethyl)-4-(4-amino-1-butyl)-1,5-pentandioic acid 1-(L-leucine, N-methylamide)amide. To a solution of 5-tert-butyl ester 2(R)-(2-(4-(1-n-propyl)phenyl)ethyl)-4-(4-amino-1-butyl)-1,5-pentandioic acid 1-(L-leucine, N-methylamide)amide (30 mg, 0.045 mmol) in 0.22 ml of methylene chloride was added TFA (0.22 ml) and the solution stirred at room temperature for 1 h. The reaction mixture was concentrated in vacuo, coeevaporated with toluene, and pumped under high vacuo to give 27 mg of the title compound as a white solid: 400MHz $^1$H NMR(CDCl$_3$) δ 7.85–7.78(m, 4H), 7.05(s, 4H), 3.65(t, 2H), 2.73(s, 3H), 0.91(m, 9H). MS: 618 (M+2Li).

EXAMPLE 20

2(R)-(2-(4-(1-n-Propyl)phenyl)ethyl)-4-(4-benzoylamino-1-butyl)-1,5-pentandioic acid 1-(L-leucine, N-methylamide)amide

Step A 5-tert-Butyl ester 2(R)-(2-(4-(1-n-propyl)phenyl)ethyl)-4-(4-benzoylamino-1-butyl)-1,5-pentandioic acid 1-(L-leucine, N-methylamide)amide. To a solution of 5-tert-butyl ester 2(R)-(2-(4-(1-n-propyl)phenyl)ethyl)-4-(4-amino-1-butyl-1,5-pentandioic acid 1-(L-leucine, N-methylamide) amide from Example 19 (40 mg, 0.075 mmol) in 1 ml of methylene chloride was added pyridine (121 ul, 1.5 mmol), DMAP (5 mg, 0.04 mmol), and benzoyl chloride (26 ul, 0.23 mmol). The mixture was stirred at room temperature 3 h, concentrated in vacuo, coeevaporated with toluene and pumped under high vacuo. The product was purified on silica-gel eluting with 2% methanol in methylene chloride to give 41 mg of product: 400MHz $^1$H NMR(CDCl$_3$) δ 7.75(d, 2H), 7.44(m, 2H), 7.02(q, 4H), 3.44(q, 2H), 2.78(d, 3H), 1.37(s, 9H), 0.90(m, 9H).

Step B

2(R)-(2-(4-(1-n-Propyl)phenyl)ethyl)-4-(4-benzoylamino-1-butyl)-1,5-pentandioic acid 1-(L-leucine, N-methylamide)amide. The product from Step A was dissolved in 0.30 ml of methylene chloride and 0.30 ml of TFA was added. After 3 h the mixture was concentrated in vacuo, coeevaporated with toluene and concentrated under high vacuo to give 36 mg of the title compound as a white solid: 400MHz $^1$H NMR(CDCl$_3$) δ 7.75(d, 2H), 7.42(m, 2H), 6.98(q, 4H), 3.42(q, 2H), 2.74(d, 3H), 0.88(m, 9H); MS: 602 (M+Na)

The following additional compounds were prepared according to the method of Example 20.

2(R)-(2-(4-(1-n-Propyl)phenyl)ethyl)-4-(4-pivaloylamino-1-butyl)-1,5-pentandioic acid 1-(L-leucine, N-methylamide)amide: 400MHz $^1$H NMR(CD$_3$OD) δ 7.06 (s,4H), 3.14(t, 2H), 2.73(s, 3H), 1.15(s, 9H), 0.94(m, 9H). MS: 560 (M+1).

2(R)-(2-(4-(1-n-Propyl)phenyl)ethyl)-4-(4-phenylsulfonylamino-1-butyl)-1,5-pentandioic acid 1-(L-leucine, N-methylamide)amide: 400MHz $^1$H NMR (CD$_3$OD) δ 7.83(m, 2H), 7.55(m, 3H), 7.06(s, 4H), 2.82(t, 2H), 2.74(d, 3H), 0.93(m, 9H). MS: 616 (M+1).

EXAMPLE 21

2(R)-(2-(4-(1-n-Propyl)phenyl)ethyl)-4-(4-(N'-phenylureido)-1-butyl)-1,5-pentandioic acid 1-(L-leucine, N-methylamide)amide

Step A 5-tert Butyl ester 2(R)-(2-(4-(1-n-propyl)phenyl)ethyl)-4-(4-(N'-phenylureido)-1-butyl)-1,5-pentandioic acid 1-(L-leucine, N-methylamide)amide. To a solution of 5-tert-butyl ester 2(R)-(2-(4-(1-n-propyl)phenyl)ethyl)-4-(4-amino-1-butyl)-1,5-pentandioic acid 1-(L-leucine, N-methylamide) amide (40 mg, 0.075 mmol) in 1 ml of methylene chloride was added DMAP (5 mg, 0.04 mmol), triethylamine (31 ul, 0.23 mmol), and phenyl isocyanate (25 ul, 0.23 mmol). The mixture was stirred at room temperature for 3 h, diluted with methylene chloride, washed with water, and brine. The organics were dried over sodium sulfate, filtered, and concentrated in vacuo. Purification on silica-gel eluting with 2% methanol in methylene chloride gave 44 mg of product: 400MHz $^1$H NMR(CDCl$_3$) δ 7.15(m, 9H), 2.78(d,3H), 1.37 (s, 9H), 1.33(s, 9H), 0.91 (m, 9H).

Step B

2(R)-(2-(4-(1-n-Propyl)phenyl)ethyl)-4-(4-(N'-phenylureido)-1-butyl)-1,5-pentandioic acid 1-(L-leucine, N-methylamide)amide. The product was dissolved in 0.30 ml of methylene chloride and 0.30 ml of TFA was added. After 2 h the mixture was concentrated in vacuo, coeevaporated with toluene and pumped under high vacuo to give 36 mg of the title compound as a white solid: 400MHz $^1$H NMR(CD$_3$OD) δ 7.27(m, 5H), 7.05(s, 4H), 2.73(d, 3H), 0.93(m, 9H). MS: 595 (M+1).

The following additional compound was prepared according to the method of Example 21.

2(R)-(2-(4-(1-n-Propyl)phenyl)ethyl)-4-(4-phenyloxycarbonylamino-1-butyl)-1,5-pentandioic acid 1-(L-leucine, N-methylamide)amide. Using the same reaction procedure and purification as described above, except phenyl chloroformate was substituted for phenyl isocyanate to give 34 mg of the title compound as a whim solid: 400MHz $^1$H NMR(CD$_3$OD) δ 7.38–7.08(m, 5H), 7.05(s, 4H), 3.15(t, 2H), 2.72(d, 3H), 0.93(m, 9H); MS: 596 (M+1).

EXAMPLE 22

2(R)-(2-(4-(1-n-Propyl)phenyl)ethyl)-4-(4-N'-benzyloxycarbonyl amino-L-prolylamino)-1-butyl)-1,5-pentandioic acid 1-(L-leucine, N-methylamide)amide

Step A 5-tert-Butyl ester 2(R)-(2-(4-(1-n-propyl)phenyl)ethyl)-4-(4-((N'-benzyloxycarbonylamino-L-prolyl)amino)-1-butyl)-

1,5-pentandioic acid 1-(L-leucine, N-methylamide)amide. To a solution of N-CBZ-(L)-proline (21 mg, 0.083 mmol) in 0.5 ml of DMF at 0° C., was added NMM (9 ul, 0.083 mmol), HOBt (15 mg, 0.113 mmol), and a solution of 5-tert-butyl ester 2(R)-(2-(4-(1-n-propyl)phenyl)ethyl)-4-(4-amino-1-butyl)-1,5-pentandioic acid 1-(L-leucine, N-methylamide)amide (40 mg, 0.075 mmol) in 1 ml of DMF. The mixture was stirred at 0° C. for 15 min, and EDC (18 mg, 0.090 mmol) was added and the mixture was allowed to warm to room temperature and stirred overnight. The mixture was diluted with ether and washed with water, 1N HCl, saturated sodium bicarbonate solution, and brine. The organics were dried over sodium sulfate, filtered, and concentrated in vacuo. The product was purified on silica-gel eluting with 2% methanol in methylene chloride to give 37 mg of product.

Step B

2(R)-(2-(4-(1-n-Propyl)phenyl)ethyl)-4-(4-N'-benzyloxycarbonyl amino-L-prolylamino)-1-butyl)-1,5-pentandioic acid 1-(L-leucine, N-methylamide)amide. The product from Step A was dissolved in 0.30 ml of methylene chloride and 0.30 ml of TFA was added. After 4 h the mixture was concentrated in vacuo, coeevaporated with toluene and pumped under high vacuo to give 31 mg of the title compound as a white solid: 400MHz $^1$H NMR(CD$_3$OD) δ 7.32(m, 5H), 7.05(s, 4H), 5.12(t, 2H), 2.72(d, 3H), 0.92(m, 9H); MS: 707 (M+1).

The following additional compound was prepared according to the method of Example 22.

2(R)-(2-(4-(1-n-Propyl)phenyl)ethyl)-4-(4-cyclopentylamino-1-butyl)-1,5-pentandioic acid 1-(L-leucine, N-methylamide)amide: 400MHz $^1$H NMR (CD$_3$OD) δ 8.10–7.05(s, 4H), 3.14(t, 2H), 2.72(d, 3H), 0.92(m, 9H); MS: 578 (M+Li).

EXAMPLE 23

2(R)-(2-(4-(1-n-Propyl)phenyl)ethyl)-4-(4-(2-carboxybenzoylamino)-1-butyl)-1,5-pentandioic acid 1-(L-leucine, N-methylamide)amide

Step A 5-tert-Butyl ester 2(R)-(2-(4-(1-n-Propyl)phenyl)ethyl)-4-(4-(2-carboxybenzoylamino)-1-butyl)-1,5-pentandioic acid 1-(L-leucine, N-methylamide)amide. To a solution of 5-tert-butyl ester 2(R)-(2-(4-(1-n-propyl)phenyl)ethyl)-4-(4-amino-1-butyl)-1,5-pentandioic acid 1-(L-leucine, N-methylamide)amide (38 mg, 0.072 mmol) in 1 ml of THF was added triethylamine (10 ul, 0.072 mmol), and phthalic anhydride (13 mg, 0.088 mmol) and the mixture stirred overnight at room temperature. The mixture was diluted with methylene chloride, washed with 1N HCl, water, and brine. The organics were dried over sodium sulfate, filtered, and concentrated in vacuo. Purification on silica-gel eluting with 2% methanol in methylene chloride containing 0.5% acetic acid gave 29 mg of product.

Step B

2(R)-(2-(4-(1-n-Propyl)phenyl)ethyl)-4-(4-(2-carboxybenzoylamino)-1-butyl)-1,5-pentandioic acid 1-(L-leucine, N-methylamide)amide. The product was dissolved in 0.30 ml of methylene chloride and 0.30 ml of TFA was added. After 4 h the mixture was concentrated in vacuo, coeevaporated with toluene and concentrated in high vacuo to give 26 mg of the title compound as a white solid: 400MHz $^1$H NMR(CD$_3$OD) δ 8.10–7.50(m, 4H), 7.05(s, 4H), 2.72(s, 3H), 0.91(m 9H); MS: 624 (M+1).

EXAMPLE 24

2(R)-(2-(4-(1-n-Propyl)phenyl)ethyl)-4-(4-cyano-1-butyl)-1,5-pentandioic acid 1-(L-leucine, N-phenylamide)amide

Step A

1-Benzyl ester 5-tert-butyl ester 2(R)-(2-(4-(1-n-propyl)phenyl)ethyl)-4-(4-cyano-1-butyl)-1,5-pentandioic acid. To a solution of 1-benzyl ester 5-tert-butyl ester 2(R)-(2-(4-(1-Propyl)-phenyl)-ethyl)-4-(4-iodo-1-butyl)-1,5-pentandioic acid (112 mg, 0.185 mmol) in 1 ml of DMF was added sodium cyanide (18 mg, 0.37 mmol) and the mixture stirred at room temperature overnight. A second reaction was run using a solution of 1-benzyl ester 5-tert-butyl ester 2(R)-(2-(4-(1-n-propyl)phenyl)ethyl)-4-(4-iodo-1-butyl)-1,5-pentandioic acid (103 mg, 0.17 mmol) in 1 ml of DMF. To this solution was added sodium cyanide (17 mg, 0.34 mmol) and the mixture was stirred at room temperature overnight. Both reactions were combined, diluted with ether, washed with water, and brine. The organics were dried over sodium sulfate, filtered, and concentrated in vacuo. The product was purified on silica-gel by eluting with 10% ethyl acetate in hexane to give 126 mg of the title compound: 400MHz $^1$H NMR(CDCl$_3$) δ 7.35(m, 5H), 7.01(q, 4H), 5.11(s, 2H), 2.25(t, 2H), 1.38(s, 9H), 0.91(t, 9H).

Step B 5-tert-Butyl ester 2(R)-(2-(4-(1-n-propyl)phenyl)ethyl)-4-(4-cyano-1-butyl)-1,5-pentandioic acid. To a solution of 1-benzyl ester 5-tert-butyl ester 2(R)-(2-(4-(1-n-propyl)phenyl)ethyl)-4-(4-cyano-1-butyl)-1,5-pentandioic acid (118 mg, 0.223 mmol) in 1.5 ml of methanol was added catalytic Pd(OH)$_2$/C. After 15 min under 1 atmosphere of hydrogen, the mixture was filtered and concentrated in vacuo to give 93 mg of the title compound as a colorless oil: 400MHz $^1$H NMR(CDCl$_3$) δ 7.08(s, 4H), 2.30(t, 2H), 1.40 (s, 9H), 0.92(t, 9H). MS: 433 (M+NH$_4$).

Step C 5-tert-Butyl ester 2(R)-(2-(4-(1-n-Propyl)phenyl)ethyl)-4-(4-cyano-1-butyl)-1,5-pentandioic acid 1-(L-leucine, N-phenylamide)amide. To a solution of 5-tert-butyl ester 2(R)-(2-(4-(1-n-propyl)phenyl)ethyl)-4-(4-cyano-1-butyl)-1,5-pentandioic acid (47 mg, 0.113 mmol) in 1 ml of DMF cooled to 0° C. was added NMM (14 ul, 0.124 mmol), HOBt (23 mg, 0.170 mmol), and (L)-Leucine anilide (26 mg, 0.124 mmol). The mixture was stirred at 0° C. for 15 min, and EDC (27 mg, 0.136 mmol) was added and the mixture was allowed to warm to room temperature and stirred overnight. The mixture was diluted with ether and washed with water, 1N HCl, saturated sodium bicarbonate solution, and brine. The organics were dried over sodium sulfate, filtered, and concentrated in vacuo. The product was purified on silica-gel eluting with 0.5% methanol in methylene chloride to give 47 mg of product.

Step D

2(R)-(2-(4-(1-n-Propyl)phenyl)ethyl)-4-(4-cyano-1-butyl)-1,5-pentandioic acid 1-(L-leucine, N-phenylamide)amide. The product from Step C was dissolved in 0.30 ml of methylene chloride and 0.30 ml of TFA was added. After 2 h at room temperature and overnight at 0° C. the mixture was concentrated in vacuo, coeevaporated with toluene and pumped under high vacuo to give 42 mg of the title compound as a white solid: 400MHz $^1$H NMR(CDCl$_3$) δ 7.55–7.05(m, 5H), 7.01(s, 4H), 2.43(t, 2H), 1.00–0.91(m, 9H); MS: 548 (M+1).

EXAMPLE 25

Enzyme Inhibition Assays

Inhibition of Human Fibroblast Stromelysin:

Activation: Human recombinant stromelysin was purchased from Celltech (Slough, U.K.) as a proenzyme of 55 kD in a buffer consisting of 20 mM Tris, 10 mM CaCl$_2$, 0.05% Brij-35, and 0.2% NAN$_3$, pH=7.5. The material was activated as described.(Harrison, R. K., Teahan, J., and Stein, R. L. A Semi-Continuous HPLC-Based Assay for Stromelysin. *Anal. Biochem.* 1989, 180, 110–113). Briefly, to 1.0 mL of a 2.2 µM solution of prostromelysin was added 20 µL of a 1.0 µM solution of trypsin in assay buffer (20 mM HEPES, 10 mM CaCl$_2$, 0.05% Brij-35, pH=7.5, [trypsin]$_{final}$=20 nM. The solution was incubated at 37° C. for 30 minutes. The reaction was quenched by addition of a 50 fold molar excess of soybean trypsin inhibitor bound to agarose (Sigma), and the solution centrifuged to remove the trypsin:inhibitor complex.

K$_i$ Determinations: Stock solutions of inhibitors were prepared by dissolving the compounds in DMSO. The inhibitors were further diluted in assay buffer to eight different concentrations encompassing the approximate K$_i$, and covering a 200 fold range. To 50 µL of each of the inhibitor solutions was added 25 µL of an 8 nM solution of trypsin-activated stromelysin, [DMSO]=1.8%. The solution was allowed to incubate for 4 h to reach equilibrium. To this solution was added 60 µL of a 12.8 µM solution of the substrate Arg-Pro-Lys-Pro-Leu-Ala-Phe-Trp-NH$_2$ (k$_c$/K$_m$= 12.000 M$^{-1}$s$^{-1}$) (Niedzwiecki, L., Teahan, J., Harrison, R. K., Stein, R. L. Substrate Specificity of the Human Metalloproteinase Stromelysin and the Development of Continuous, Fluorometric Assays. *Biochem.* 1992, 31, 12618–12623), and the reaction was allowed to proceed for 18 h. In the reaction [S]=5.7 µM and [E]=1.5 nM. The reaction was quenched by addition of 50 µL of 0.15M phosphoric acid, and 100 µL of the reaction mixture was injected onto the HPLC. Since the reactions were run under first order conditions, ([S]<<K$_m$, K$_m$=0.5 mM), the pseudo first order rate constant, k$_{obs}$, was determined for each of the inhibitor concentrations from the peak area corresponding to unreacted substrate in the inhibited sample, and the peak area for substrate at time=0:

$$\ln\left(\frac{area_{inhib}}{area_{t=0}}\right) = -k_{obs}t$$

Values of K$_i$ were determined from the ratio of the rate constants for inhibited and control sample (no inhibitor) plotted as a function of the inhibitor concentration, and fit to the following equation:

$$\frac{k_{inhib}}{k_{control}} = \frac{1}{1+([I]/K_i)}$$

Inhibition of Human Fibroblast Collagenase:

Activation: Human fibroblast collagenase was purchased from Celltech (Slough, U.K.). The material was received as a proenzyme of 54 kD at a concentration of 1.2 µM in a buffer consisting of 20 mM Tris, 5 mM CaCl$_2$, 0.15M NaCl, and 0.01% NaN$_3$. The material was activated with trypsin using the same procedure as for stromelysin, with the addition that the activation buffer contained 40 nM prostromelysin.

Ki Determinations. Stock solutions of inhibitors were prepared by dissolving the material in DMSO The inhibitors were further diluted in assay buffer to eight different concentrations encompassing the approximate K$_i$ and covering a 200 fold range. Final DMSO concentration was 2.8%. To 50 uL of the inhibitor solutions was added 25 uL of a 108 nM solution of trypsin activated collagenase. The solution was allowed to incubated for 4 h to reach equilibrium. To this solution was added 60 uL of a 56 µM solution of the substrate DNP-Pro-Leu-Gly-Leu-Trp-Ala-dArg-NH$_2$ (kc/Km=270,000M$^{-1}$s$^{-1}$) (Stack, M. S.; Gray, R. D. Comparison of Vertebrate Collagenase and Gelatinase Using a New Fluorogenic Substrate Peptide. *J. Biol. Chem.* 1989, 264, 4277–4281), and the reaction was allowed to proceed for 18 h. In the incubation mixture [S]=25 µM, [E]=20 nM. The reaction was quenched by addition of 50 uL of 0.15M phosphoric acid. The reaction mixture was injected onto the HPLC. The calculation of K$_i$ was the same as for stromelysin.

Inhibition of Human Gelatinase A:

Activation: Human 72 kD gelatinase was purchased from Celltech (Slough, U.K.) as a proenzyme at a concentration of 1.5 µM in a buffer consisting of 20 mM Tris, 5 mM CaCl$_2$ 150 mM NaCl, 0.01% brij, 0.02% NaN$_3$, pH=7.5. The proenzyme was activated by incubation of 500 µL proenzyme with 50 µL of a 11 mM solution aminophenyl mercuric acetate in NaOH (pH=11) at 25° C. for 120 min.

Ki Determinations. Determination of K$_i$ values for gelatinase A were identical to that of collagenase and stromelysin with the exception that incubation of the enzyme-inhibitor mixture with the substrate was performed for only 2 h. [S]=25 µM, [E]=20 nM.

All compounds specifically cited in the Examples have a K$_i$≦6 µM against stromelysin, approximately ≦10 µM against gelatinase, and were active (although less so) against collagenase.

The inhibitors of matrix metalloproteinases claimed herein may also be evaluated for in vivo efficacy in several animal models of articular cartilage degradation. Stromelysin has been immunolocalized to synovial and cartilage tissues in three models of antigen-induced arthritis in rats: streptococcal cell wall (SCW) arthritis, adjuvant arthritis (AA), and type II collagen-induced arthritis. The methods for inducing cartilage destruction in these models is described in detail in the literature: a) J. P. Case, H. Sano, R. Lafyatis, E. F. Remmers, G. K. Kumkumian, R. L. Wilder "Transin/Stromelysin Expression in the Synovium of Rats with Experimental Erosive Arthritis" *J. Clin. Investig.* 84, 1731–1740 (1989); b) K. A. Hasty, R. A. Reife, A. H. Kang, J. M. Stuart "The Role of Stromelysin in the Cartilage Destruction that Accompanies Inflammatory Arthritis" *Arthr. Rheum.* 33, 388–397 (1990). Compounds claimed herein would be evaluated for their ability to lessen or prevent inflammation and joint destruction as measured by reduction in joint swelling as well as radiological and histological examination of joints and arthritic lesions. Compounds that inhibit matrix metalloproteinases have been reported to be efficacious in lessening joint swelling, soft tissue swelling, inflammation, and bone and cartilage loss in the rat adjuvant arthritis model: M. J. DiMartino, C. E. Wolff, W. High, M. J. Crimmin, W. A. Galloway "Anti-inflammatory and Chondroprotective Activities of a Potent Metalloproteinase Inhibitor" *J. Cell. Biochem.* Suppl. 15E, 179 (1991).

What is claimed is:

1. A compound of Formula I

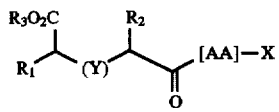

or a pharmaceutically acceptable salt thereof wherein:

Y is —CH$_2$—, CH(C$_{1-3}$alkyl);

R$_1$ is mono- or di-substituted C$_{1-6}$alkyl, wherein the substituents are independently selected from the group consisting of:
  (a) hydrogen,
  (b) aryl group selected from the group consisting of:
    (1) phenyl,
    (2) naphthyl,
    (3) pyridyl, (4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl,
which can be mono- or di-substituted with substitutents independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, or $C_{1-6}$alkylcarbonyl;

$R_2$ is aryl$C_{1-4}$alkyl or aryl substituted $C_{1-4}$alkyl or biaryl $C_{1-4}$alkyl wherein the substituent is $C_{1-3}$alkyl, and wherein the aryl group is selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl,
and mono and di-substituted aryl as defined above in items (1) to (27) wherein the substitutents on the aryl group are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

$R_3$ is
(a) H,
(b) Z, where Z is a pharmaceutically acceptable counterion,
(c) $C_{1-10}$alkyl,
(d) aryl or aryl $C_{1-3}$alkyl, wherein the aryl group is selected from the group consisting of
(1) phenyl, and
(2) substituted phenyl, wherein the substitutents is carboxy, carboxy$C_{1-3}$alkyl, aminocarbonyl, $C_{1-6}$alkylaminocarbonyl;

AA is an amino acid of formula II

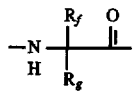

wherein $R_f$ and $R_g$ are individually selected from:
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino substituted $C_{2-6}$alkyl
(g) aminocarbonyl $C_{1-6}$alkyl,
(h) mono- or di-$C_{1-6}$alkyl amino $C_{2-6}$alkyl,
(i) guanidino $C_{2-6}$alkyl,
(j) substituted phenyl $C_{1-6}$alkyl, wherein the substitutent is hydrogen, hydroxy, carboxy, $C_{1-4}$ alkyl, or $C_{1-4}$alkyloxy,
(k) substituted indolyl $C_{1-6}$alkyl, wherein the substitutent is hydrogen, hydroxy, carboxy, $C_{1-4}$ alkyl, or $C_{1-4}$alkyloxy,
(l) substituted imidazolyl $C_{2-6}$alkyl wherein the substitutent is hydrogen, hydroxy, carboxy, $C_{1-4}$ alkyl, or $C_{1-4}$alkyloxy,
(m) substituted pyridyl $C_{1-6}$alkyl wherein the substitutent is hydrogen, hydroxy, carboxy, $C_{1-4}$ alkyl, or $C_{1-4}$alkyloxy,
(n) substituted pyridylamino $C_{1-6}$alkyl wherein the substitutent is hydrogen, hydroxy, carboxy, $C_{1-4}$ alkyl, or $C_{1-4}$alkyloxy,
(o) substituted pyrimidinyl $C_{1-6}$alkyl wherein the substitutent is hydrogen, hydroxy, carboxy, $C_{1-4}$ alkyl, or $C_{1-4}$alkyloxy, X is

wherein $R_5$ and $R_6$ are each individually selected from the group consisting of:
(a) H,
(c) Aryl or Aryl$C_{1-6}$alkyl, wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,

(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl,
(25) benzoxazolyl,
(26) thiazolyl, and
(27) oxazolyl and mono and di-substituted Aryl as defined above in items (1) to (27) wherein the substitutents are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl.

2. A compound according to claim 1 wherein:
$R_2$ is aryl$C_{1-4}$alkyl, or biaryl$C_{1-4}$alkyl wherein the aryl group is selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl, and mono and di-substituted aryl as defined above in items (1) to (27) wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl.

3. A compound according to claim 2 wherein:
$R_1$ is substituted $C_{1-6}$alkyl, wherein the substituent is selected from the group consisting of:
(a) hydrogen,
(b) Aryl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl, and
(9) indolyl;

and mono and di-substituted Aryl as defined above in items (1) to (9) wherein the substitutents are independently selected from $C_{1-6}$alkyl, $C_{1-3}$alkyloxy, halo, hydroxy, amino, $C_{1-3}$alkylamino, amino$C_{1-3}$alkyl, carboxyl, carboxyl$C_{1-3}$alkyl, and $C_{1-3}$alkylcarbonyl.

4. A compound according to claim 3 wherein:
$R_3$ is
(a) H,
(b) Z,
(c) $C_{1-4}$alkyl,
(d) phenyl, substituted phenyl, wherein the substitutent is carboxy, carboxy $C_{1-3}$alkyl, amino carbonyl.

5. A compound according to claim 3 wherein:
AA is an amino acid selected from glycine, alanine, valine, leucine, isoleucine, 2-tert-butyl-glycine, penicilliamine, serine, threonine, aspartic acid, asparagine, glutamic acid, glutamine, lysine, hydroxylysine, homohistidine, arginine, phenylalanine, tyrosine, tryptophan, cysteine, methionine, ornithine, homoserine and citrulline.

6. A compound according to claim 4 wherein:
the substituents are selected from:
(a) hydrogen,
(b) $C_{1-4}$alkyl,
(c) mercapto $C_{1-3}$alkyl,
(d) hydroxy $C_{1-4}$alkyl,
(e) carboxy $C_{1-4}$alkyl,
(f) amino $C_{1-4}$alkyl,
(g) aminocarbonyl $C_{1-4}$alkyl,
(h) mono- or di-$C_{1-4}$alkyl amino $C_{1-4}$alkyl,
(i) guanidino $C_{1-4}$alkyl,
(j) substituted phenyl $C_{1-4}$alkyl, wherein the substituent is hydrogen, hydroxy, carboxy, or $C_{1-3}$ alkyl,
(k) substituted indolyl $C_{1-4}$alkyl, wherein the substituent is hydrogen, hydroxy, carboxy, or $C_{1-3}$ alkyl,
(l) substituted imidazolyl $C_{2-4}$alkyl wherein the substituent is hydrogen, hydroxy, carboxy, or $C_{1-4}$ alkyl.

7. A compound according to claim 6 wherein:
X is

wherein $R_5$ and $R_6$ are each individually selected from the group consisting of:
(a) H,
(b) Aryl or Aryl$C_{1-4}$alkyl, wherein the aryl group is selected from the group consisting of
(1) phenyl,
(2) naphthyl,
(3) pyridyl,
(4) thienyl,
(5) imidazolyl,
(6) tetrazolyl,
(7) pyrazinyl,
(8) pyrimidyl,
(9) benzofuryl,
(10) benzothienyl,
(11) pyrazolyl, and

(12) indolyl, and mono and di-substituted Aryl as defined above in items (1) to (12) wherein the substitutents are independently selected from $C_{1-3}$alkyl, $C_{1-3}$alkyloxy, halo, hydroxy, amino, $C_{1-3}$alkylamino, amino$C_{1-3}$alkyl, carboxyl, carboxyl$C_{1-3}$alkyl, and $C_{1-3}$alkylcarbonyl.

8. A compound according to claim 7 wherein

Y is —CH$_2$—

$R_1$ is hydrogen, substituted $C_{1-4}$alkyl or substituted $C_{2-4}$alkenyl wherein the substituent is hydrogen, and Aryl wherein the aryl is selected from the group consisting of $R_2$ is aryl$C_{1-4}$alkyl, or biaryl$C_{1-4}$alkyl wherein the aryl group is is selected from the group consisting of phenyl, thienyl, pyridyl, or naphthyl;

$R_3$ is
(a) H, or
(b) Z;

$R_f$ is H;

$R_g$ is
(a) hydrogen;
(b) $C_{1-6}$alkyl; or
(c) guanidino $C_{1-6}$alkyl $R_5$ is H; and $R_6$ is Aryl or monosubstitued aryl, wherein the aryl is phenyl and the substituent is selected from $C_{1-8}$alkyl, halo, and hydroxy $R_b$ is H.

9. A compound according to claim 7 wherein

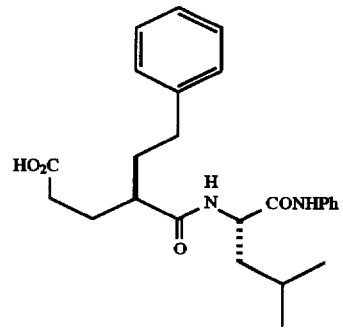

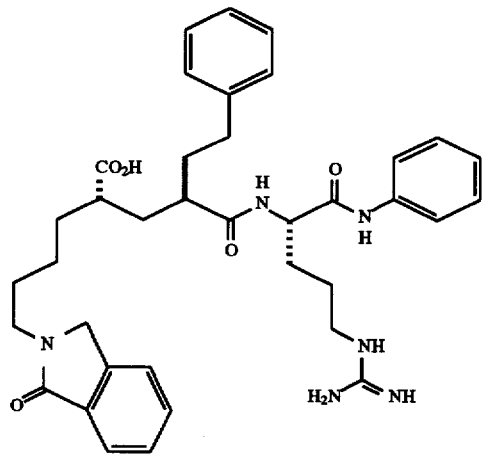

-continued

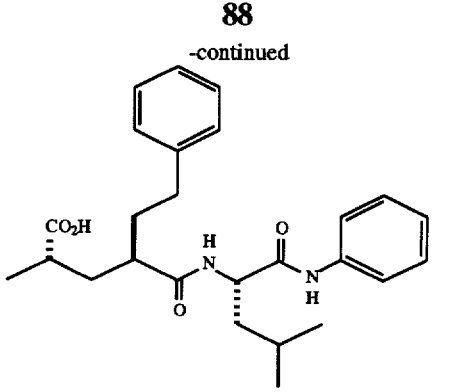

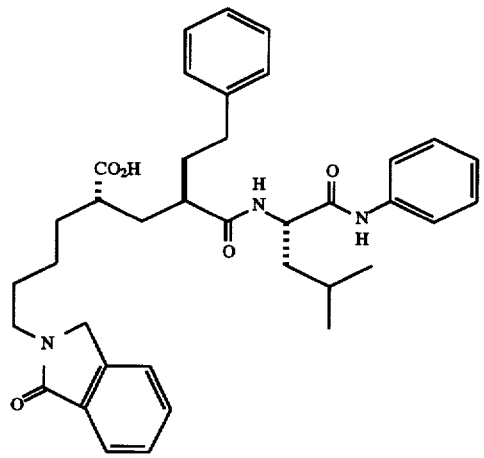

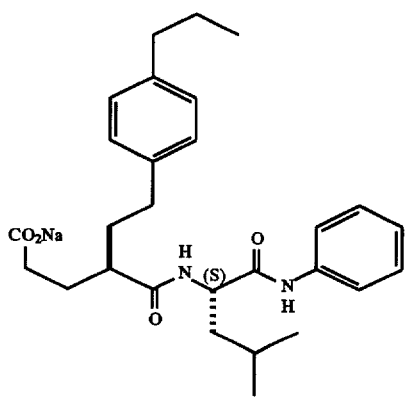

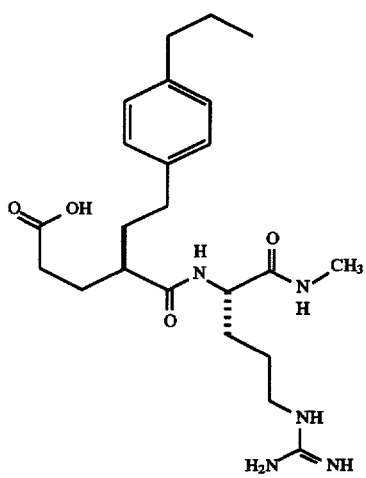

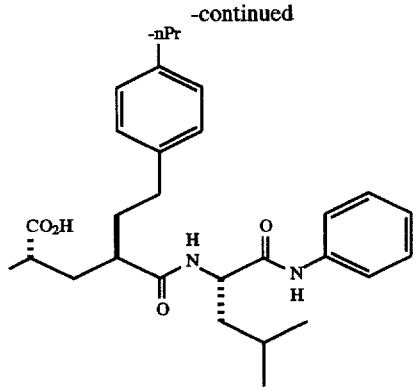

10. A pharmaceutical composition for treating a matrix metalloendoproteinase-mediated disease comprising a pharmaceutical carrier and a non-toxic effective amount of the compound of claim 1.

11. A method for inhibiting the lytic activity of metalloendoproteinases comprising administering to a subject suffering from matrix metalloendoproteinase mediated disease, and inhibitory amount of the compound of claim 1.

12. A method according to claim 11 in which the metalloendoproteinase is stromelysin.

13. A method according to claim 11 in which the metalloendoproteinase is collagenase.

14. A method according to claim 11 in which the metalloendoproteinase is gelatinase.

15. A method for inhibiting the activity of stromelysin comprising administering to a subject suffering from a stromelysin mediated disease, a therapeutic amount of the compound of claim 1.

16. A method according to claim 15 wherein the stromelysin inhibitor is administered in an amount of from about 0.01 to 50 mg of the compound per kilogram body weight.

17. A method of treating matrix metalloendo-proteinase-mediated disease comprising the administration to a subject in need of such a therapeutically effective amount of a compound claim 1.

18. A compound of Formula I

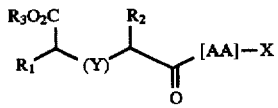

or a pharmaceutically acceptable salt thereof wherein:

Y is —$CH_2$— $CH(C_{1-3}alkyl)$;

$R_1$ is mono- or di-substituted $C_{1-6}$alkyl, wherein the substituents are independently selected from the group consisting of:
(a) hydrogen,
(b) aryl group selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl, which can be mono- or di-substituted with substitutents independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, or $C_{1-6}$alkylcarbonyl,;

$R_2$ is aryl$C_{1-4}$alkyl or aryl substituted $C_{1-4}$alkyl or biaryl $C_{1-4}$alkyl wherein the substituent is $C_{1-3}$alkyl, and wherein the aryl group is selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) thiazolyl,
(25) oxazolyl,
(26) benzthiazolyl, and
(27) benzoxazolyl, and mono and di-substituted aryl as defined above in items (1) to (27) wherein the substitutents on the aryl group are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

$R_3$ is
(a) H,
(b) Z, where Z is a pharmaceutically acceptable counterion,
(c) $C_{1-10}$alkyl,
(d) aryl or aryl $C_{1-3}$alkyl, wherein the aryl group is selected from the group consisting of
(1) phenyl, and
(2) substituted phenyl, wherein the substitutent is carboxy, carboxy$C_{1-3}$ alkyl, aminocarbonyl, $C_{1-6}$alkylaminocarbonyl;

AA is an amino acid of formula II

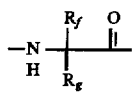

wherein $R_f$ and $R_g$ are individually selected from:
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino substituted $C_{2-6}$alkyl
(g) aminocarbonyl $C_{1-6}$alkyl,
(h) mono- or di-$C_{1-6}$alkyl amino $C_{2-6}$alkyl,
(i) guanidino $C_{2-6}$alkyl,
(j) substituted phenyl $C_{1-6}$alkyl, wherein the substitutent is hydrogen, hydroxy, carboxy, $C_{1-4}$ alkyl, or $C_{1-4}$alkyloxy,
(k) substituted indolyl $C_{1-6}$alkyl, wherein the substitutent is hydrogen, hydroxy, carboxy, $C_{1-4}$ alkyl, or $C_{1-4}$alkyloxy,
(l) substituted imidazolyl $C_{2-6}$alkyl wherein the substitutent is hydrogen, hydroxy, carboxy, $C_{1-4}$ alkyl, or $C_{1-4}$alkyloxy,
(m) substituted pyridyl $C_{1-6}$alkyl wherein the substitutent is hydrogen, hydroxy, carboxy, $C_{1-4}$ alkyl, or $C_{1-4}$alkyloxy,
(n) substituted pyridylamino $C_{1-6}$alkyl wherein the substitutent is hydrogen, hydroxy, carboxy, $C_{1-4}$ alkyl, or $C_{1-4}$alkyloxy,
(o) substituted pyrimidinyl $C_{1-6}$alkyl wherein the substitutent is hydrogen, hydroxy, carboxy, $C_{1-4}$ alkyl, or $C_{1-4}$alkyloxy, X is

wherein $R_5$ is Aryl or Aryl$C_{1-6}$alkyl, wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl,
(25) benzoxazolyl,
(26) thiazolyl, and
(27) oxazolyl and mono and di-substituted Aryl as defined above in items (1) to (27) wherein the substitutents are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl; and $R_6$ is
(a) H,
(b) $C_{1-10}$alkyl,
(c) Aryl or Aryl$C_{1-6}$alkyl, wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl,
(25) benzoxazolyl,
(26) thiazolyl, and
(27) oxazolyl and mono and di-substituted Aryl as defined above in items (1) to (27) wherein the substitutents are independently selected from $C_{1-6}$alkyl, $C_{1-6}$alkyloxy, hydroxy$C_{1-6}$alkyl, $C_{1-6}$alkoxy$C_{1-6}$alkyl, halo, hydroxy, amino, $C_{1-6}$alkylamino, amino$C_{1-6}$alkyl, carboxyl, carboxyl$C_{1-6}$alkyl, and $C_{1-6}$alkylcarbonyl.

19. A compound
a) 2(R)-(2-(4-(1-n-Propyl)phenyl)ethyl)-1,5-pentanedioic acid 1-(L-leucine, N-phenylamide)amide,
b) 2(R)-(2-(4-(1-n-Propyl)phenyl)ethyl)-1,5-pentanedioic acid 1-(2(S)-t-butyl)glycine, N-phenylamide)amide,
c) 2(R)-(2-(4-(1-n-Propyl)phenyl)ethyl)-1,5-pentanedioic acid 1-(2(S)-t-butyl)glycine, N-(4-pyridyl)amide) amide,
d) 2(R)-(2-(4-(1-n-Propyl)phenyl)ethyl)-1,5-pentanedioic acid 1-(L-arginine, N-methylamide)amide,
e) 2(R)-(2-(4-(1-n-Propyl)phenyl)ethyl)-4-methyl-1,5-pentanedioic acid 1-(L-leucine, N-phenylamide)amide,
f) 2(R)-(2-(4-(1-n-Propyl)phenyl)ethyl)-4-methyl-1,5-pentanedioic acid 1-(2(S)-t-butyl)glycine, N-phenylamide)amide,
g) 2(R)-(2-(4-(1-n-Propyl)phenyl)ethyl)-4-methyl-1,5-pentanedioic acid 1-(L-leucine, N-(4-pyridyl)amide) amide,
h) 2(R)-(2-(4-(1-n-Propyl)phenyl)ethyl)-4-methyl-1,5-pentanedioic acid 1-(L-arginine, N-phenylamide) amide, i) 2(R)-(2-(4-(1-n-Propyl)phenyl)ethyl)-4-methyl-1,5-pentanedioic acid 1-(L-phenylalanine, N-4-pyridyl) amide)amide, j) 2(R)-(2-(4-(4-fluorophenyl)phenyl)ethyl)-4-methyl-1,5-pentanedioic acid 1-(L-leucine, N-phenylamide) amide, k) 2(R)-(2-(4-(phenyl)phenyl)ethyl)-4-methyl-1,5-pentanedioic acid 1-(L-leucine, N-phenylamide)amide, l) 2(R)-(2-(4-(4-methoxyphenyl)phenyl)ethyl)-4-methyl-1,5-pentanedioic acid 1-(L-leucine phenylamide) amide, m) 2(R)-(2-(4-(4-methylphenyl)phenyl)ethyl)-4-methyl-1,5-pentanedioic acid 1-(L-leucine phenylamide) amide, n) 2(R)-(2-(4-(4-hydroxy-n-butyl)-phenyl)-ethyl)-4-methylpentanedioic acid 1-(S-leucine phenylamide) amide, n) 2(R),4(S)-(2-(4-(3-hydroxy-n-propyl)phenyl)ethyl)-4-methyl-1,5-pentanedioic acid 1-(L-leucine, N-phenylamide)amide, o) 2(R)-(2-phenylethyl)-4-methyl-1,5-pentanedioic acid 1-(L-leucine, N-phenylamide)amide, p) 2(R)-(2-(4-(1-n-Propyl)phenyl)ethyl)-1,5-pentanedioic acid 1-(L-leucine, N-ethylamide)amide, q) 2(R)-(2-(4-(1-n-Propyl)phenyl)ethyl)-1,5-pentanedioic acid 1-(L-leucine, N-isopropylamide)amide, r) 2(R)-(2-(4-(1-n-Propyl)phenyl)propyl)-1,5-pentanedioic acid 1-(2(S)-tert-butyl-glycine, N-(4-pyridyl)amide)amide, s) 2(R)-(3-(4-(1-n-Propyl)phenyl)propyl)-1,3-pentanedioic acid 1-(L-leucine, N-phenylamide)amide, t) 2(R)-(2-(4-(1-n-Propyl)phenyl)ethyl)-4-hexyl-1,5-pentanedioic acid 1-(L-leucine, N-phenylamide)amide, u) 2(R)-(2-(4-(1-n-Propyl)phenyl)ethyl)-4-butyl-1,5-pentanedioic acid 1-(L-leucine, N-phenylamide)amide, v) 2(R)-(2-(4-(1-n-Propyl)phenyl)ethyl)-4-(3-methylbenzyl)-1,5-pentanedioic acid 1-(L-leucine, N-phenylamide)amide, w) 2(R)-(2-(4-(1-Propyl)phenyl)ethyl)-4-carboxy-1,9-nonanedioic acid 1-(L-leucine, N-methylamide)amide 9-phenylamide, x) 2(R)-(2-(4-(1-n-Propyl)phenyl)ethyl)-4-carboxy-1,9-nonanedioic acid 1-(L-leucine, N-methylamide)amide 9-tert-butylamide, y) 2(R)-(2-(4-(1-n-Propyl)phenyl)ethyl)-4-carboxy-1,9-nonanedioic acid 1-(L-leucine, N-methylamide)amide 9-benzylamide, z) 2(R)-(2-(4-(1-n-Propyl)phenyl)ethyl)-4-carboxy-1,9-nonanedioic acid 1-(L-leucine, N-methylamide)amide 9-(1(R)-phenylethyl)amide, ab) 2(R)-(2-(4-(1-n-Propyl)phenyl)ethyl)-4-carboxy-1,9-nonanedioic acid 1-(L-leucine, N-methylamide)amide 9-(1(S)-phenylethyl)amide, ac) 2(R)-(2-(4-(1-n-Propyl)phenyl)ethyl)-4-carboxy-1,9-nonanedioic acid 1-(L-leucine, N-methylamide)amide 9-(N-methyl-N-phenyl)amide, ad) 2(R)-(2-(4-(1-Propyl)phenyl)ethyl)-4-carboxy-1,9-nonanedioic acid 1-(L-leucine, N-methylamide)amide, ae) 2(R)-(2-(4-(1-n-Propyl)phenyl)ethyl)-4-(4-benzoylamino-1-butyl)-1,5-pentandioic acid 1-(L-leucine, N-methylamide)amide, af) 2(R)-(2-(4-(1-n-Propyl)phenyl)ethyl)-4-(4-phenylsulfonylamino-1-butyl)-1,5-pentandioic acid 1-(L-leucine, N-methylamide)amide, ag) 2(R)-(2-(4-(1-n-Propyl)phenyl)ethyl)-4-(4-(N'-phenylureido)-1-butyl)-1,5-pentandioic acid 1-(L-leucine, N-methylamide)amide, ah) 2(R)-(2-(4-(1-n-Propyl)phenyl)ethyl)-4-(4-phenyloxycarbonyl-amino-1-butyl)-1,5-pentandioic acid 1-(L-leucine, N-methylamide)amide, ai) 2(R)-(2-(4-(1-n-Propyl)phenyl)ethyl)-4-(4-N'-benzyloxycarbonyl amino-L-prolylamino)-1-butyl)-1,5-pentandioic acid 1-(L-leucine, N-methylamide) amide, aj) 2(R)-(2-(4-(1-n-Propyl)phenyl)ethyl)-4-(4-(2-carboxybenzoylamino)-1-butyl)-1,5-pentandioic acid 1-(L-leucine, N-methylamide)amide, and ak) 2(R)-(2-(4-(1-n-Propyl)phenyl)ethyl)-4-(4-cyano-1-butyl)-1,5-pentandioic acid 1-(L-leucine, N-phenylamide)amide.

* * * * *